United States Patent
Agris et al.

(10) Patent No.: US 9,975,922 B2
(45) Date of Patent: May 22, 2018

(54) PEPTIDE INHIBITOR OF HIV REVERSE TRANSCRIPTION

(71) Applicant: THE RESEARCH FOUNDATION FOR THE STATE UNIVERSITY OF NEW YORK, Albany, NY (US)

(72) Inventors: Paul F. Agris, Albany, NY (US); Carol Hall, Raleigh, NC (US); Xingqing Xiao, Raleigh, NC (US)

(73) Assignees: The Research Foundation For The State University of New York, Albany, NY (US); North Carolina State University, Raleigh, NC (US)

( * ) Notice: Subject to any disclaimer, the term of this patent is extended or adjusted under 35 U.S.C. 154(b) by 0 days. days.

(21) Appl. No.: 15/030,739

(22) PCT Filed: Oct. 21, 2014

(86) PCT No.: PCT/US2014/061606
§ 371 (c)(1),
(2) Date: Apr. 20, 2016

(87) PCT Pub. No.: WO2015/061339
PCT Pub. Date: Apr. 30, 2015

(65) Prior Publication Data
US 2016/0257715 A1  Sep. 8, 2016

Related U.S. Application Data

(60) Provisional application No. 61/893,600, filed on Oct. 21, 2013.

(51) Int. Cl.
*A61K 38/00* (2006.01)
*C07K 7/08* (2006.01)

(52) U.S. Cl.
CPC ............... *C07K 7/08* (2013.01); *A61K 38/00* (2013.01)

(58) Field of Classification Search
CPC .................................. A61K 38/00; C07K 7/08
USPC .................................. 530/300, 326; 514/21.5
See application file for complete search history.

(56) References Cited

U.S. PATENT DOCUMENTS

| | | | | |
|---|---|---|---|---|
| 6,706,869 B1 * | 3/2004 | Wong | ............... | C07K 14/47 435/252.3 |
| 7,745,391 B2 * | 6/2010 | Mintz | ............... | G06F 19/24 514/19.3 |
| 8,410,336 B2 * | 4/2013 | Lutfiyya | ............... | C07K 14/415 435/419 |
| 2004/0031072 A1 | 2/2004 | La Rosa et al. | | |
| 2004/0180380 A1 | 9/2004 | Lee et al. | | |
| 2005/0255491 A1 * | 11/2005 | Lee | ............... | B82Y 5/00 435/6.18 |
| 2013/0031668 A1 | 1/2013 | Brover et al. | | |

FOREIGN PATENT DOCUMENTS

| WO | 2011/057029 A1 | 5/2011 |
|---|---|---|
| WO | 2015/061339 A2 | 4/2015 |

OTHER PUBLICATIONS

Spears, et al., Amino Acid Signature Enables Proteins to Recognize Modified tRNA, Biochemistry, 2014, 53(7), pp. 1125-1133.
GenBank: CCD16211.1, Unnamed protein product [Trypanosoma congolense IL3000], embl accession CAE001002199.1, May 11, 2012.
NCBI Reference Sequence: WP_005029773.1, Cobalt transporter [Bilophila wadsworthia], May 27, 2013.
GenBank: ERN10592.1, Hypothetical protein AMITR_s00028p001297770 [Amborella trichopoda], accession KI392812.1, Sep. 30, 2013.
NCBI Reference Sequence: WP_020515231.1, Hypothetical protein [Actinoplanes globisporus], Accession WP_020515231, Jul. 9, 2013.
NCBI Reference Sequence: WP_014433126.1, Hypothetical protein [Caldilinea aerophila], Accession WP_014433126, May 19, 2013.
NCBI Reference Sequence: WP_021030245.1, Hypothetical protein [*Segniliparus rugosus*], Accession WP_021030245, Sep. 16, 2013.
NCBI Reference Sequence: XP_005613711.1, PREDICTED: mucin-3A-like [Equus caballus], Accession XP_005613711, Sep. 22, 2013.
NCBI Reference Sequence: WP_003501230.1, Hypothetical protein [Agrobacterium tumefaciens], Accession WP_003501230, May 12, 2013.
International Search Report for PCT/US14/61606 dated Apr. 23, 2015.

* cited by examiner

*Primary Examiner* — Julie Ha
(74) *Attorney, Agent, or Firm* — Heslin Rothenberg & Farley & Mesiti P.C.

(57) ABSTRACT

Disclosed are peptides that exhibit good binding to the anticodon stem and loop of human lysine tRNA species, tRNALys3. The starting point was the 15-amino-acid sequence, RVTHHAFLGAHRTVG, found to bind selectively to hypermodified tRNALys3. The peptide backbone conformation was determined via atomistic simulation of the peptide-ASLLys3complex and then held fixed throughout the search. Analysis of the binding structure and the various contributions to the binding energy shows that: 1) two hydrophilic residues (asparagine (ASN) at site 11 and the cysteine (CYS) at site 12) "recognize" the ASLLys3 due to the VDW energy, and thereby contribute to its binding specificity, and 2) the positively-charged arginines (ARG) at sites 4 and 13 preferentially attract the negatively-charged sugar rings and the phosphate linkages, and thereby contribute to the binding affinity.

12 Claims, 32 Drawing Sheets

Complex 2 (Case Two)

Complex 2 (Case Three)

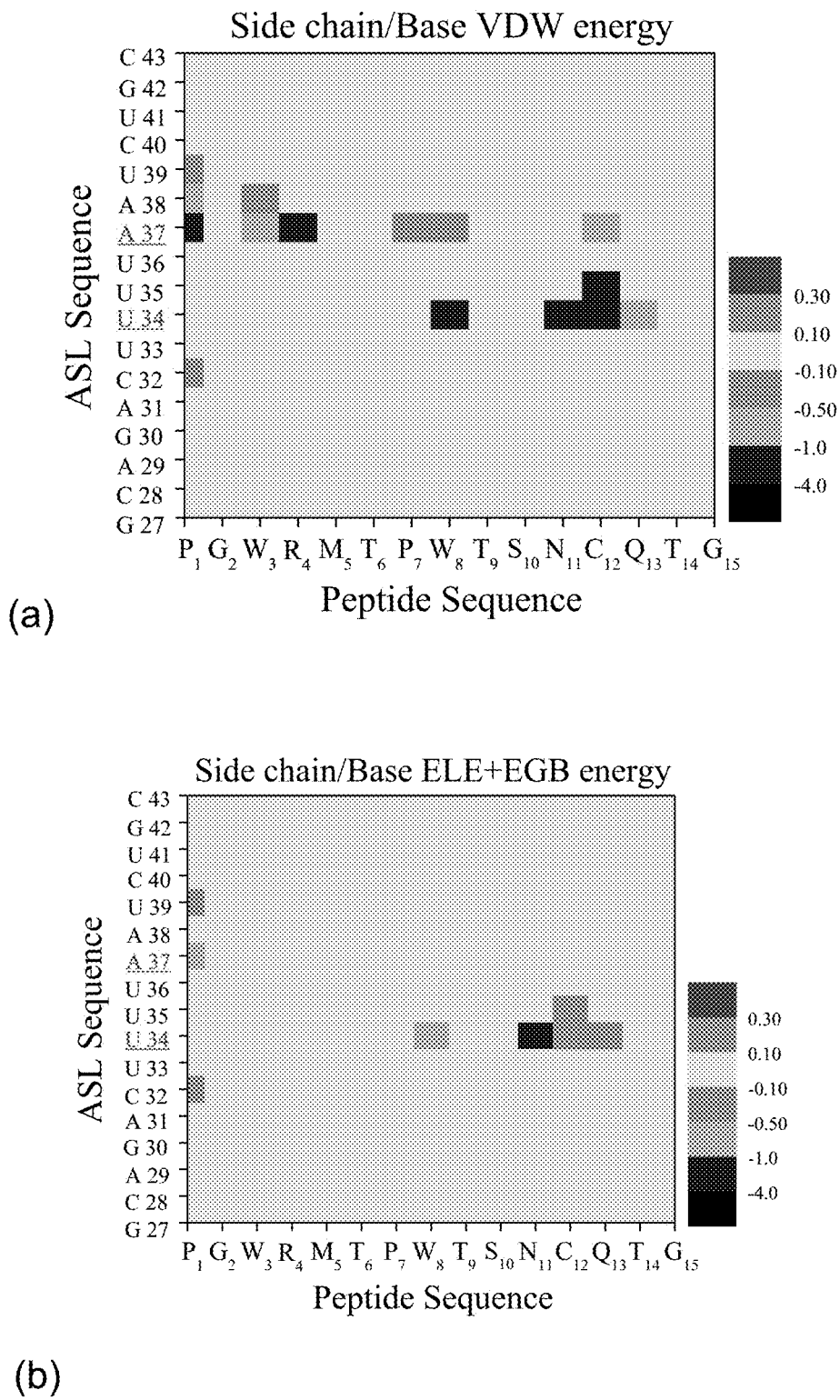
Figure 10a-b

SEQUENCE LISTING

<160> NUMBER OF SEQ ID NOS: 59

<210> SEQ ID NO 1
<211> LENGTH: 15
<212> TYPE: PRT
<213> ORGANISM: Artificial Sequence
<220> FEATURE:
<223> OTHER INFORMATION: synthetic peptide

<400> SEQUENCE: 1

Arg Gly Val Phe Ser His Pro His Thr Ala Val Pro Ser His Asn
1               5                   10                  15

-continued

```
<210> SEQ ID NO 2
<211> LENGTH: 15
<212> TYPE: PRT
<213> ORGANISM: Artificial Sequence
<220> FEATURE:
<223> OTHER INFORMATION: synthetic peptide

<400> SEQUENCE: 2

Arg Val Thr His His Ala Phe Leu Gly Ala His Arg Thr Val Gly
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: synthetic peptide

<400> SEQUENCE: 3

Arg Thr Leu His His Ala Leu Phe Gly Ala His Gln Thr Val Gly
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: synthetic peptide

<400> SEQUENCE: 4

Arg Trp Gln Met Thr Ala Phe Ala His Gly Trp Arg His Ser Gly
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: synthetic peptide

<400> SEQUENCE: 5

Arg Trp Asn His Cys Gln Phe Trp Asn Gly Trp Arg Ala Gln Gly
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: synthetic peptide

<400> SEQUENCE: 6

Arg Trp Asn His Cys Gln Phe Trp Asn Gly Trp Arg Ala Asn Gly
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: synthetic peptide

<400> SEQUENCE: 7

Arg Trp Asn His Gln Ser Phe Trp His Gly Trp Arg Ala Cys Gly
1               5                   10                  15
```

```
<210> SEQ ID NO 8
<211> LENGTH: 15
<212> TYPE: PRT
<213> ORGANISM: Artificial Sequence
<220> FEATURE:
<223> OTHER INFORMATION: synthetic peptide

<400> SEQUENCE: 8

Arg Trp Asn His Ser Gln Phe Trp Ser Leu Trp Arg Ala His Gly
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: synthetic peptide

<400> SEQUENCE: 9

Arg Trp Gln His His Ser Phe His Pro Leu Trp Arg Met Ser Gly
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: synthetic peptide

<400> SEQUENCE: 10

Arg Trp His His His His Phe Ser Pro Leu Trp Arg Trp His Gly
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: synthetic peptide

<400> SEQUENCE: 11

Arg His His His His His Phe Gly Pro Pro Trp Leu Asn Cys Gly
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: synthetic peptide

<400> SEQUENCE: 12

Arg His His His Ala Ser Phe Gly Pro Pro Trp Leu Ser His Gly
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: synthetic peptide

<400> SEQUENCE: 13

Arg His Ser His Ala His Phe Gly Pro Pro Trp Leu Ser His Gly
1               5                   10                  15
```

```
<210> SEQ ID NO 14
<211> LENGTH: 15
<212> TYPE: PRT
<213> ORGANISM: Artificial Sequence
<220> FEATURE:
<223> OTHER INFORMATION: synthetic peptide

<400> SEQUENCE: 14

Cys Trp Pro Arg Thr Ser Arg Ser Ser Gly Trp Leu Met Thr Gly
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: synthetic peptide

<400> SEQUENCE: 15

Cys Trp Pro Arg Ser Ser Arg Ser Ile Gly Trp Leu Ser Gln Gly
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: synthetic peptide

<400> SEQUENCE: 16

Cys Trp Pro Arg Ser Ser Arg Ser Thr Gly Trp Leu Thr Met Gly
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: synthetic peptide

<400> SEQUENCE: 17

Pro His Trp Arg Thr Thr Gly Trp Met Asn Asn Cys Arg Met Gly
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: synthetic peptide

<400> SEQUENCE: 18

Pro His Trp Arg Thr Asn Gly Trp Ile Asn Asn Cys Arg Leu Gly
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: synthetic peptide

<400> SEQUENCE: 19

Pro His Trp Arg Ser Thr Gly Trp Met Asn Asn Cys Arg Met Gly
1               5                   10                  15
```

```
<210> SEQ ID NO 20
<211> LENGTH: 15
<212> TYPE: PRT
<213> ORGANISM: Artificial Sequence
<220> FEATURE:
<223> OTHER INFORMATION: synthetic peptide

<400> SEQUENCE: 20

Val Ser Leu Arg Ser Asn Trp Trp Met Asn Asn Cys Arg Thr Gly
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: synthetic peptide

<400> SEQUENCE: 21

Val Leu Ser Arg Ser Asn Trp Trp Ile Asn Asn Cys Arg Gln Gly
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: synthetic peptide

<400> SEQUENCE: 22

Val Ser Leu Arg Ser Asn Trp Trp Met Asn Asn Cys Arg Gln Gly
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: synthetic peptide

<400> SEQUENCE: 23

Pro Gly Trp Arg Met Thr Pro Trp Thr Ser Asn Cys Gln Thr Gly
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: synthetic peptide

<400> SEQUENCE: 24

Pro Gly Trp Arg Val Thr Pro Trp Thr Ser Asn Cys Gln Thr Gly
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: synthetic peptide

<400> SEQUENCE: 25

Pro Gly Trp Arg Phe Thr Pro Trp Thr Ser Asn Cys Gln Thr Gly
1               5                   10                  15
```

```
<210> SEQ ID NO 26
<211> LENGTH: 15
<212> TYPE: PRT
<213> ORGANISM: Artificial Sequence
<220> FEATURE:
<223> OTHER INFORMATION: synthetic peptide

<400> SEQUENCE: 26

Pro Gly Met Met Thr Asn Arg Trp Thr Trp Asn Cys Gln Gly Arg
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: synthetic peptide

<400> SEQUENCE: 27

Pro Gly Met Met Ser Ser Arg Trp His Trp Asn Cys Gln Gly Arg
1               5                   10                  15

<210> SEQ ID NO 28
<211> LENGTH: 15
<212> TYPE: PRT
<213> ORGANISM: Artificial Sequence
<220> FEATURE:
<223> OTHER INFORMATION: synthetic peptide

<400> SEQUENCE: 28

Pro Gly Asn Met Ser Leu Arg Trp Ser Trp Asn Cys Gln Gly Arg
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: synthetic peptide

<400> SEQUENCE: 29

Pro Gly Met Met Thr Thr Arg Trp Thr Trp Asn Cys Gln Gly Arg
1               5                   10                  15

<210> SEQ ID NO 30
<211> LENGTH: 15
<212> TYPE: PRT
<213> ORGANISM: Artificial Sequence
<220> FEATURE:
<223> OTHER INFORMATION: synthetic peptide

<400> SEQUENCE: 30

Pro Gly Met Met Thr Thr Arg Trp Thr Trp Asn Cys Gln Gly Arg
1               5                   10                  15

<210> SEQ ID NO 31
<211> LENGTH: 15
<212> TYPE: PRT
<213> ORGANISM: Artificial Sequence
<220> FEATURE:
<223> OTHER INFORMATION: synthetic peptide

<400> SEQUENCE: 31

Pro Ile Gly Met Ser His Arg Trp Thr Trp Asn Cys Gln Gly Arg
1               5                   10                  15
```

```
<210> SEQ ID NO 32
<211> LENGTH: 28
<212> TYPE: PRT
<213> ORGANISM: Artificial Sequence
<220> FEATURE:
<223> OTHER INFORMATION: synthetic peptide
<220> FEATURE:
<221> NAME/KEY: Xaa
<222> LOCATION: (4)..(4)
<223> OTHER INFORMATION: Xaa is Thr or Ser
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: Xaa
<222> LOCATION: (9)..(9)
<223> OTHER INFORMATION: Xaa is Thr or Ser or Ile
<220> FEATURE:
<221> NAME/KEY: Xaa
<222> LOCATION: (13)..(13)
<223> OTHER INFORMATION: Xaa is Met or Ser or Thr
<220> FEATURE:
<221> NAME/KEY: Xaa
<222> LOCATION: (14)..(14)
<223> OTHER INFORMATION: Xaa is Thr or Gln or Met
<220> FEATURE:
<221> NAME/KEY: Xaa
<222> LOCATION: (18)..(18)
<223> OTHER INFORMATION: Xaa is Gln or Asn
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: Xaa
<222> LOCATION: (22)..(22)
<223> OTHER INFORMATION: Xaa is Ala or Val or Ile or Leu or Met or Phe
     or Tyr or Trp
<220> FEATURE:
<221> NAME/KEY: Xaa
<222> LOCATION: (22)..(22)
<223> OTHER INFORMATION: Xaa is a hydrophobic amino acid
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: Xaa
<222> LOCATION: (24)..(24)
<223> OTHER INFORMATION: Xaa is Gly or Ala
<220> FEATURE:
<221> NAME/KEY: misc_feature
<222> LOCATION: (27)..(27)
<223> OTHER INFORMATION: Xaa can be any naturally occurring amino acid

<400> SEQUENCE: 32

Cys Trp Pro Arg Xaa Ser Arg Ser Xaa Gly Trp Leu Xaa Xaa Gly Arg
1               5                   10                  15

Trp Xaa His Xaa Phe Xaa Xaa Xaa Trp Arg Xaa Gly
            20                  25

<210> SEQ ID NO 33
<211> LENGTH: 15
<212> TYPE: PRT
<213> ORGANISM: Artificial Sequence
<220> FEATURE:
<223> OTHER INFORMATION: synthetic peptide
<220> FEATURE:
<221> NAME/KEY: Xaa
<222> LOCATION: (5)..(5)
<223> OTHER INFORMATION: Xaa is Thr or Ser
<220> FEATURE:
<221> NAME/KEY: Xaa
<222> LOCATION: (6)..(6)
<223> OTHER INFORMATION: Xaa is Thr or Arg
```

<220> FEATURE:
<221> NAME/KEY: Xaa
<222> LOCATION: (9)..(9)
<223> OTHER INFORMATION: Xaa is Met or Thr or Ser
<220> FEATURE:
<221> NAME/KEY: Xaa
<222> LOCATION: (14)..(14)
<223> OTHER INFORMATION: Xaa is Met or Leu

<400> SEQUENCE: 33

Pro His Trp Arg Xaa Xaa Gly Trp Xaa Asn Asn Cys Arg Xaa Gly
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: synthetic peptide
<220> FEATURE:
<221> NAME/KEY: Xaa-Xaa
<222> LOCATION: (2)..(3)
<223> OTHER INFORMATION: Xaa-Xaa is Ser-Lys or Lys-Ser
<220> FEATURE:
<221> NAME/KEY: Xaa
<222> LOCATION: (9)..(9)
<223> OTHER INFORMATION: Xaa is Thr or Gln
<220> FEATURE:
<221> NAME/KEY: misc_feature
<222> LOCATION: (14)..(14)
<223> OTHER INFORMATION: Xaa can be any naturally occurring amino acid

<400> SEQUENCE: 34

Val Xaa Xaa Arg Ser Asn Trp Trp Xaa Asn Asn Cys Arg Xaa Gly
1               5                   10                  15

<210> SEQ ID NO 35
<211> LENGTH: 15
<212> TYPE: PRT
<213> ORGANISM: Artificial Sequence
<220> FEATURE:
<223> OTHER INFORMATION: synthetic peptide
<220> FEATURE:
<221> NAME/KEY: Xaa
<222> LOCATION: (5)..(5)
<223> OTHER INFORMATION: Xaa is Met or Val or Phe

<400> SEQUENCE: 35

Pro Gly Trp Arg Xaa Thr Pro Trp Thr Ser Asn Cys Gln Thr Gly
1               5                   10                  15

<210> SEQ ID NO 36
<211> LENGTH: 15
<212> TYPE: PRT
<213> ORGANISM: Artificial Sequence
<220> FEATURE:
<223> OTHER INFORMATION: synthetic peptide
<220> FEATURE:
<221> NAME/KEY: Xaa
<222> LOCATION: (2)..(2)
<223> OTHER INFORMATION: Xaa is Gly or Ile
<220> FEATURE:
<221> NAME/KEY: Xaa
<222> LOCATION: (3)..(3)
<223> OTHER INFORMATION: Xaa is Met or Arg or Gly
<220> FEATURE:
<221> NAME/KEY: Xaa
<222> LOCATION: (5)..(5)
<223> OTHER INFORMATION: Xaa is Thr or Ser
<220> FEATURE:
<221> NAME/KEY: Xaa
<222> LOCATION: (6)..(6)
<223> OTHER INFORMATION: Xaa is Asn or Ser or Leu or Thr or His

```
<220> FEATURE:
<221> NAME/KEY: Xaa
<222> LOCATION: (9)..(9)
<223> OTHER INFORMATION: Xaa is Thr or His or Ser

<400> SEQUENCE: 36

Pro Xaa Xaa Met Xaa Xaa Arg Trp Xaa Trp Asn Cys Gln Gly Arg
1               5                   10                  15

<210> SEQ ID NO 37
<211> LENGTH: 15
<212> TYPE: PRT
<213> ORGANISM: Artificial Sequence
<220> FEATURE:
<223> OTHER INFORMATION: synthetic peptide
<220> FEATURE:
<221> NAME/KEY: Xaa
<222> LOCATION: (4)..(4)
<223> OTHER INFORMATION: Xaa is Ile or Val or Met or Ser
<220> FEATURE:
<221> NAME/KEY: Xaa
<222> LOCATION: (5)..(5)
<223> OTHER INFORMATION: Xaa is Ser or Asn
<220> FEATURE:
<221> NAME/KEY: Xaa
<222> LOCATION: (6)..(6)
<223> OTHER INFORMATION: Xaa is Met or Phe or Asn
<220> FEATURE:
<221> NAME/KEY: Xaa
<222> LOCATION: (9)..(9)
<223> OTHER INFORMATION: Xaa is Thr or His or Ile
<220> FEATURE:
<221> NAME/KEY: Xaa
<222> LOCATION: (10)..(10)
<223> OTHER INFORMATION: Xaa is Ser or Asn or Thr or Met

<400> SEQUENCE: 37

Arg Gly Ser Xaa Xaa Xaa Arg Trp Xaa Xaa Asn Cys Gln Ile Tyr
1               5                   10                  15

<210> SEQ ID NO 38
<211> LENGTH: 15
<212> TYPE: PRT
<213> ORGANISM: Artificial Sequence
<220> FEATURE:
<223> OTHER INFORMATION: synthetic peptide
<220> FEATURE:
<221> NAME/KEY: Xaa
<222> LOCATION: (3)..(3)
<223> OTHER INFORMATION: Xaa is Gly or Thr or Gln
<220> FEATURE:
<221> NAME/KEY: Xaa
<222> LOCATION: (5)..(5)
<223> OTHER INFORMATION: Xaa is Ser or Thr or Gly
<220> FEATURE:
<221> NAME/KEY: Xaa
<222> LOCATION: (6)..(6)
<223> OTHER INFORMATION: Xaa is Ser or Gln or Thr
<220> FEATURE:
<221> NAME/KEY: Xaa
<222> LOCATION: (9)..(9)
<223> OTHER INFORMATION: Xaa is His or Ser or Thr or Gly
<220> FEATURE:
<221> NAME/KEY: Xaa
<222> LOCATION: (10)..(10)
<223> OTHER INFORMATION: Xaa is His or Pro
<220> FEATURE:
<221> NAME/KEY: Xaa
<222> LOCATION: (13)..(13)
<223> OTHER INFORMATION: Xaa is Gln or Pro
<220> FEATURE:
<221> NAME/KEY: Xaa
<222> LOCATION: (15)..(15)
<223> OTHER INFORMATION: Xaa is Pro or Gly or Asn
```

-continued

<400> SEQUENCE: 38

Pro Gly Xaa Met Xaa Xaa Arg Trp Xaa Xaa Asn Cys Xaa Trp Xaa
1               5                   10                  15

<210> SEQ ID NO 39
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: Xaa
<222> LOCATION: (3)..(3)
<223> OTHER INFORMATION: Xaa is Gln or Asn
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: Xaa
<222> LOCATION: (8)..(8)
<223> OTHER INFORMATION: Xaa is a hydrophobic amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: Xaa
<222> LOCATION: (10)..(10)
<223> OTHER INFORMATION: Xaa is Gly or Ala
<220> FEATURE:
<221> NAME/KEY: misc_feature
<222> LOCATION: (12)..(13)
<223> OTHER INFORMATION: Xaa can be any naturally occurring amino acid

<400> SEQUENCE: 39

Arg Trp Xaa His Xaa Xaa Phe Xaa Xaa Trp Arg Xaa Xaa Gly
1               5                   10

<210> SEQ ID NO 40
<211> LENGTH: 15
<212> TYPE: PRT
<213> ORGANISM: Artificial Sequence
<220> FEATURE:
<223> OTHER INFORMATION: synthetic peptide

<400> SEQUENCE: 40

Phe Ser Val Ser Phe Pro Ser Leu Pro Ala Pro Pro Asp Arg Ser
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: synthetic peptide

<400> SEQUENCE: 41

Arg Phe Gln His Ser Asn Trp Phe Ser Gly Trp Lys Val Asn Gly
1               5                   10                  15

<210> SEQ ID NO 42
<211> LENGTH: 15
<212> TYPE: PRT
<213> ORGANISM: Artificial Sequence
<220> FEATURE:
<223> OTHER INFORMATION: synthetic peptide

```
<400> SEQUENCE: 42

Arg Trp Asn His Cys Gln Phe Trp Ser Gly Trp Arg Ala Asn Gly
1               5                   10                  15

<210> SEQ ID NO 43
<211> LENGTH: 15
<212> TYPE: PRT
<213> ORGANISM: Artificial Sequence
<220> FEATURE:
<223> OTHER INFORMATION: synthetic peptide

<400> SEQUENCE: 43

Arg Trp Asn Gly Ser Gln Trp Phe Cys Ala Trp Arg Ala Asn Gly
1               5                   10                  15

<210> SEQ ID NO 44
<211> LENGTH: 15
<212> TYPE: PRT
<213> ORGANISM: Artificial Sequence
<220> FEATURE:
<223> OTHER INFORMATION: synthetic peptide

<400> SEQUENCE: 44

Arg His Thr His Cys Ala Phe Trp Gly Ala His Arg Thr Val Gly
1               5                   10                  15

<210> SEQ ID NO 45
<211> LENGTH: 15
<212> TYPE: PRT
<213> ORGANISM: Artificial Sequence
<220> FEATURE:
<223> OTHER INFORMATION: synthetic peptide

<400> SEQUENCE: 45

Arg Trp Thr His Cys Gln Phe Trp Gln Gly Phe Arg Val Asn Gly
1               5                   10                  15

<210> SEQ ID NO 46
<211> LENGTH: 15
<212> TYPE: PRT
<213> ORGANISM: Artificial Sequence
<220> FEATURE:
<223> OTHER INFORMATION: synthetic peptide

<400> SEQUENCE: 46

Phe Ser Val Ser Phe Pro Ser Leu Pro Ala Pro Pro Asp Arg Ser
1               5                   10                  15

<210> SEQ ID NO 47
<211> LENGTH: 15
<212> TYPE: PRT
<213> ORGANISM: Artificial Sequence
<220> FEATURE:
<223> OTHER INFORMATION: synthetic peptide

<400> SEQUENCE: 47

Thr Trp Ala Lys Gln Lys Gly Tyr Val Ser Cys Asn Asn Val Gly
1               5                   10                  15

<210> SEQ ID NO 48
<211> LENGTH: 15
<212> TYPE: PRT
<213> ORGANISM: Artificial Sequence
<220> FEATURE:
<223> OTHER INFORMATION: synthetic peptide
```

```
<400> SEQUENCE: 48

Arg Gly Ser Ile Ser Met Arg Trp Thr Ser Asn Cys Gln Ile Tyr
1               5                   10                  15

<210> SEQ ID NO 49
<211> LENGTH: 15
<212> TYPE: PRT
<213> ORGANISM: Artificial Sequence
<220> FEATURE:
<223> OTHER INFORMATION: synthetic peptide

<400> SEQUENCE: 49

Arg Gly Ser Val Asn Met Arg Trp Thr Asn Asn Cys Gln Ile Tyr
1               5                   10                  15

<210> SEQ ID NO 50
<211> LENGTH: 15
<212> TYPE: PRT
<213> ORGANISM: Artificial Sequence
<220> FEATURE:
<223> OTHER INFORMATION: synthetic peptide

<400> SEQUENCE: 50

Arg Gly Ser Met Ser Phe Arg Trp His Thr Asn Cys Gln Ile Tyr
1               5                   10                  15

<210> SEQ ID NO 51
<211> LENGTH: 15
<212> TYPE: PRT
<213> ORGANISM: Artificial Sequence
<220> FEATURE:
<223> OTHER INFORMATION: synthetic peptide

<400> SEQUENCE: 51

Arg Gly Ser Ile Ser Met Arg Trp Thr Asn Asn Cys Gln Ile Tyr
1               5                   10                  15

<210> SEQ ID NO 52
<211> LENGTH: 15
<212> TYPE: PRT
<213> ORGANISM: Artificial Sequence
<220> FEATURE:
<223> OTHER INFORMATION: synthetic peptide

<400> SEQUENCE: 52

Arg Gly Ser Ser Ser Asn Arg Trp Ile Met Asn Cys Gln Ile Tyr
1               5                   10                  15

<210> SEQ ID NO 53
<211> LENGTH: 15
<212> TYPE: PRT
<213> ORGANISM: Artificial Sequence
<220> FEATURE:
<223> OTHER INFORMATION: synthetic peptide

<400> SEQUENCE: 53

Ser Ser Ala Arg Tyr Thr Phe Val Arg Ser His Thr Met Phe Gly
1               5                   10                  15

<210> SEQ ID NO 54
<211> LENGTH: 15
<212> TYPE: PRT
<213> ORGANISM: Artificial Sequence
<220> FEATURE:
<223> OTHER INFORMATION: synthetic peptide
```

```
<400> SEQUENCE: 54

Pro Gly Gly Met Ser Ser Arg Trp His His Asn Cys Gln Trp Pro
1               5                   10                  15

<210> SEQ ID NO 55
<211> LENGTH: 15
<212> TYPE: PRT
<213> ORGANISM: Artificial Sequence
<220> FEATURE:
<223> OTHER INFORMATION: synthetic peptide

<400> SEQUENCE: 55

Pro Gly Gly Met Thr Gln Arg Trp Ser His Asn Cys Gln Trp Pro
1               5                   10                  15

<210> SEQ ID NO 56
<211> LENGTH: 15
<212> TYPE: PRT
<213> ORGANISM: Artificial Sequence
<220> FEATURE:
<223> OTHER INFORMATION: synthetic peptide

<400> SEQUENCE: 56

Pro Gly Thr Met Thr Thr Arg Trp Thr His Asn Cys Pro Trp Gly
1               5                   10                  15

<210> SEQ ID NO 57
<211> LENGTH: 15
<212> TYPE: PRT
<213> ORGANISM: Artificial Sequence
<220> FEATURE:
<223> OTHER INFORMATION: synthetic peptide

<400> SEQUENCE: 57

Pro Gly Gln Met Ser Thr Arg Trp Gly Pro Asn Cys Gln Trp Asn
1               5                   10                  15

<210> SEQ ID NO 58
<211> LENGTH: 15
<212> TYPE: PRT
<213> ORGANISM: Artificial Sequence
<220> FEATURE:
<223> OTHER INFORMATION: synthetic peptide

<400> SEQUENCE: 58

Pro Gly Thr Met Gly Gln Arg Trp Ser His Asn Cys Gln Trp Pro
1               5                   10                  15

<210> SEQ ID NO 59
<211> LENGTH: 15
<212> TYPE: PRT
<213> ORGANISM: Artificial Sequence
<220> FEATURE:
<223> OTHER INFORMATION: synthetic peptide

<400> SEQUENCE: 59

Pro Pro Thr Thr Phe Ser Gly Lys Gln Ser Ala Thr Met Tyr Gly
1               5                   10                  15
```

PEPTIDE INHIBITOR OF HIV REVERSE TRANSCRIPTION

CROSS REFERENCE TO RELATED APPLICATIONS

This application is a national phase filing under 35 U.S.C. § 371 of PCT International Application No. PCT/US2014/061606, filed on Oct. 21, 2014, which claims priority to U.S. Provisional application No. 61/893,600 filed on Oct. 21, 2013; the contents of both are incorporated by reference in their entirety into the present application.

STATEMENT REGARDING FEDERALLY-SPONSORED RESEARCH OR DEVELOPMENT

This invention was made with government support under grant GM023037 awarded by the National Institutes of Health and grant CBET0835794 awarded by the National Science Foundation. The government has certain rights in the invention.

STATEMENT OF RIGHTS UNDER FEDERALLY-SPONSORED RESEARCH

This invention was made with government support under grant P30 CA008748 awarded by the U.S. National Institutes of Health. The government has certain rights in the invention.

SEQUENCE LISTING

The instant application contains a Sequence Listing, created on Nov. 27, 2017; the file, in ASCII format, is designated 0794148A_ST25.txt and is 17.9 KB in size. The file is hereby incorporated by reference in its entirety into the instant application.

BACKGROUND OF THE INVENTION

Since the 1980's when the human immunodeficiency virus (HIV) was discovered, 30 million people have died, making HIV the 6th leading cause of death in the world. If untreated, HIV infection eventually causes acquired immune deficiency syndrome (AIDS) a serious insult to the human immune system. So far, the treatments of choice for HIV/AIDS are antiretroviral drug therapies, but they are treatments rather than cures in that the HIV virus still remains in the body. Work on developing effective therapies that suppress the replication of HIV and hence cure the disease is ongoing. Interruption in any one of the steps in the HIV life cycle has the possibility to stop replication, the process by which viruses use the host cell to make new copies of themselves. A promising target is $tRNA^{Lys3}$, the primer of reverse transcriptase that is recruited by the HIV-1 virus during virus RNA replication. Different from other tRNA, $tRNA^{Lys3}$ has chemically-rich posttranscriptional modifications in the anticodon stem and loop (ASL) domain—one is 5-methylmethoxymethyl-2-thiouridine ($mcm^5s^2U34$) at position 34, and another 2-methylthio-$N^6$-threonylcarbamoyladenosine ($ms^2t^6A_{37}$) at position 37. Blocking the recruitment of $tRNA^{Lys3}$ has the potential to interfere with the HIV life cycle, causing the death of the virus.

A variety of candidate peptide sequences that mimic the binding behavior of nucleocapside proteins in the body were synthesized and then tested for their capability to bind the anticodon stem and loop (ASL) of $tRNA^{Lys3}$. Twenty different peptide sequences containing 15 or 16 amino acids were chosen from Peptide Phage Display Libraries and fluorescence and circular dichroism spectroscopy was used to characterize the peptide binding to these ASLs. The best peptide sequence—RGVFSHPHTAVPSHN (SEQ ID NO:1) exhibited a relatively high binding affinity for hypermodified $ASL^{Lys3}$, but bound poorly to singly modified $ASL^{Lys3}$, the ASLs of the two other human $tRNA^{Lys}$ species, $AsL^{Lys1, 2}$ and Escherichia coli $ASL^{Glu}$ and $ASL^{Val}$.

Other research groups have also investigated the binding behavior of RNA and proteins. Xia et al. used a combination of fluorescence up-conversion and transient absorption techniques to study the mechanisms and dynamical processes associated with RNA-protein recognition. They found that the complex formed by the antiterminator N protein and the stem-loop RNA hairpin exists in a dynamical two-state equilibrium between stacked and unstacked conformations. Formation of the stacked structure was driven by hydrophobic interactions (rather than by charge-charge interactions) between the residue at site 14 of their peptide chain and the ribose on RNA. In related work, Zhang et al. utilized site-directed spin labeling to examine the distribution of conformations at the interface between a peptide of 22 amino acids and a stem-loop RNA element. They observed that the C-terminal fragment of the bound peptide tends to adopt multiple discrete conformations within the complex.

SUMMARY OF THE INVENTION

The present invention relates to short multi-functional peptide chains that bind to $tRNA^{Lys3}$. The peptides are useful for interrupting the assembly and budding of viral RNA and associated proteins.

In one aspect, the invention relates to a peptide selected from:
(a) C-W-P-R-Xaa1-S-R-S-Xaa2-G-W-L-Xaa3-Xaa4-G-R-W-Q/N-H-Xaa-F-Pho-X-G/A-W-R-Xaa-G wherein
  Xaa1 is threonine or serine;
  Xaa2 is threonine, serine, or isoleucine;
  Xaa3 is methionine, serine or threonine; and
  Xaa4 is threonine, glutamine or methionine (SEQ ID NO:32);
(b) P-H-W-R-Xaa1'-Xaa2'-G-W-Xaa3'-N-N-C-R-Xaa4'-G wherein
  Xaa1' is threonine or serine;
  Xaa2' is threonine or arginine;
  Xaa3' is methionine, serine or threonine; and
  Xaa4' is methionine or leucine (SEQ ID NO:33);
(c) V-Xaa1-Xaa2-R-S-N-W-W-Xaa3-N-N-C-R-Xaa4-G wherein
  Xaa1-Xaa2 is serine-lysine or lysine-serine;
  Xaa3 is methionine or isoleucine; and
  Xaa4 is threonine or glutamine (SEQ ID NO:34);
(d) P-G-W-R-Xaa1-T-P-W-T-S-N-C-Q-T-G wherein
  Xaa1 is methionine, valine or phenylalanine (SEQ ID NO:35);
(e) P-Xaa1-Xaa2-M-Xaa3-Xaa4-R-W-Xaa5-W-N-C-Q-G-R wherein
  Xaa1 is glycine or isoleucine;
  Xaa2 is methionine, arginine or glycine;
  Xaa3 is threonine or serine;
  Xaa4 is asparagine, serine, leucine, threonine, histidine;
  Xaa5 is threonine, histidine or serine (SEQ ID NO:36);
(f) R-G-S-Xaa1-Xaa2-Xaa3-R-W-Xaa4-Xaa5-N-C-Q-I-Y wherein
  Xaa1 is isoleucine, valine, methionine or serine;
  Xaa2 is serine or asparagine;
  Xaa3 is methionine, phenylalanine or asparagine;
  Xaa4 is threonine, histidine or isoleucine;

Xaa5 is serine, asparagine, threonine or methionine (SEQ ID NO:37); or (g) P-G-Xaa1-M-Xaa2-Xaa3-R-W-Xaa4-Xaa5-N-C-Xaa6-W-Xaa7 wherein Xaa1 is glycine, threonine or glutamine;
Xaa2 is serine, threonine or glycine;
Xaa3 is serine, glutamine or threonine;
Xaa4 is histidine, serine, threonine or glycine;
Xaa5 is histidine or proline;
Xaa6 is glutamine or proline;
Xaa7 is proline, glycine or asparagine (SEQ ID NO:38).

In another aspect, the invention relates to a peptide with the amino acid sequence:

R-W-Q/N-H-X-X-F-PHO-X-G/A-W-R-X-X-G where X is any amino acid, Pho is a hydrophobic amino acid; position 3 is either Q or N and position 10 is either G or A (SEQ ID NO:39).

The peptides of the invention bind to the anticodon and stem loop (ASL) of tRNA$^{Lys3}$.

In one aspect, the invention relates to a peptide comprising the amino acid sequence RVTHHAFLGAHRTVG (SEQ ID NO:2) that has good binding capability to the anticodon stem and loop (ASL) of human lysine tRNA species, tRNA$^{Lys3}$.

In one aspect, the invention relates to the use of such peptides to inhibit reverse transcription and ultimately the assembly and budding of HIV.

BRIEF DESCRIPTION OF THE DRAWINGS

FIGS. 10a-d shows a map of the contributions to the binding energy for interactions between the nucleotides on ASL and the side chains on the peptide for Case Three. (a) VDW energy and (b) ELE+EGB energy involving the side chain of peptide and the base of ASLLys3; (c) VDW energy and (d) ELE+EGB energy involving the side chain of peptide and the sugar ring and phosphate linkage of ASLLys3. The x-axis represents the residue sequence along the peptide chain, the y-axis represents the nucleotide sequence along ASL and the color bar on the right scales the value of the energies.

DETAILED DESCRIPTION OF THE INVENTION

Figure 1:
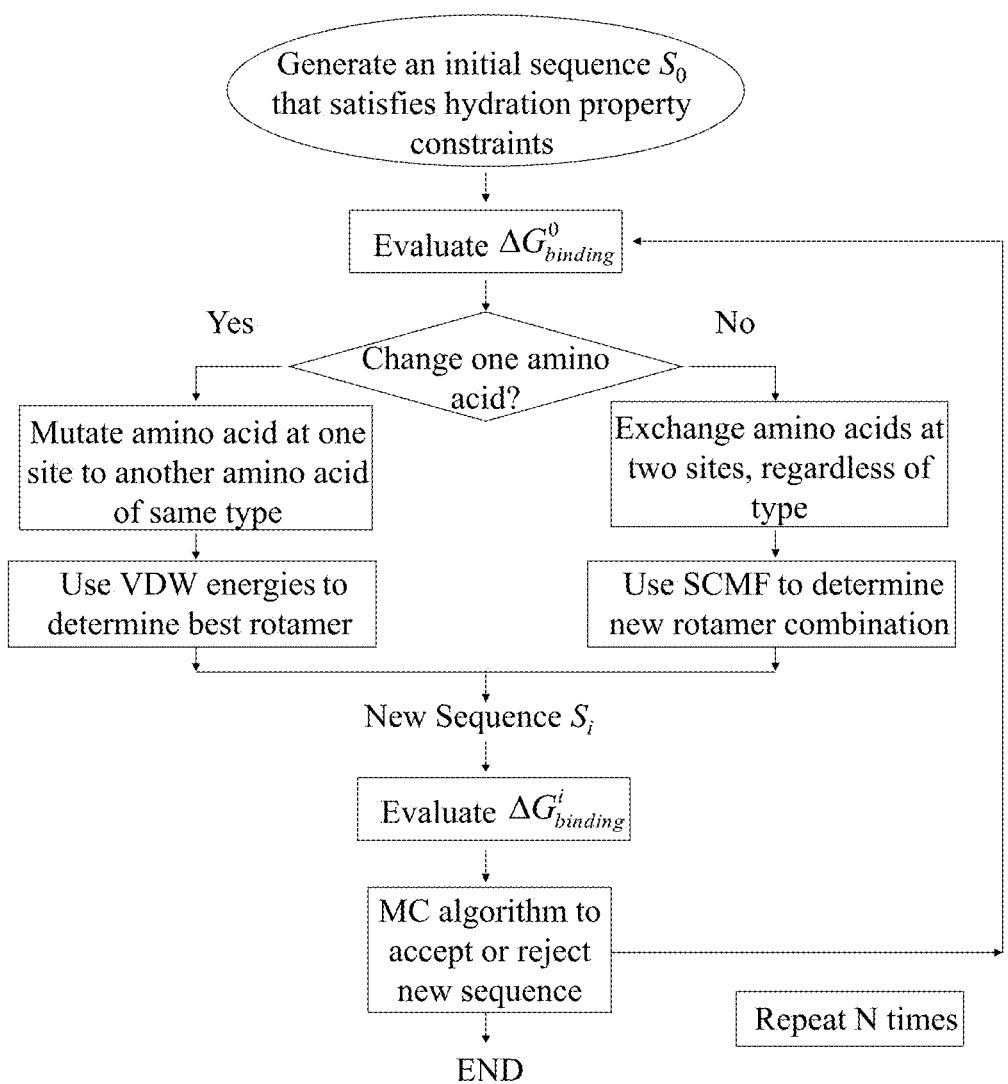
FIG. 1 is a flow chart showing the steps of the search algorithm.

All publications, patents and other references cited herein are incorporated by reference in their entirety into the present disclosure.

In practicing the present invention, many conventional techniques in protein chemistry and peptide synthesis are used, which are within the skill of the art. These techniques are described in greater detail in, for example, *Solid Phase Peptide Synthesis* by John Morrow Stewart and Martin et al. *Application of Almez-mediated Amidation Reactions to Solution Phase Peptide Synthesis*, Tetrahedron Letters Vol. 39, pages 1517-1520 1998.) The contents of these references and other references containing standard protocols, widely known to and relied upon by those of skill in the art, including manufacturers' instructions and techniques described in the references cited herein are hereby incorporated by reference as part of the present disclosure.

Methods for protein structure analysis and protein design are known in the art and details regarding known techniques used in practicing the invention can be found, for example in references cited herein including:

*Monte Carlo procedure for protein design.* (A. Irbäck, C. Peterson, F. Potthast, and E. Sandelin. *Phys. Rev. E,* 1998, 58: 5249-5252.);

*Application of a Self-consistent Mean Field Theory to Predict Protein Side-chains Conformation and Estimate Their Conformational Entropy.* (P. Koehl, and M. Delarue. *J. Mol. Biol.,* 1994, 239: 249-275); and

*Polypeptide Folding Using Monte Carlo Sampling, Concerted Rotation, and Continuum Solvation.* (J. P. Ulmschneider and W. L. Jorgensen. *J. Am. Chem. Soc.,* 2004, 126: 1849-1857).

Methods for peptide synthesis are also known in the art. Because of their relatively small size, the peptides of the invention may be directly synthesized in solution or on a solid support in accordance with conventional techniques. Various automatic synthesizers are commercially available and can be used in accordance with known protocols.

The synthesis of peptides in solution phase has become a well-established procedure for large scale production of synthetic peptides and as such is a suitable alternative method for preparing the peptides of the invention. (See for example, *Solid Phase Peptide Synthesis* by John Morrow Stewart and Martin et al. *Application of Almez-mediated Amidation Reactions to Solution Phase Peptide Synthesis,* Tetrahedron Letters Vol. 39, pages 1517-1520 1998.)

The current invention is the result of efforts to discover inhibitors that can break the reverse transcription of HIV. A search algorithm was developed to design peptide chains that recognize the primer $ASL^{Lys3}$ with a higher affinity and specificity than viral RNA. The starting point was a 15-amino-acid sequence—RVTHHAFLGAHRTVG (SEQ ID NO:2)—found experimentally by Agris et al. to bind selectively to hypermodified $tRNA^{Lys3}$. Using the new search algorithm that mutates this peptide sequence to improve its binding affinity and specificity to $ASL^{Lys3}$, a number of peptides were identified.

tRNA Isoacceptor $htRNA^{Lys3}{}_{UUU}$

There are three human isoaccepting tRNAs for the amino acid lysine, $htRNA^{Lys1,2,3}$. The three human tRNALys decode the two lysine codons, AAA and AAG. Two of the isoacceptors, $htRNA^{Lys1,2}{}_{CUU}$ with the anticodon CUU, decode AAG. But only one, $htRNA^{Lys3}{}_{UUU}$ with the anticodon UUU, responds to the cognate codon AAA and wobbles to AAG. Besides its important role in protein synthesis, $htRNA^{Lys3}{}_{UUU}$ serves as the primer of reverse transcription in the replication of the lentiviruses, including Human Immunodeficiency Virus type 1 (HIV-1). During the replication of HIV-1, the host cell $htRNA^{Lys3}{}_{UUU}$ is recognized and bound, and its structure destabilized by nucleocapsid protein 7 (NCp7). This destabilization allows the relaxed U-rich anticodon stem loop ($hASL^{Lys3}{}_{UUU}$), as well as the acceptor stem, to be annealed to the HIV viral RNA. During the subsequent infection, $htRNA^{Lys3}{}_{UUU}$ is the primer for HIV reverse transcriptase.

$htRNA^{Lys3}{}_{UUU}$ is one of the most uniquely processed tRNAs having chemically rich post-transcriptional modifications that are important to conformation and function of the tRNA during protein synthesis. Until recently the role(s) these modifications play in the tRNA's interaction with NCp7 and in viral replication were not known. The naturally occurring modifications, 5-methoxycarbonylmethyl-2-thiouridine (mcm5s2U34), at tRNA's wobble position-34, 2-methylthio-N6-threonylcarbamoyladenosine (ms2t6A37)

at position-37, 3'-adjacent to the anticodon in the loop of the hASL$^{Lys3}_{UUU}$ are both chemically rich and constitute a unique combination in human tRNAs. These modifications enhance NCp7's ability to recognize and bind to the RNA, suggesting that these modifications are an important discrimination factor for recognition by NCp7. The presence of these modifications increases NCp7 affinity for hASLLys3 almost 10-fold (Kd=0.28±0.03 µM for modified and Kd=2.30±0.62 µM for unmodified ASL) (9). NCp7 is critical to HIV replication because it binds and relaxes the htRNALys3 structure, facilitating annealing of the tRNA to the viral genomic RNA and packaging of the genomic RNA into the viral capsid.

Fifteen- and sixteen-amino acid peptides were selected to mimic NCp7's preferential recognition of the fully modified hASL$^{Lys3}_{UUU}$. These peptides can be used to study modification-dependent protein recognition of RNAs, and specifically recognition and annealing of htRNA$^{Lys3}_{UUU}$ to the HIV viral RNA. One peptide, P6 (sequence RVTHHAFL-GAHRTVG, SEQ ID NO:2), was also shown to mimic NCp7 by not only binding hASL$^{Lys3}_{UUU}$ but also through destabilizing the ASL structure. The ability of peptides to mimic NCp7 makes it possible to engineer a peptide with a signature amino acid sequence that can be used as a tool in future studies of protein recognition of RNAs, particularly those with unique modifications chemistries. Herein, we report the development of a signature amino acid sequence for recognition of htRNA$^{Lys3}_{UUU}$. An algorithm was developed that optimizes the amino acid sequence by combining self-consistent mean field (SCMF) and Monte Carlo (MC) approaches. The resulting peptides were then validated as binders with high affinity and selectivity in vitro. The peptide sequences predicted by the algorithms preferentially bound the modified hASL$^{Lys3}_{UUU}$ with affinities at or higher than P6, and with greater specificity. The signature sequence provides insight into peptide and protein recognition of the modified tRNA$^{Lys3}_{UUU}$.

The primary goal of this study was to demonstrate that a signature amino acid sequence can be identified as binding a uniquely modified RNA with high affinity and specificity. We reached this signature sequence using a combination of computational simulations to obtain optimized amino acid sequences that were then confirmed by binding studies in vitro. By comparing peptide sequences which specifically bound the modified hASL$^{Lys3}_{UUU}$ to those which did not, we were able to derive an amino acid signature that should be useful for protein/peptide recognition of RNA with modifications. Focusing primarily on those peptides which showed the highest affinity and specificity for the modified hASL$^{Lys3}_{UUU}$, the amino acid signature emerged R-W-Q/N-H-X-X-F-Pho-X-G/A-W-R-X-X-G (where X can be most amino acids and Pho is hydrophobic, SEQ ID NO:39) (Table 10).

The evolution of peptide sequences in silico is rapid relative to screening at the bench. Ideally, we have developed an algorithm to simulate binding events of every 15-amino acid peptide combination (>3.3×1023) to each substrate. In our algorithm, all 20 amino acids are considered. However, we group them for the purpose of describing their hydration properties. There are concessions such as grouping the amino acids by side chain properties to more quickly move through peptide evolution. Our developed algorithm proved to be a powerful tool in accurately predicting peptides which would bind specifically to hASL$^{Lys3}_{UUU}$ modifications. We believe that we can improve the accuracy of in silico predictions by developing simulations in tandem to look more closely at non-specific binding of the peptide to other small RNAs and/or unmodified tRNAs or ASLs. A cross-check performed by a parallel screen assessing binding energies of peptides binding to different ASLs could potentially eliminate nearly all false positives before moving to in vitro and/or in vivo experiments. The validation screens in vitro revealed that while the computer algorithms were not 100% correct in predicting peptide sequences with both high affinity and specificity, the selection in silico was a serious tool for predicting binding trends and quickly screening through many peptide sequence combinations.

Figure 5A:
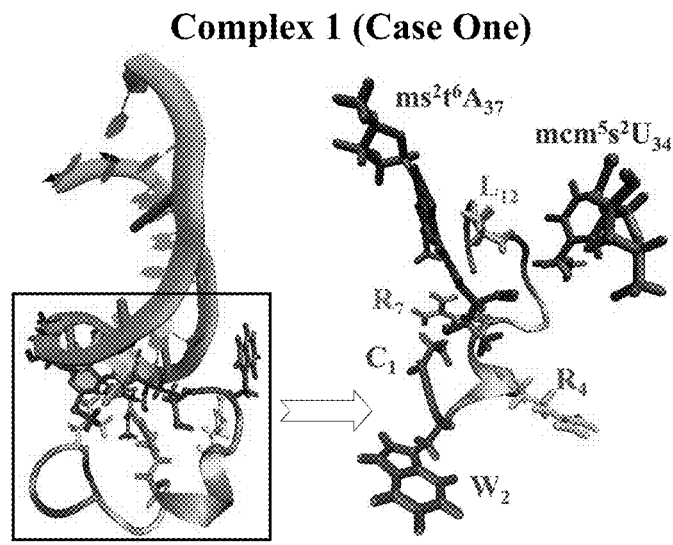
FIGS. 5a-d are snapshots of the structure of (a) Complex 1 and (c) Complex 2. The various contributions to the binding energy along the sequence of the peptide chain for (b) Complex 1 and (d) Complex 2. The ASLLys$^3$ is represented by the green ribbon; the peptide sequences are represented by the multi-colored ribbons. Several key amino acids and nucleotides are specified in distinct colors.
Figure 5B:
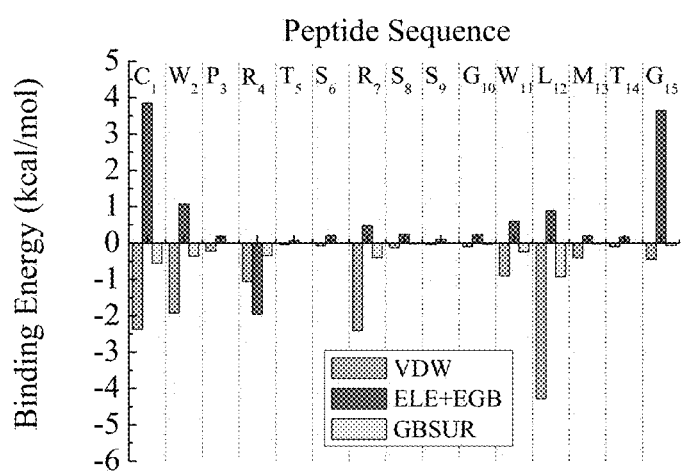

The derived amino acid signature offers clues and surprises as to why the optimized peptides from Case 1 and 2 bind the modified hASL$^{Lys3}$ with high affinity. Interestingly, the 5'-amino terminal sequence is more hydrophilic (R, Q, H) than the center (F, Pho) or the 3'-carboxyl terminus (G). Conventional thought would have the two positively charged arginine residues (positions 1 and 12) preferentially engaged with the negatively charged phosphate linkages via charge-charge interactions and/or the hydrophilic sugars. Here, the two arginine residues are also involved in interactions with the mcm5s2U34 and ms2t6A37 due to VDW energy (FIG. 5B). The increased number of hydrophobic residues, specifically tryptophan (position 11) and phenylalanine (position 7) contribute to the overall binding specificity through VDW interactions.

One would expect that the phenyl-ring of phenylalanine would intercalate within the 3'-base stack of the anticodon domain. The N6-threonylcarbamoyl-group of ms2t6A37 is known to enhance base stacking. Phenylalanine has been observed to intercalate between anticodon nucleosides of tRNALys in the co-crystal structure of lysyl-tRNA synthetase and tRNALys. However, instead of the expected intercalation, F7 interacts with the threonyl-side chain contributing to the affinity and specificity of the peptide (FIG. 5B). Though the signature sequence and the selected peptide sequences, P27 and P31 that have the highest affinity and specificity for the modified hASL$^{Lys3}_{UUU}$ have two arginines each, there is little sequence homology with RNA binding proteins that are rich in arginine or with single-stranded RNA binding proteins.

The optimization of RNA-binding peptides to recognize the unique chemistries of modified nucleosides and the contributions they make to local structure affords the opportunity of inhibiting RNA-binding proteins studied in vitro, and possibly in vivo. The benefits of modification-dependent signature peptides are many-fold. First, an amino acid signature peptide that uniquely recognizes a specific RNA modification or combination of modifications becomes a tool in the study of RNA-binding proteins that interact with RNA in a modification-dependent manner. Modifications are most often found in the terminal and internal loops of RNA structures. There the modifications negate intra-loop hydrogen bonding and can enhance or even decrease the possibility of base stacking (32). Peptides that recognize the ubiquitous anticodon domain modification N6-threonylcarbamoyladenosine can be used as a tool to study other modified tRNA-protein interactions, for instance those between tRNAs and their modification enzymes and/or am inoacyl-tRNA synthetases.

Previous studies demonstrated the feasibility of selecting peptides with modification-dependent recognition of tRNAs' anticodon stem and loop domains, ASLs. The peptides were selected from completely and partially randomized phage display libraries. However, optimizing 15- and 16-amino acid peptide sequences using this approach is not feasible since there are over 3.3×1023 possible sequences. Due to the exorbitantly high costs of creating and screening millions of peptides even with the benefit of phage display, we turned to computer algorithms and Assisted Model Building with Energy Refinement, AMBER, simulations to pare down the number of possibilities before performing in vitro assays. We developed a novel optimization strategy that combines MC with SCMF to evolve amino acid sequences. The peptide P6 sequence RVTH-HAFLGAHRTVG (SEQ ID NO:2) was the starting point from which an optimized peptide was sought to bind the modified $hASL^{Lys3}_{UUU}$ with the highest specificity and affinity. The ability to design specific multifunctional proteins on the computer has improved enormously in recent years as computational design algorithms have matured and the protein database has expanded. Computational design can be used to systematically evaluate the merits of different candidate sequences and to analyze the consequences of sequence perturbation when experimental validation is difficult or time consuming. Generally, the basic search algorithms used today include: dead-end elimination (DEE), self-consistent mean field (SCMF), Monte Carlo (MC) and genetic algorithms (GA). The first two algorithms are deterministic; if they are able to converge, they are guaranteed to find the global minimum energy configuration (GMEC). The latter two are stochastic, which means their solution may not be the GMEC.

A quantitative comparison between the four search algorithms described above was conducted by Voigt et al., who found that DEE is the fastest search algorithm if it can find the GMEC, but it sometimes fails to do so; SCMF and MC are comparable in accuracy and speed for small systems. MC is easy to extend to large system, but SCMF is not. Based on a MC procedure and a set of score functions, the Rosetta program developed by Baker and coworkers is most often used to design the protein sequences so that they can strengthen the stability of a crystal structure on a fixed backbone scaffold of protein. Kuhlman et al. used the Rosetta program to design sequences that would be consistent with the crystal structures of 108 native proteins. They found remarkably that more than 51% of the core residues and 27% of all residues in their redesigned sequences were identical to the amino acids in the corresponding sites in the native proteins. In addition, the Rosetta program is used widely to study protein-protein docking and receptor-ligand binding by proteins with a fixed sequence. For example, Chaudhury and Gray used four different binding methods in RosettaDock to predict the structures of docked protein complexes and then compared them with those taken from the PDB.

In this project, the focus is on de novo design of a sequence of residues on a peptide chain so as to improve the peptide's binding capability, thereby increasing its potential to prevent the HIV replication cycle. We developed a new search algorithm combining MC and SCMF to design a short peptide sequence that has good binding with the anticodon stem and loop ($ASL^{Lys3}$) of $tRNA^{Lys3}$. In this search algorithm, there are two types of trial "moves" used to evolve towards the best peptide sequence: one is the substitution of one amino acid; another is the exchange of two amino acids. The binding free energy of the new sequences generated by the trial "moves" is evaluated, and then accepted or rejected according to the MC technique based on the Metropolis algorithm. Firstly, we investigate how the initial binding configuration affects the evolution of sequences as the search algorithm progresses. Then, we perform searches on sequences that are constrained to have three different sets of hydration properties by adjusting the number of amino acids of each type (hydrophobic, polar, charged, etc) along the chain. Once the best peptide binders have been found, we analyze which types of interactions are responsible for the binding behavior, focusing in particular on binding affinity (the ability to stabilize the binding complex) and binding specificity (the ability to recognize the binding receptor).

In one embodiment, a novel search algorithm combining Monte Carlo (MC) and self-consistent mean field (SCMF) was developed which allows a peptide sequence to be evolved very quickly. When analyzing the energy contributions of the peptide sequences in the search algorithm, we found that two hydrophilic residues (Asparagine at site 11 and Cysteine at site 12) "recognize" the $ASL^{Lys3}$ due to the van der Waals (VDW) energy, and contribute to its binding specificity. The "binding affinity" is due to the charge-charge interaction between the positively charged arginines at sites 4 and 13 and the sugar rings/phosphate linkages which are themselves negatively charged.

Here, the search algorithms are described in detail. This is followed by a comparison of the evolution results based on the different initial binding configurations and a description of the best peptide sequences obtained by implementing the search algorithm. Subsequently, an analysis of the structure and contributions to the free energy of the $ASL^{Lys3}$-peptide complex is presented.

In this embodiment, a search algorithm was developed to design short peptides that bind to the anticodon stem and loop ($ASL^{Lys3}$) of $tRNA^{Lys3}$ using a combination of self-consistent mean field (SCMF) and Monte Carlo (MC) techniques. FIG. 1 shows a flow chart that illustrates the steps in the algorithm. During the search process, there are two types of trial "moves". In the first type of trial "move", a new randomly-chosen amino acid is substituted for an existing (old) randomly-chosen amino acid along the backbone of a peptide chain. The new amino acid must be of the same residue "type" as the old amino acid, meaning it has to have similar hydration properties as will be explained later on in the text. We evaluate all possible rotamers for the new amino acid, and choose the best one with the lowest VDW energy and no atomic overlaps. The second type of trial "move" is an exchange of two randomly-chosen amino acids, regardless of their residue type. New rotamer positions for the two exchanged amino acids are chosen from among the many possible rotamers. The rotamer combination with the lowest VDW energy and no atomic overlaps is chosen using the SCMF technique, a fast and effective way to evaluate all the rotamer combinations based on their probability distributions. After either type of trial "move", the binding free energy is calculated for the old sequence and for the trial sequence, and the Metropolis algorithm is used to accept or reject the candidate mutation. More details on the search algorithm will be presented below. Before doing so, however we describe ways to restrict our search through the amino acid sequence space to ensure that the peptide sequence is likely to be soluble.

The search for candidate peptide sequences was restricted to those peptides that are reasonable drug candidates; that is, they should be soluble in water and exhibit desired hydration properties. A peptide of the invention is of intermediate hydrophobicity. Although hydrophobicity is of great benefit in the molecular recognition of the $ASL^{Lys3}$ by the peptide chain, excessive hydrophobicity could make the peptide sequence insoluble. The peptide should also be of intermediate hydrophilicity. Hydrophilicity promotes the solubility of the peptide chain in water; but too strong a hydrophilicity could lead to the formation of an electric double layer around the peptide chain, preventing the binding between the $ASL^{Lys3}$ and the peptide chain. Positively charged amino acids are needed to strengthen the binding affinity since the $ASL^{Lys3}$ is negatively charged in solution. The peptide chain should exhibit a stable folded configuration with key amino acids exposed on an accessible surface. Thus, some constraints are required to adjust the hydration property of the peptide chain before launching the search algorithm. Once a set of initial hydration property constraints are set, they are fixed throughout the sequence evolution process.

The twenty natural amino acids were classified into six residue types according to their hydrophobicity, polarity, size and charge. The first column in Table 1 gives the amino acid type and the second column lists the amino acids of that type. In general in order to bind RNA 40~70% of the residues along a soluble peptide chain should be either positively charged or hydrophilic residues; while approximately 30~50% of the residues should be hydrophobic residues to favor specificity in the binding behavior. In this study, we adjust the number of amino acids in each residue type along the entire chain so as to change the peptide's hydration property. We have investigated three cases with three different hydration properties for the peptide chain, as shown in Table 2. These are listed according to the number of hydrophobic $N_{hydrophobic}$, negatively charged $N_{negative\ charge}$, positively charged $N_{positive\ charge}$, hydrophilic $N_{hydrophilic}$, other amino acids $N_{other}$ and glycine $N_{glycine}$ along the 15 amino acid chain.

TABLE 1

| Hydrophobic | Leu, Val, Ile Met Phe Tyr, Trp |
|---|---|
| Negatively charged | Glu, Asp |
| Positively charged | Arg, Lys |
| Hydrophilic | Ser, Thr Asn, Gln His |
| Other | Ala Cys Pro |
| Glycine | Gly |

TABLE 2

Three cases with different hydration properties

| | Case One | Case Two | Case Three |
|---|---|---|---|
| $N_{hydrophobic}$ | 4 | 5 | 3 |
| $N_{negative\ charge}$ | 0 | 0 | 0 |
| $N_{positive\ charge}$ | 2 | 2 | 1 |
| $N_{hydrophilic}$ | 5 | 6 | 6 |
| $N_{other}$ | 2 | 1 | 3 |
| $N_{glycine}$ | 2 | 1 | 2 |

Figure 2A:
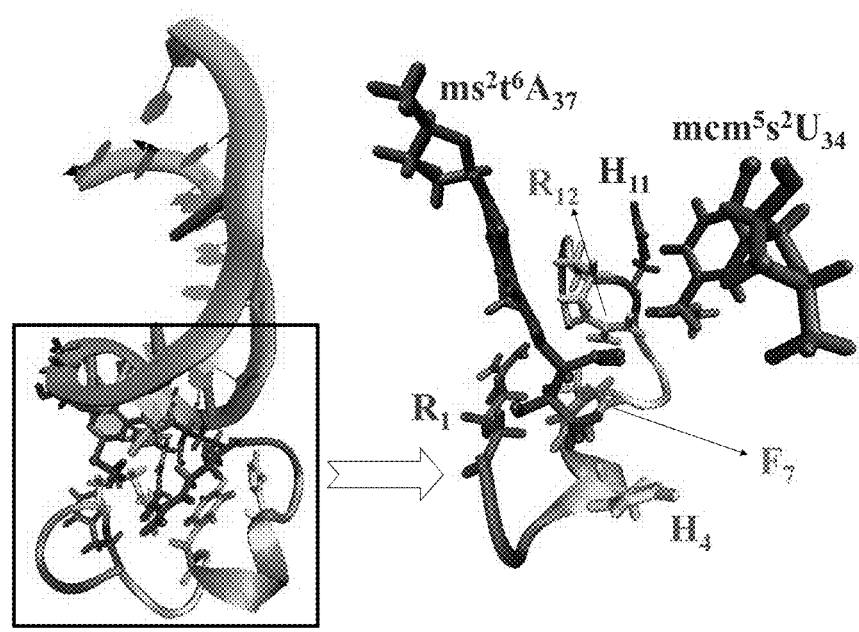
FIG. 2 are snapshots of the initial binding conformations in the search algorithm. The ASL$^{Lys3}$ is represented by the green ribbon; several important amino acids and nucleotides are specified in distinct colors. (a) Complex 1 is the state with the minimum binding free energy after an 8 ns atomistic simulation and (b) Complex 2 is the state with the minimum binding free energy after a 60 ns atomistic simulation.
Figure 2B:
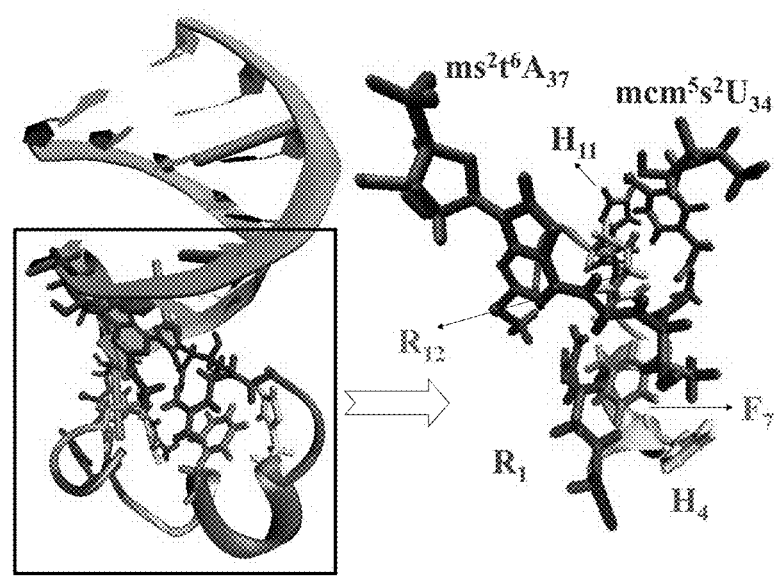

The search algorithm requires an initial conformation of the complex between the peptide chain and the $ASL^{Lys3}$. We use molecular dynamics atomistic simulation with the AMBER 10 package to determine the initial location and conformation for the complex. The procedure is the following. The peptide sequence RVTHHAFLGAHRTVG (SEQ ID NO:2) which was found in Agris' recent experimental work to exhibit relatively good binding behavior to $ASL^{Lys3}$ was put into a truncated octahedral box with an 8 angstrom buffer of TIP3P water around the peptide chain in each direction, the primary purpose being to determine its folded structure. Both $ASL^{Lys3}$ and the folded peptide chain were then solvated by placing them in a periodic box containing more than 3,000 TIP3P water molecules. The complex between the $ASL^{Lys3}$ and peptide was simulated at 298K for 60 ns in order to attain a stable binding conformation. FIG. 2 shows two configurations of the complex: (a) Complex 1 is the state with the minimum binding energy that results from an 8-ns simulation and (b) Complex 2 is the state with the minimum binding energy that results from a 60-ns simulation started from the same initial configuration as Complex 1. Complex 1 is presumed to be at a local minimum in the free energy while Complex 2 is presumed to be at a global minimum in the free energy. These two states are the initial structures in our search process.

Rotamer libraries, which are concise descriptions of side-chain conformational preferences, are used to repack the side chains during the sequence evolution process. The backbone of the peptide chain is kept fixed at all times. As is well known, amino acids prefer to adopt a series of distinct conformations, called rotamers, to accommodate their side-chains since the latter do not have the freedom to adopt arbitrary bond rotations and bond angles. In recent years, the rotamer library developed by Lovell and coauthors has been used widely in protein design due to its validity and versatility. In this work, we utilize Lovell's rotamer library to mutate the residues, and then to transplant the appropriate rotamers onto the backbone.

The SCMF technique, which is based on the mean field theory approximation (MFT), is employed to determine the rotamer combinations by evaluating their "effective potential". The best combination of rotamers is found by locating the combination with the highest conformational probability, thereby repacking the backbone. More details of the SCMF technique are described in supplemental material.

The binding free energy is defined to be the difference between the free energy of the complex, and the free energies of the ligand (here, the peptide chain) and of the receptor (here, the $ASL^{Lys3}$) prior to binding. It can be calculated according to:

$$\Delta G_{binding} = G_{TOT}^{complex} - G_{TOT}^{ligand} - G_{TOT}^{receptor} \quad (1).$$

The free energy in each term of equation (1) has the following contributions:

$$G_{TOT} = U_{INT} + U_{VDW} + U_{ELE} + G_{SOL} \quad (2),$$

where $U_{INT}$, $U_{VDW}$, $U_{ELE}$, $G_{SOL}$ are the internal energy (INT), van der Waals energy (VDW), electrostatic energy (ELE) and solvation energy (SOL); the latter contains the polar solvation energy (EGB) and the non-polar solvation energy (GBSUR). A detailed description of each type of energy can be found in references. All of the force field parameters used here originate from the library of AMBER ff99SB. We neglect the GBSUR contribution, because it is small, almost a constant throughout the entire evolution process, and it doesn't affect the research results very much. Additionally, the calculation of the GBSUR is time-consuming. It is noted that the INT energy $U_{INT}$ is always zero in the calculation of the binding free energy since it isn't involved in the binding. Consequently, when performing the search algorithm to generate a new sequence candidate at each step, we tend to calculate the binding free energy without the non-polar solvation (GBSUR) contribution of the sequence candidate to arbitrate the binding capability.

In the implementation of the SCMF method the effective potential $E(i, k_i)$ was chosen to be equal to the van der Waals energy $U_{VDW}$ instead of the total free energy $G_{TOT}$. This is done to reduce the time it takes to evaluate the best rotamer or combination of rotamers quickly. The justification for this is that for any given amino acid, the rotamer selection doesn't have much of an impact on the electrostatic energy $U_{ELE}$, the polar solvation energy $G_{EGB}$ or the nonpolar solvation energy $G_{GBSUR}$. The rotamer choice does, however, have notable impact on the VDW energy which depends strongly on the conformation and steric effects. In addition, the possibility that atoms or groups in the new positions might overlap can be monitored directly by the VDW energy as well.

The overall procedure is shown schematically in FIG. 1. Firstly, a random initial sequence, $S_0$ that satisfies the constraints on hydration properties is generated and draped over the fixed backbone conformation obtained previously from atomistic simulation. The binding free energy without GBSUR for the complex, $\Delta G_{binding}^0$, is then evaluated. Subsequently, a random number is generated to determine whether to mutate one amino acid or to exchange two amino acids. If one amino acid is to be mutated, one site along the peptide sequence is chosen randomly. The amino acid at that site is then mutated to another amino acid of the same residue type. The best rotamer for the new amino acid is chosen by evaluating the VDW energy of all the possible rotamers and then determining the best one in this mutation step. If an exchange step is chosen, two random sites along the chain and their corresponding amino acids are chosen for a mutual exchange attempt, regardless of the residue type for their amino acids. In this exchange step, we calculate the effective potential based on the van der Waals energy of all the possible rotamers and perform the SCMF procedure to optimize the conformational matrix so as to obtain the best rotamer combination with the highest conformational probability for the exchanged amino acids. Regardless of whether one amino acid was mutated or two amino acids were exchanged, the new generated peptide sequence is evaluated further by calculating the new binding free energy $\Delta G_{binding}^{1}$ without GBSUR. Finally, the new peptide is accepted or rejected according to the Metropolis criterion on the evaluation of binding free energy without GBSUR. After a total of 10,000 evolution steps, within each step containing either 15 mutation or 15 exchange attempts, the best peptide sequences are identified.

Effect of the Initial State for the Binding Conformation

Figure 3A:
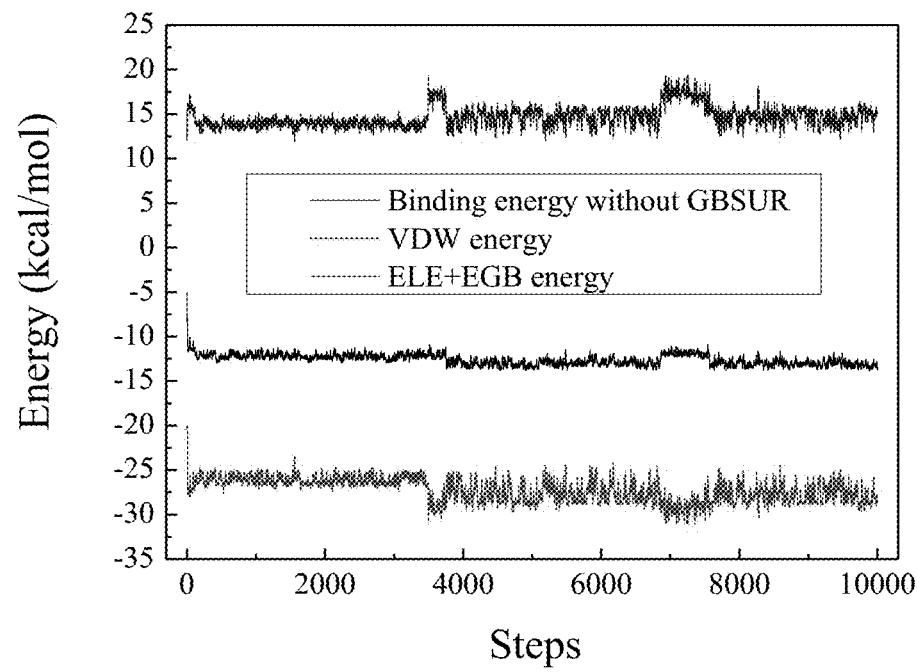
FIGS. 3a-b show the profiles of binding energy, the VDW energy and the (ELE+EGB) energy vs. number of evolution steps during the sequence evolution for: (a) Complex 1 in case One; (b) Complex 2 in case One.
Figure 3B:
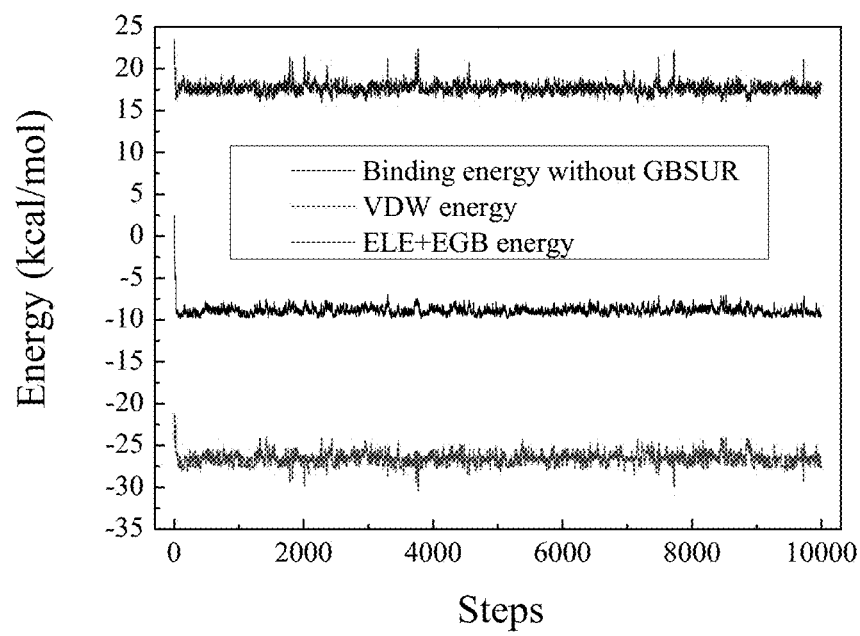

We began our study of how the initial conformation affects the evolution to a new sequence by examining the two complexes in Case One. Recall that Complex 1 and Complex 2 in FIG. 2 were obtained by simulating the binding between the $ASL^{Lys3}$ and the initial peptide chain—RVTHHAFLGAHRTVG (SEQ ID NO:2) that meets the hydration property of Case One. FIG. 3 shows the binding free energy without GBSUR, the VDW energy, and the sum of the ELE and EGB contributions to the binding free energy versus the number of steps in the search starting from Complex 1 and Complex 2. These calculations depict how the energy evolves over the course of the search. After a quick drop in the energy in the early stage of FIG. 3, the energy profile appears to stabilize, indicating that the system has evolved to an equilibrium state after 10,000 steps. In the two complexes, the VDW energy is the lowest energy because it is responsible for stabilizing the conformation of the complex. In contrast, the charge-charge (ELE+EGB) energy is positive, thereby hindering binding. This is because the polar water likes wrapping around the solutes.

To make sure that our search algorithm spans a wide range of sequences out of the huge number of possible sequence alignments, we investigated the duplication rate for the sequences in the search algorithm, which is defined as the ratio of the number of attempted mutations on identical sequences to the total number of attempted mutations on all the sequences. The results for the duplication rate for the sequences over the entire process are shown in Table 3, which indicates that on average only 4.0% of the attempted mutations are duplicated.

TABLE 3

The investigation of search duplication

|  | Complex 1 (case one) | Complex 2 (case one) |
|---|---|---|
| Total attempt mutations | 150,000 | 150,000 |
| Duplicated attempt mutations | 6,640 | 5,613 |
| Duplication rate | 4.427% | 3.742% |

Figure 4A:
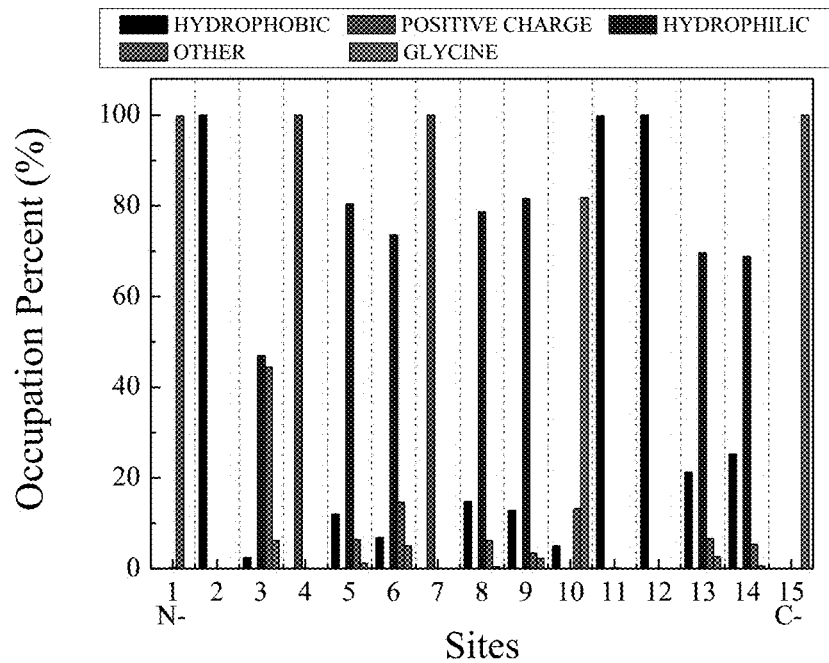
FIGS. 4a-b are graphs showing occupation percentage at each site along the peptide chain for the 500 top-ranked sequences of (a) Complex 1 and (b) Complex 2 in Case One.
Figure 4B:
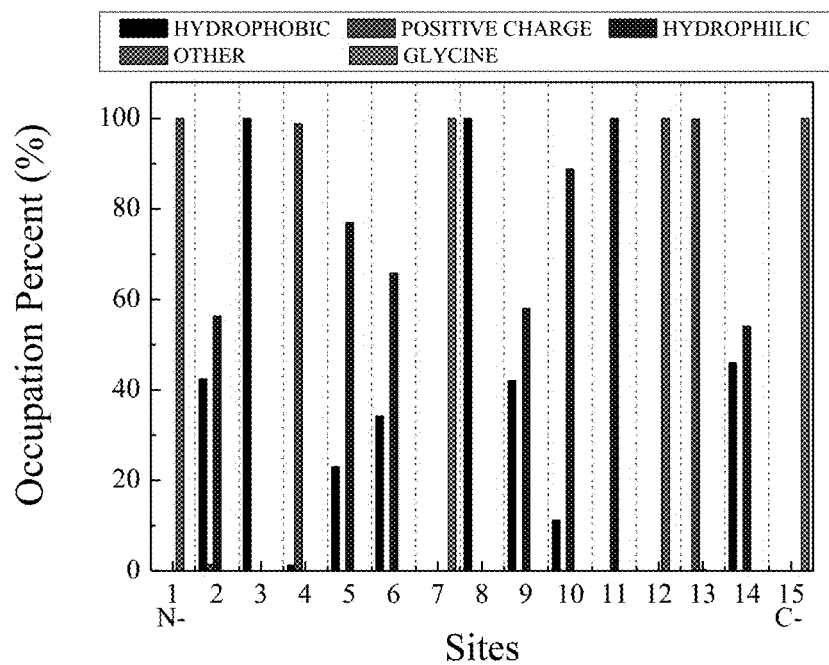

In Table 4, we list the three top-ranked search results for the peptide sequences and their corresponding binding energies starting from the two complexes in Case One. The lower binding energies (more favorable configuration) occur in Complex 1, and the higher binding energies (less favorable configuration) occur in Complex 2. This indicates that Complex 1 evolves to a peptide sequence that binds the $ASL^{Lys3}$ with higher affinity than does Complex 2. In comparing the two best peptide sequences (CWPRTSRSSGWLMTG (SEQ ID NO:14) and PHWRTTGWMNNCRMG (SEQ ID NO:17)) which are, respectively, draped on the $ASL^{Lys3}$ backbone scaffolds from Complex 1 and Complex 2, we observe that most of the residues on the two peptides are distinct, except for arginine (ARG) at site 4, threonine (THR) at site 5 and glycine (GLY) at site 15. The occupation frequency for the six residue types (see Table 1) at each site along the peptide chain, (the percentage of times a particular residue type occurs at that site), was calculated for the 500 top-ranked peptide sequences in the search algorithm. FIG. 4 shows the resulting occupation frequencies for the sequences evolved from (a) Complex 1 and (b) Complex 2. The x-axis represents the sites along the peptide chain, the y-axis represents the occupation percentage for residue types: hydrophobic, positive charged, hydrophilic, other residues and glycine. As seen in FIG. 4, the different conformations of the peptide make for differences in the occupation distributions for the various residue types, which means that the evolution results in the search algorithm are strongly dependent on the initial binding configuration.

TABLE 4

The 3 top-ranked results of the peptide sequences obtained by the search algorithm

| Rank | | | | | | | | | | | | | | | | | Binding Energy without GBSUR (kcal/mol) |
|---|---|---|---|---|---|---|---|---|---|---|---|---|---|---|---|---|---|

Sequences for Complex 1 (Case One)
SEQ ID NOs: 14, 15, and 16, repectively

| | sites | 1 | 2 | 3 | 4 | 5 | 6 | 7 | 8 | 9 | 10 | 11 | 12 | 13 | 14 | 15 | |
|---|---|---|---|---|---|---|---|---|---|---|---|---|---|---|---|---|---|
| 1 | | C | W | P | R | T | S | R | S | S | G | W | L | M | T | G | -13.87 |
| 2 | | C | W | P | R | S | S | R | S | I | G | W | L | S | Q | G | -13.84 |
| 3 | | C | W | P | R | S | S | R | S | T | G | W | L | T | M | G | -13.84 |

TABLE 4-continued

The 3 top-ranked results of the peptide sequences obtained by the search algorithm

| Rank | | | | | | | | | | | | | | | | Binding Energy without GBSUR (kcal/mol) |
|---|---|---|---|---|---|---|---|---|---|---|---|---|---|---|---|---|
| | Sequences for Complex 2 (Case One) SEQ ID NOs: 17, 18, and 19, repectively | | | | | | | | | | | | | | | |
| | sites | 1 | 2 | 3 | 4 | 5 | 6 | 7 | 8 | 9 | 10 | 11 | 12 | 13 | 14 | 15 | |
| 1 | | P | H | W | R | T | T | G | W | M | N | N | C | R | M | G | −9.83 |
| 2 | | P | H | W | R | T | N | G | W | I | N | N | C | R | L | G | −9.82 |
| 3 | | P | H | W | R | S | T | G | W | M | N | N | C | R | M | G | −9.82 |

FIGS. 5 (a) and (c) show snapshots of the structures of the two best peptide sequences evolved in the search algorithm for the backbone scaffolds of Complex 1 and Complex 2, while FIGS. 5 (b) and (d) show the respective associated contributions to the binding energy for sites along the peptide chain. As exhibited in FIG. 5(a), the long side-chain arginine (ARG) appears at site 7 (the center of the chain); this makes a strong contribution to the binding as shown in FIG. 5(*b*). The chemical and physical space between the negatively charged $ASL^{Lys3}$ and the backbone scaffold is sufficiently wide for insertion of the long, positively charged arginine side chain. In contrast, the corresponding gap in the middle of Complex 2 is not wide and so can only accommodate short side chains, leading to a relatively low energy contribution, as seen in FIG. 5(*c, d*). The chemical and physical space between the ASL and the peptide in Complex 2 is narrower than in Complex 1. The atomistic simulations indicate a lower binding energy for Complex 2 than Complex 1. This implies that within the conformation of Complex 2 the peptide sequence binds to the ASL more tightly than for Complex 1. Having an initial conformation with an initially larger chemical and physical space in which to begin the search makes it easier for the search algorithm to evolve a good peptide sequence. The conformations of the rotamers in the search algorithm are restricted to the limited number of possible states in the rotamer library so it can be challenging to find an amino acid rotamer that fits nicely into a narrow gap. In the atomistic simulations, the amino acids can adopt many more different conformations so it is easier to find a rotamer to fit into this gap but of course doing a search via atomistic simulations would be prohibitively time intensive.

Effect of the Hydration Property for the Peptide

We studied how the peptide's target hydration property affected the evolution to a new sequence by adjusting the number of amino acids in each type of residue along the entire chain. In this section we use Complex 2 as our reference conformation for study of this issue. The search algorithm was used to drape peptide sequences over the scaffold of Complex 2 subject to various hydration constraints. In Table 5, we list the 3 top-ranked search results for the peptide sequences and the associated binding energies for Cases Two and Three. By comparing the results for Case One (see bottom chart in Table 4) with those for Cases Two and Three, it is evident that the lowest binding energies occur in Case One, and that the highest binding energies occur in Case Three, i.e. that Case One evolves the best peptide sequence, and that Case Three evolves the worst peptide sequence.

A common feature in all the evolution results, despite having different hydration properties, is that some identical residues occupy the same sites in the three cases. These are arginine (ARG) at site 4, tryptophan (TRP) at site 8, asparagine (ASN) at site 11 and cysteine (CYS) at site 12. The occupation frequency for the six residue types (see Table 1) at each site along the peptide chain, (the percentage of times a particular residue type occurs at that site), was calculated for the 500 top-ranked peptide sequences in the search algorithm. FIG. 6 shows the results of the occupation frequency for the sequences in (a) Case Two and (b) Case Three. Although the different hydration properties of the peptide make for differences in the occupation distributions for the various residue types, the compilation indicates many similarities. The hydrophobic residues tend to occupy site 8 and sites near the N terminal for all three cases. The positively charged amino acids prefer to locate at sites 4 and 13. (There is no ARG at site 13 in Case 3 because there is only one positively charged amino acid in the case.) The hydrophilic residues are distributed relatively evenly over the remaining sites. More detailed discussions are given in the later section on energy analysis.

TABLE 5

The 3 top-ranked peptide sequences
obtained by the search algorithm

| Rank | sites | | | | | | | | | | | | | | | Binding Energy without GBSUR (kcal/mol) |
|---|---|---|---|---|---|---|---|---|---|---|---|---|---|---|---|---|

Sequences for Complex 2 (Case Two)
SEQ ID NOs: 20, 21, and 22, repectively

| | sites | 1 | 2 | 3 | 4 | 5 | 6 | 7 | 8 | 9 | 10 | 11 | 12 | 13 | 14 | 15 | |
|---|---|---|---|---|---|---|---|---|---|---|---|---|---|---|---|---|---|
| 1 | | V | S | L | R | S | N | W | W | M | N | N | C | R | T | G | -7.48 |
| 2 | | V | L | S | R | S | N | W | W | I | N | N | C | R | Q | G | -7.47 |
| 3 | | V | S | L | R | S | N | W | W | M | N | N | C | R | Q | G | -7.46 |

Sequences for Complex 2 (Case Three)
SEQ ID NOs: 23, 24, and 25, repectively

| | sites | 1 | 2 | 3 | 4 | 5 | 6 | 7 | 8 | 9 | 10 | 11 | 12 | 13 | 14 | 15 | |
|---|---|---|---|---|---|---|---|---|---|---|---|---|---|---|---|---|---|
| 1 | | P | G | W | R | M | T | P | W | T | S | N | C | Q | T | G | -6.79 |
| 2 | | P | G | W | R | V | T | P | W | T | S | N | C | Q | T | G | -6.77 |
| 3 | | P | G | W | R | F | T | P | W | T | S | N | C | Q | T | G | -6.74 |

Figure 7A:
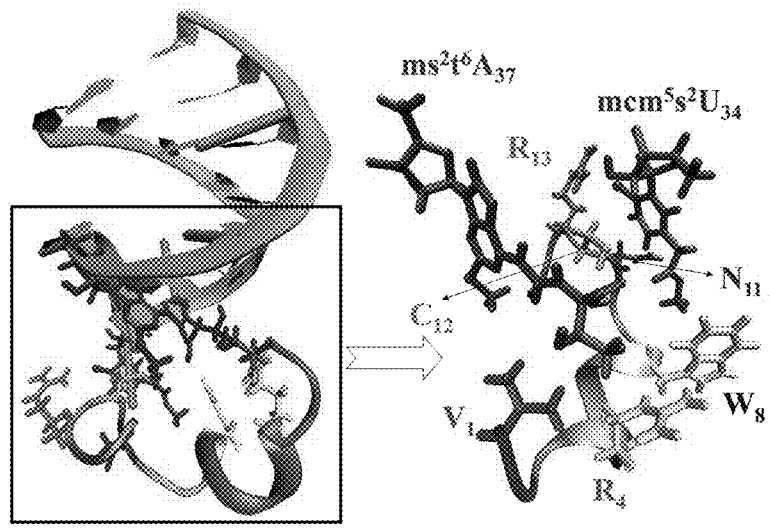
FIGS. 7a-b are snapshots of the complex formed by the best peptide sequence for complex 2 in Case 2 (a) and Case 3 (b). The ASLLys3 is represented by the green ribbon; the peptide sequences are represented by the multi-colored ribbons. The key amino acids and nucleotides are specified in distinct colors.
Figure 7B:
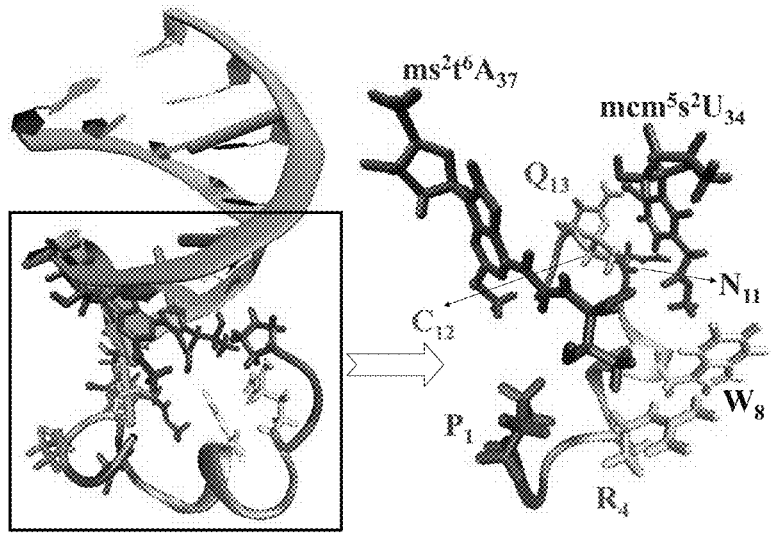
Figure 8A:
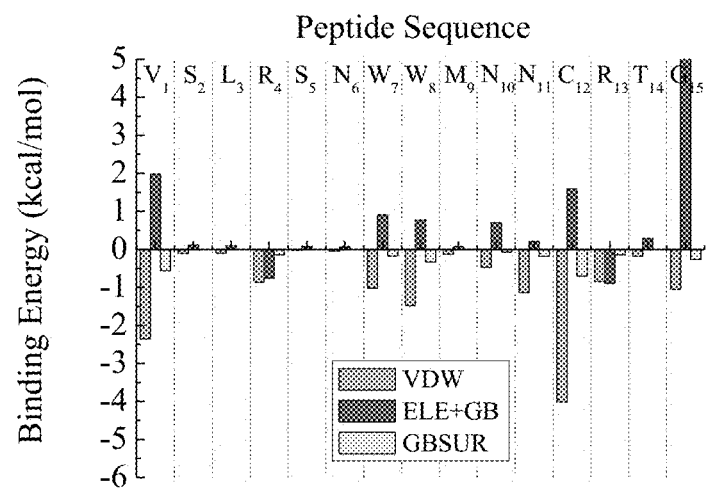
FIGS. 8a-c show the various contributions to the binding energy (a) along the sequences of the ASLLys3 and (b) along the peptide chain in Case Two, and (c) along the peptide chain in Case Three. The two modified nucleosides are highlighted in red in FIG. 8(a). The x-axis represents the sites along the ASLLys3 (8-a) and peptide chain (9-b, 9-c), and the y-axis represents the energy contributions associated with the VDW interaction, charge-charge (ELE+EGB) interaction, and nonpolar solvation (GBSUR) interaction.
Figure 8B:
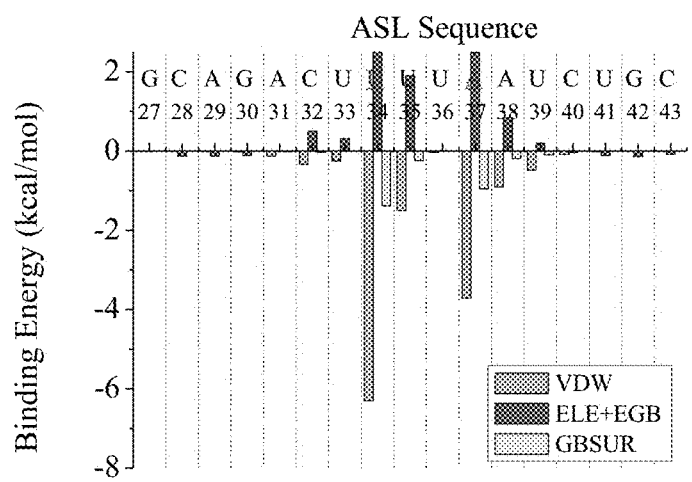
Figure 8C:
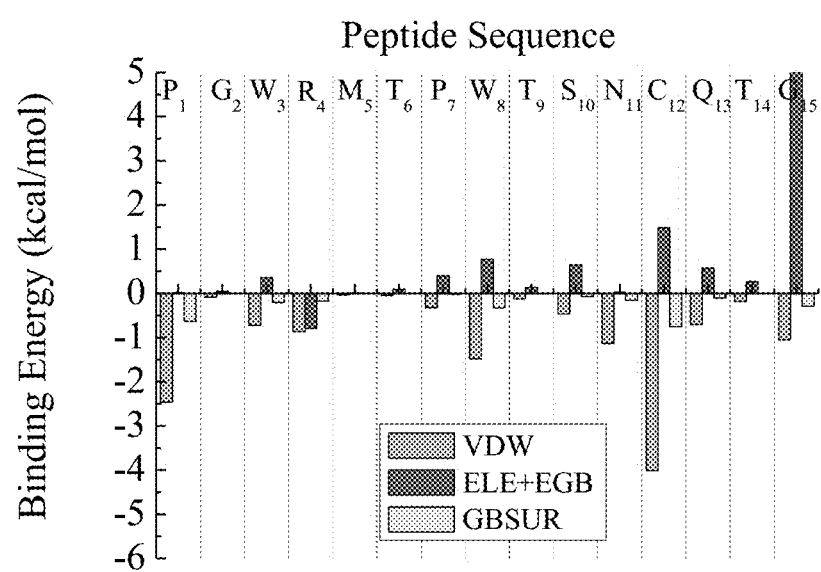

FIG. 7 shows snapshots of the structures of the best peptide sequences evolved in the search algorithm for the backbone scaffold of Complex 2 in Case Two (FIG. 7-a) and Case Three (FIG. 7-b). The locations and conformations of the key amino acids and nucleotides are also exhibited. The valine (VAL) at site 1 for Case Two is replaced by a proline (PRO) for Case Three, and the arginine (ARG) at site 13 for Case Two is replaced by a glutamine (GLN) for Case Three. The replacement of amino acids for the two cases occurs for two reasons: 1) it lowers the binding free energy; 2) it is necessary to meet the hydration constraints. Which one of these reasons is the chief factor? This can only be answered by an analysis of the energy for the two complexes.

Table 6 shows the various contributions to the binding energy for the best sequences in the three cases. Examination of the energy contributions indicates that the type of hydration property doesn't have a notable impact on the VDW energy or on the GBSUR (non-polar solvation) energy if the backbone conformation is fixed. However, the type of hydration property does affect the charge-charge (ELE+EGB) energy. For a fixed backbone conformation in this work, a change in the hydration property of the peptide, essentially means a change in the number of polar or positively charged amino acids. Increasing the number of polar or positively charged amino acids in the peptide strengthens the charge-charge attractive interaction between the peptide chain and the negatively charged, phosphate linkage of the $ASL^{Lys3}$. At physiological pH, the amino acid threonine modification of $ms^2t^6A^{37}$ has a free acid which is negatively charged as well.

TABLE 6

Contributions to the energy for the best peptide sequences in the three cases

| Cases | Binding Energy | Binding Energy without GBSUR | VDW | ELE + EGB | GBSUR |
|---|---|---|---|---|---|
| One[(a)] | -15.47 | -9.83 | -27.59 | 17.75 | -5.63 |
| Two[(b)] | -12.90 | -7.48 | -27.63 | 20.16 | -5.43 |
| Three[(c)] | -12.36 | -6.79 | -27.36 | 20.57 | -5.57 |

Sequences:
[(a)] PHWRTTGWMNNCRMG, SEQ ID NO: 17;
[(b)] VSLRSNWWMNNCRTG, SEQ ID NO: 20;
[(c)] PGWRMTPWTSNCQTG, SEQ ID NO: 23

FIG. 8 shows the various contributions to the binding energy (a) along the sequence of the $ASL^{Lys3}$ in Case Two, (b) along the peptide chain in Case Two, and (c) along the peptide chain in Case Three. In FIG. 8(*a*), we can see that the anticodon loop domain ($mcm^5s^2$U34-U35-U36-$ms^2t^6$A37) of the $ASL^{Lys3}$ accounts for the majority of the binding energy; especially the VDW energy. In FIG. 5(*d*) and FIG. 8(*b, c*), we can see that several key sites (1, 4, 8, 11, 12 and 13) existing on the peptide contribute the majority of the binding energy, regardless of the hydration properties. Reference to the structures of the complex in FIG. 5(*c*) and FIG. 7 indicates that the amino acid side chains located at these key sites point in that direction, and thus always have a good opportunity to contact with the anticodon stem and loop domain of $tRNA^{Lys3}$. Certain amino acids are always observed to be at the same sites in the 3 top-ranked peptide sequences in Table 5. For example in Case One, there is always an arginine (ARG) at site 4, a tryptophan (TRP) at site 8, an asparagine (ASN) at site 11 and a cysteine (CYS)

at site 12. Since these amino acids occupy 4 sites out of a total of 15 sites, it becomes relatively easy for them to wind up at the key sites when we exchange amino acids in the search algorithm. It also explains that why the energy profiles in FIG. 3 drop very quickly at an early stage of the search process. Additionally, by comparing the peptides' energy contributions in FIG. 8(b) for Case Two and in FIG. 8(c) for Case Three, we observe that the energy contribution of valine (VAL) at site 1 for Case Two is smaller than that of proline (PRO) for Case Three, while the energy contribution of arginine (ARG) at site 13 for Case Two is larger than that of glutamine (GLN) for Case Three. Consequently, the answer to the question posed previously in our discussion of the results in FIG. 7 is that the energy factor results in the replacement of valine at site 1 in Case Two by proline in Case Three, and the hydration constraint results in the replacement of arginine (ARG) at site 13 in Case Two by glutamine in Case Three. Although these amino acids make a great contribution to the binding capability, their functions are completely different. The question of which amino acids are necessary for binding affinity and which are necessary for binding specificity to the $ASL^{Lys3}$ needs further investigation.

Figure 9A:
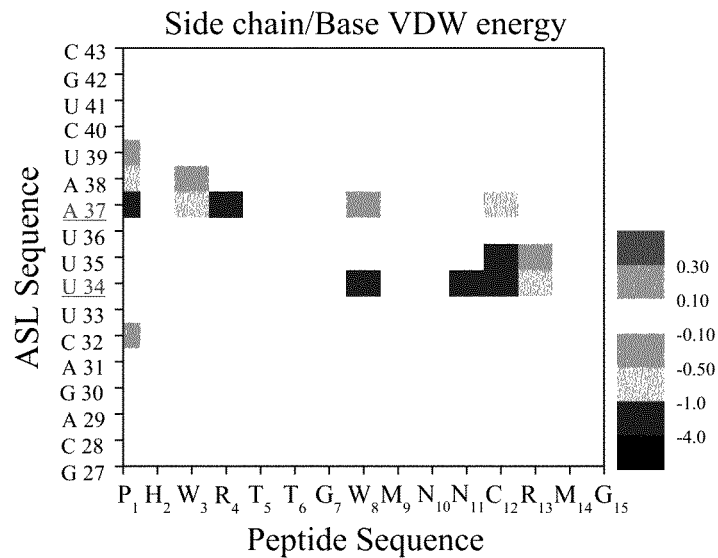
FIGS. 9a-c shows a map of the contributions to the binding energy for interactions between the nucleotides on ASL and the side chains on peptide for Case One. (a) VDW energy and (b) ELE+EGB energy involving the peptide side chain and the ASLLys3 base; (c) VDW energy and (d) ELE+EGB energy involving the side chain of peptide and the sugar ring and phosphate linkage of ASLLys3. The x-axis represents the residue sequence along the peptide chain, the y-axis represents the nucleotide sequence along ASL and the color bar on the right scales the value of the energies.
Figure 9B:
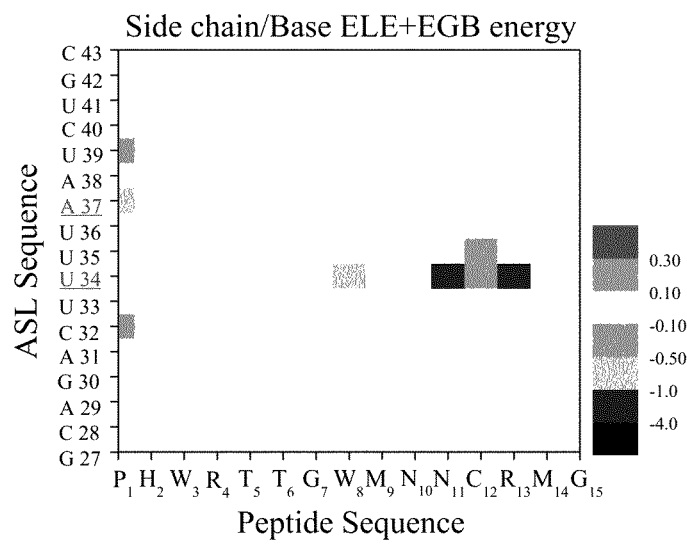
Figure 9C:
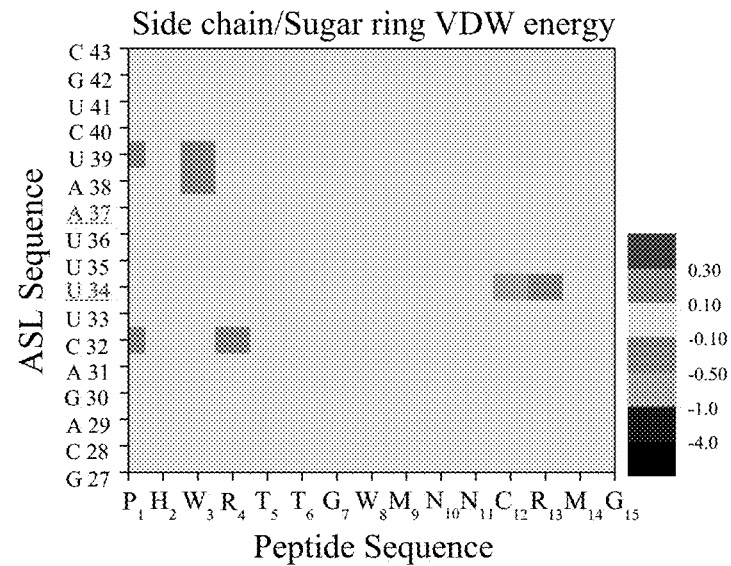
Figure 9D:
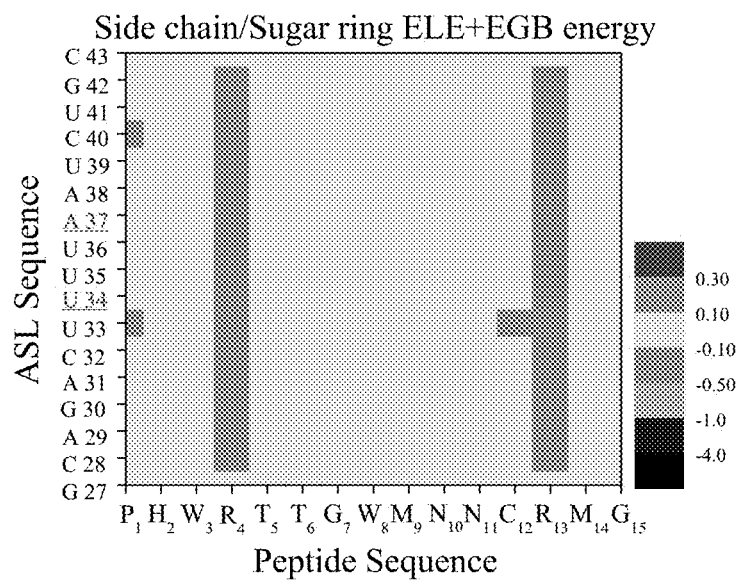
Figure 10C:
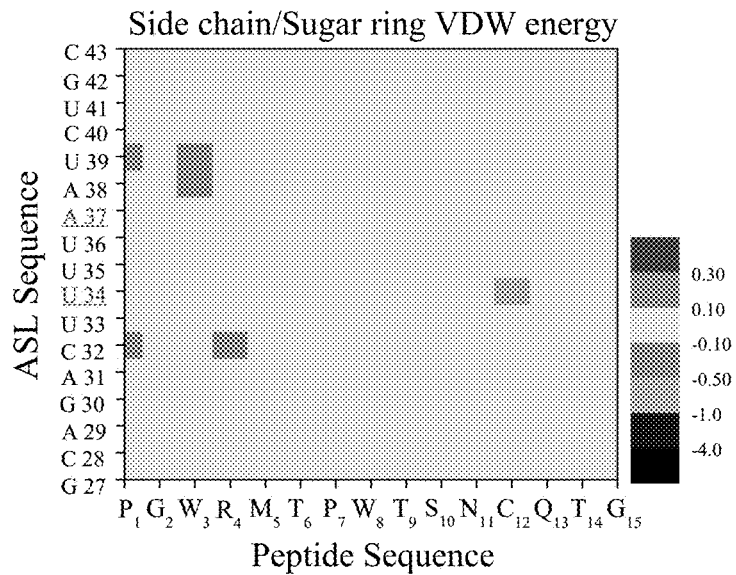
Figure 10D:
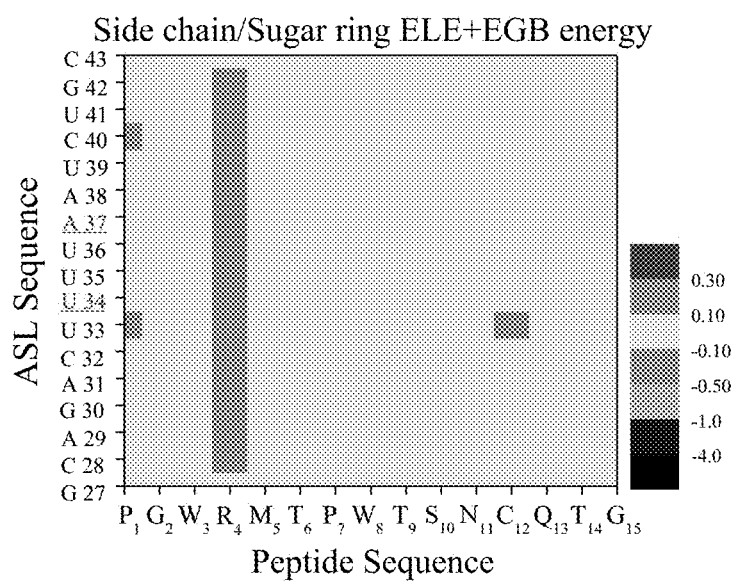
Figure 11:
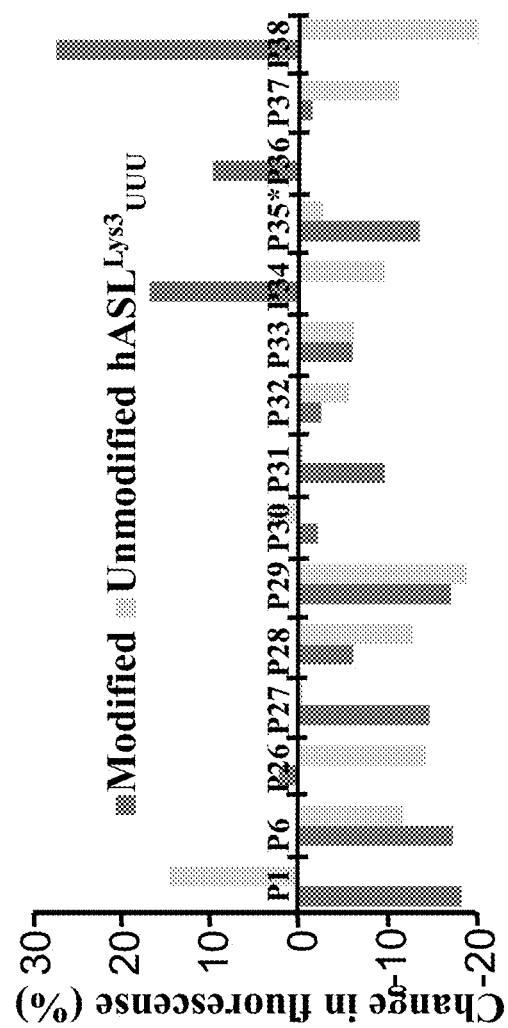
FIG. 11 shows the fluorescence of chemically synthesized peptides effected by modified and unmodified hASL$^{Lys3}_{UUU}$. An initial fluorescent signal (FS0) of peptide alone (1.5 µM) was obtained. Then, a 2-fold excess of ASL was added to each peptide and the fluorescent signal (FS1) was monitored. The percent change (100*(FS1/FS0)) is graphed for each of the assayed peptides. Dark gray bars represent the percent change in fluorescence in the presence of the modified hASL$^{Lys3}_{UUU}$ and light gray bars represent the percent change in the presence of the unmodified hASL$^{Lys3}_{UUU}$. Sequences for P1-P38 are presented in Table 9.
Figure 12A:
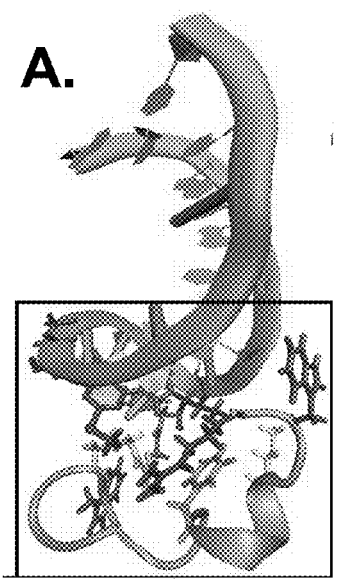
FIG. 12A-D Peptide P27 binds the modified hASL$^{Lys3}_{UUU}$ with high affinity and specificity. A. The computed equilibrium binding structure of the modified hASL$^{Lys3}_{UUU}$ bound by P27. The peptide backbone is in gold and the ribose-phosphodiester backbone of the hASL$^{Lys3}_{UUU}$ is colored in green. B. Enlargement of the interaction demonstrating the specificity achieved in the binding of the two modifications by the amino acids R1 (red), F7 (light green), W11 (light purple) and R12 (dark green). The peptide backbone is in gold and the side chains in color. The modifications ms2t6A37 (purple) and mcm5s2U34 (blue) are bound by amino acids at the beginning middle and end of the peptide. The ribose-phosphodiester backbone of the hASL$^{Lys3}_{UUU}$ is not shown. The table characterizes the contributions of different binding modes: ΔGBinding, Gibbs free energy of binding; BEw/o GBSUR, Binding Energy without GBSUR; VDW, van der Waals energy; ELE, electrostatic energy; EGB, polar solvation energy based on the Generalized Born (implicit solvent) model; GBSUR, nonpolar solvation energy which is the product of the solvent-accessible surface area of the solute molecules and the interfacial tension between the solute and solvent. C. Individual contributions of each amino acid to the VDW, ELE+EGB and GBSUR. The amino acids are colored as in B. D. Individual contributions of each nucleoside to the VDW, ELE+EGB and GBSUR. The nucleosides engaged in the interaction with P27 are those of the anticodon loop, particularly the modified nucleosides at U34 and A37. The modified nucleosides are colored as in B.
Figure 12B:
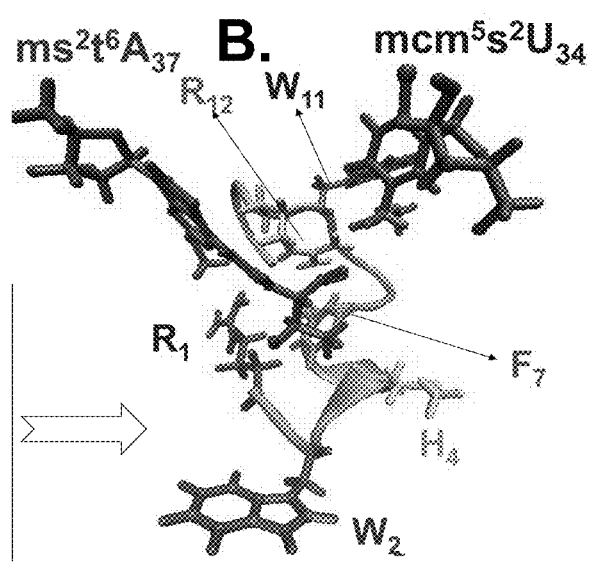
Figure 12C:
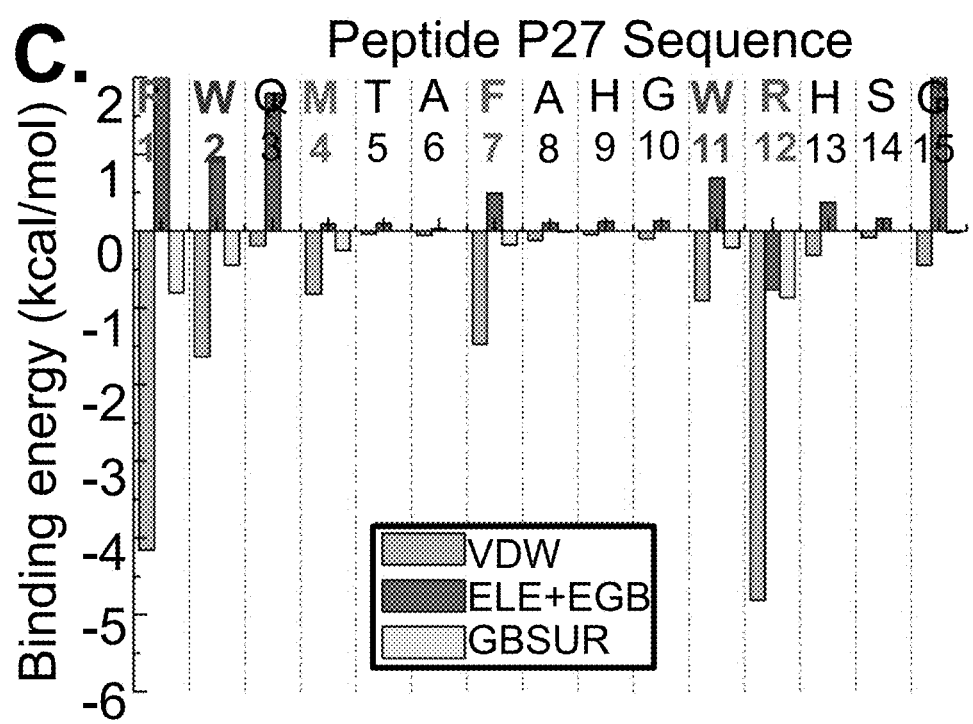
Figure 12D:
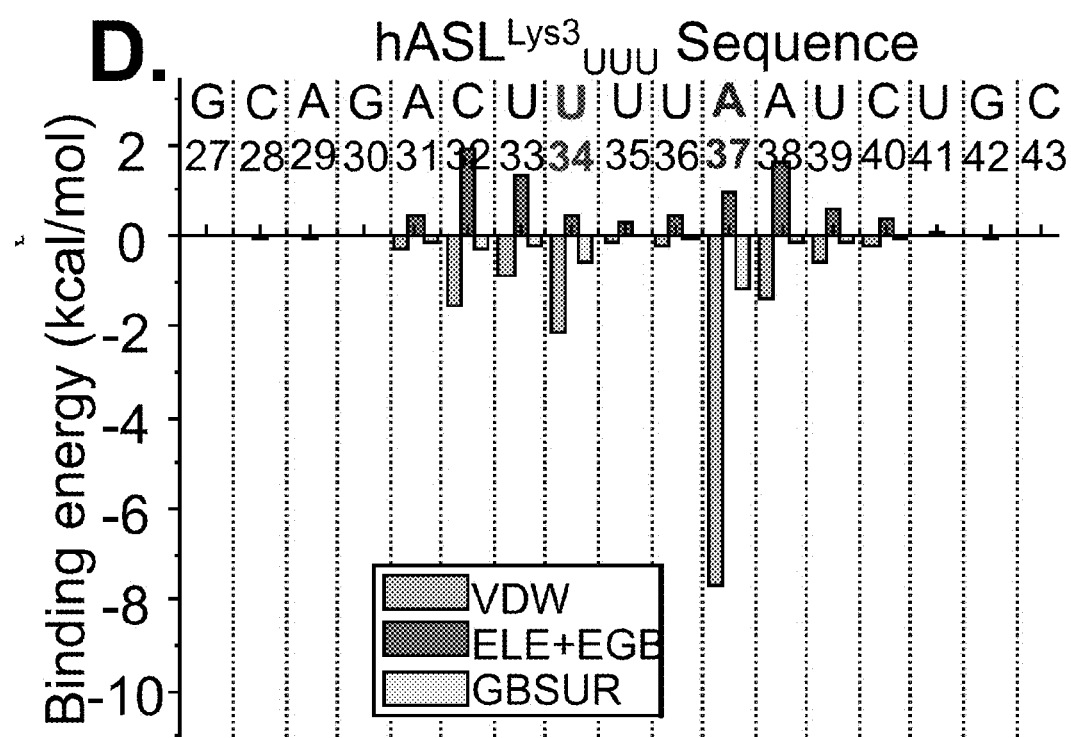

To explore which of these amino acids contributes to the binding affinity and which contributes to the binding specificity, we plotted maps of the VDW and ELE+EGB contributions to the binding energy between the nucleotides on the $tRNA^{Lys3}$ and the side chains on the peptides for Case One in FIG. 9 and for Case Three in FIG. 10.

In FIG. 9(a) for Case One, the asparagine (ASN) at site 11 and the cysteine (CYS) at site 12 are observed to have a strong preference to the anticodon loop, particularly the two modified bases on the natural nucleosides ($mcm^5s^2U34$ and $ms^2t^6A37$) due to the VDW energy. As is well known, $tRNA^{Lys3}$ in contrast to other tRNAs is the natural primer of reverse transcription of HIV-1. The unique chemistries of these two natural nucleosides within the anticodon loop play important roles in the virus' recruitment of the tRNA and the tRNA's annealing to the virus' primer binding site (14). This implies that these two hydrophilic amino acids, asparagine (ASN) and cysteine (CYS), "recognize" the $ASL^{Lys3}$, thereby impacting binding specificity. In contrast, the positively charged arginine side chain at sites 4 and 13 preferentially bind the sugar ring of the negatively charged phosphate backbone via the ELE+EGB interaction, or perhaps the dissociated acid of the threonine modification (FIG. 9(d)). Arg 4 and 13 also make a small contribution to the VDW term in the binding energy, and thus are responsible for binding affinity (FIG. 9(c)). As for the other important amino acids, such as proline (PRO) at site 1 and tryptophan (TRP) at sites 3 and 8, they attract the nucleotide $ms^2t^6A37$ through the ELE+EGB interaction (see FIG. 9-b) or recognize the sugar ring due to the π-bond resonance in the vicinity of their heterocyclic rings as reflected in the VDW interaction (see FIG. 9-c). By comparing FIG. 9(d) for Case One with FIG. 10(d) for Case Three, we observe that there is an obvious decrease in the charge-charge interaction energy when the positively charged amino acid (ARG) at site 13 in Case One is replaced by a uncharged but hydrophilic amino acid (GLN) at site 13 in Case Three, thereby leading to a great loss of binding affinity for the peptide. In contrast, the VDW interactions in the two cases don't vary a lot, despite having one less hydrophobic amino acid in Case Three than in Case One, indicating that the reduction in the number of hydrophobic residues does not have much of an impact on the binding specificity for the peptide. It is noted that in order to have a good binding ability, the peptide not only needs to have the key amino acids at their proper sites, but also requires a stable folded structure to allow the key amino acids access to the $ASL^{Lys3}$.

TABLE 7

| Peptide Designation and Rank | Peptide Sequence | Binding Energy (kcal/mol)$^a$ | SEQ ID NO |
|---|---|---|---|
| $^b$P6 | RVTHHAFLGAHRTVG | -21.26 | 2 |
| P26 | RTLHHALFGAHQTVG | -22.55 | 3 |
| P27 | RWQMTAFAHGWRHSG | -22.07 | 4 |
| P28 | RWNHCQFWNGWRAQG | -22.81 | 5 |
| P35 (P35*) | RWNHCQFWNGWRANG | -22.78 | 6 |
| P29 | RWNHQSFWHGWRACG | -22.64 | 7 |
| P30 | RWNHSQFWSLWRAHG | -22.71 | 8 |
| P31 | RWQHHSFHPLWRMSG | -21.86 | 9 |
| A | RWHHHHFSPLWRWHG | -21.56 | 10 |
| B | RHHHHHFGPPWLNCG | -14.58 | 11 |
| P32 | RHHHASFGPPWLSHG | -14.26 | 12 |
| P33 | RHSHAHFGPPWLSHG | -13.94 | 13 |

Peptides were numbered in accordance with the previous report of phage display selected sequences (9). P6 is from the original selection and P26-P38 were chosen based on predictions in silico. P35* with the sequence RWNHCQFWSGWRANG (SEQ ID NO:42) has a single amino acid serine change from P35. Peptide sequences A and B from Cases 2 and 3, respectively, were not selected for chemical synthesis and analysis.

TABLE 8

| Peptide | Sequence | SEQ ID NO |
|---|---|---|
| P1 | FSVSFPSLPAPPDRS | 40 |
| P6 | RVTHHAFLGAHRTVG | 2 |
| P26 | RTLHHALFGAHQTVG | 3 |
| P27 | RWQMTAFAHGWRHSG | 4 |
| P28 | RWNHCQFWNGWRAQG | 5 |
| P29 | RWNHQSFWHGWRACG | 7 |

TABLE 8-continued

| Peptide | Sequence | SEQ ID NO |
|---|---|---|
| P30 | RWNHSQFWSLWRAHG | 8 |
| P31 | RWQHHSFHPLWRMSG | 9 |
| P32 | RHHHASFGPPWLSHG | 12 |
| P33 | RHSHAHFGPPWLSHG | 13 |
| P34 | RFQHSNWFSGWKVNG | 41 |
| P35* | RWNHCQFWSGWRANG | 42 |
| P36 | RWNGSQWFCAWRANG | 43 |
| P37 | RHTHCAFWGAHRTVG | 44 |
| P38 | RWTHCQFWQGFRVNG | 45 |

Peptides in Table 8 were named following peptides from original phage display library screens (9). P1 and P6 (bolded) are from the original screen. P6 has been characterized (9). In addition, the binding of the modified and unmodified hASLLys3UUU by P1, P27, P31 and P35* (bolded and shaded) are characterized in this report.

TABLE 9

| Peptide | Modified or Unmodified hASL$^{Lys3}{}_{UUU}$ | $K_d$ (μM) |
|---|---|---|
| P6 | Modified | 0.50 ± 0.10$^a$ |
|  | Unmodified | ID |
| P1 | Modified | 0.13 ± 0.02 |
|  | Unmodified | 0.15 ± 0.04 |
| P27 | Modified | 0.05 ± 0.02 |
|  | Unmodified | ID |
| P31 | Modified | 0.58 ± 0.24 |
|  | Unmodified | ID |
| P35* | Modified | 1.87 ± 1.00 |
|  | Unmodified | ID | the negatively charged ASL. By adjusting the number of amino acids in each category—via Npho, Nneg, Npos, Npol, Noth, Ngly—we maintained hydration properties similar to the original P6 sequence while evolving the sequences (9).

The peptide sequence was optimized using the following computational procedure. The stable structure for the complex between the original P6 sequence and ASL was determined using AMBER. The structure of the fully modified hASL$^{Lys3}{}_{UUU}$ was taken from the high resolution, solution structure (6), providing a restrained structure to which the peptide would bind in silico. Once the stable structure of the peptide P6 with the ASL$^{Lys3}$ was determined, the peptide's amino acid sequence was evolved and optimized while keeping the backbone fixed. Each peptide sequence evolved in two types of "moves": 1) a single randomly chosen amino acid in the peptide sequence was mutated to a different amino acid from the same residue category (Table 1); or 2) two randomly chosen amino acids in the peptide sequence were exchanged regardless of the their residue category (FIG. 2) using SCMF (15). SCMF finds the optimal rotamer combination with the lowest binding energy for the two exchanged amino acid residues (FIG. 3) based on the preferred, distinct side chain conformations in Lovell's rotamer Library (16). The sequences were subjected to continued rounds of optimization (FIG. 2). By comparing the changes in binding energy before and after each of the two types of moves, the peptide sequence was evolved to those with the lowest binding energies and thus, increased binding affinity to the modified hASL$^{Lys3}{}_{UUU}$.

The initial P6 sequence was subjected to an evolution over several hundred thousands of rounds of 15-amino acid peptide sequences that, based on binding energies, should recognize and bind modified hASLLys3UUU with a similar or higher affinity than P6. Initial results from the in silico selection suggested two optimized peptide sequences, P26, R-T-L-H-H-A-L-F-G-A-H-Q-T-V-G (SEQ ID NO:3) and P27, R-W-Q-M-T-A-F-A-H-G-W-R-H-S-G (SEQ ID NO:4). These sequences exhibited binding energies to the hASLLys3UUU lower than that of P6 (P26, −22.55 kcal/mol and P27, −22.07 kcal/mol, respectively, vs. P6 −21.26 kcal/

TABLE 10

| Peptide | 1 | 2 | 3 | 4 | 5 | 6 | 7 | 8 | 9 | 10 | 11 | 12 | 13 | 14 | 15 | SEQ ID NO |
|---|---|---|---|---|---|---|---|---|---|---|---|---|---|---|---|---|
| P1 | F | S | V | S | F | P | S | L | P | A | P | P | D | R | S | 40 |
| P6 | R | V | T | H | H | A | F | L | G | A | H | R | T | V | G | 2 |
| P27 | R | W | Q | M | T | A | F | A | H | G | W | R | H | S | G | 4 |
| P29 | R | W | N | H | Q | S | F | W | H | G | W | R | A | C | G | 7 |
| P31 | R | W | Q | H | H | S | F | H | P | L | W | R | M | S | G | 9 |
| P35* | R | W | N | H | C | Q | F | W | S | G | W | R | A | N | G | 42 |
| Signature | R | W | Q/N | H | X | X | F | Pho | X | G/A | W | R | X | X | G | 39 |

In Table 10, X is any amino acid; Pho is a hydrophobic amino acid. Position 3 is either glutamine (Q) or asparagine (N) and position 10 is either glycine (G) or alanine (A).

The canonical 20 amino acids were categorized into six distinct groups according to hydrophobicity, polarity, size and charge (Table 1). These hydration properties were necessary to ensure the peptide did not become too hydrophobic (and thus insoluble) or so hydrophilic that binding to hASL$^{Lys3}$ was inhibited. The overall charge of the peptide was chosen to be slightly positive to ensure interaction with mol). Based on these initial results, we developed three distinct peptide sequence cases. The three Cases varied within the six residue categories (Table 1B). Although different, each of the three Cases is still within the overall desired levels of moderate hydration and charge properties (slightly positively charged). P6, the initially evolved sequences P26 and P27, and three of the top ten sequences from each of the first two Cases 1 and 2 have lower binding energies than those of Case 3 (Table 2). This is likely due to the increased allowance in Cases 1 and 2 for positively charged and hydrophobic residues (Table 2). The binding energies calculated for P26 and P27 and Cases 1 and 2, but not 3, are on par with or lower than the binding energy for P6. This suggests a potential increase in their binding affinity for modified hASL$^{Lys3}{}_{UUU}$ versus that of P6.

Sequences predicted during the in silico optimizations to have the lowest binding energies and thus, potentially higher affinity for modified hASL$^{Lys3}$, were selected for validation with a fluorescence assay (9). Fifteen peptides (Table 3) were chemically synthesized with fluorescein at the N-terminus to allow for very sensitive, low volume detection of peptide-RNA binding interactions. P1 and P6 from phage display selections (9), the initially evolved sequences, P26 and P27, and the best binders from each of the Cases 1, 2 and 3 were synthesized. Variants of these sequences that had one or two amino acid changes were also synthesized (Table 3). During the initial validation assay, changes in the amount of fluorescence were monitored to determine whether the peptide was binding to the modified and/or unmodified hASLLys3UUU and to what relative degree (FIG. 12). In this screening assay, P6 behaved as expected. When bound by the modified hASL$^{Lys3}{}_{UUU}$, P6 fluorescence was quenched more than when bound by the unmodified hASL$^{Lys3}{}_{UUU}$. Other peptides behaved similarly. Still others demonstrated non-specific binding in that the degree of fluorescence did not significantly differ between the binding of modified and unmodified hASL$^{Lys3}{}_{UUU}$ (FIG. 12). Peptides P1, P26, P34, P36, and P38 exhibited fluorescence characteristics that indicated an RNA binding mode that increased the fluorescence either with the unmodified or modified hASL$^{Lys3}{}_{UUU}$, but not both. This result, being counter to the better understood binding of P6 (9), will require further study to understand how these peptides are recognizing the RNA.

Three peptides—P27 one of the two initially evolved, P31 from Case 1, and P35*, a variant of P35 from Case 2—exhibited a preference for the modified hASL$^{Lys3}{}_{UUU}$, as did the phage selected P6. However, the fluorescent signals of these three peptides were quenched to a greater degree in binding the modified hASL$^{Lys3}{}_{UUU}$ than was the fluorescence of P6. All three of these peptides showed a very high selectivity for the modified hASL$^{Lys3}{}_{UUU}$ but little or no change in fluorescence was observed in their binding to unmodified hASL$^{Lys3}{}_{UUU}$ (FIG. 12). In contrast, the peptides P32 and P33 emanating from Case 3, though having the best binding properties among that family of peptides, had significantly weaker affinities and a lack of specificity for the modified hASL$^{Lys3}{}_{UUU}$ (FIG. 12). Thus, peptides selected in silico as having high affinities for the modified hASL$^{Lys3}{}_{UUU}$ appear from the screening assay in vitro to have higher affinities and higher specificities.

Peptides P1, P6, P27, P31, and P35* having exhibited qualitatively the highest affinity and specificity for the modified substrate were subjected to a quantitative analysis of their binding to both the modified and the unmodified hASL$^{Lys3}{}_{UUU}$. The equilibrium binding constant (as the dissociation constant Kd, Table 4) was determined for each peptide in its interaction with the modified and the unmodified hASL$^{Lys3}{}_{UUU}$ and compared to that for P6 (Table 4). Peptides P1 and P27 bound the modified hASL$^{Lys3}{}_{UUU}$ with considerably higher affinities and specificity than P6 (Table 4). P31 bound the modified hASL$^{Lys3}{}_{UUU}$ with specificity, but its affinity for the ASL was equivalent to P6. In contrast, P1 lacked specificity for the modifications, however its affinity for the two ASLs was four fold that of P6 (modified hASL$^{Lys3}{}_{UUU}$ Kd=0.13±0.02 μM and unmodified hASL$^{Lys3}{}_{UUU}$ 0.15±0.04 μM). P27 from the initial selection in silico exhibited the highest affinity coupled with the greatest specificity for the modified hASL$^{Lys3}{}_{UUU}$. The evolved peptide P27 had a 10-fold higher affinity than P6 for modified hASL$^{Lys3}{}_{UUU}$ (Kd=0.05±0.02 and 0.50±0.10 μM, respectively).

Figure 5C:
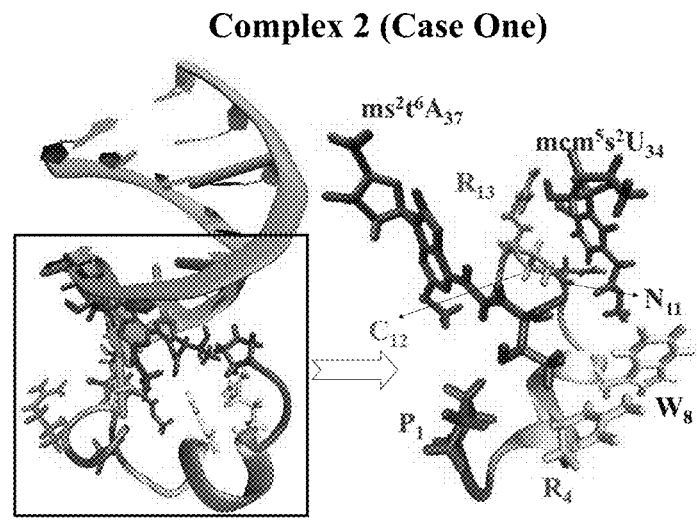
Figure 5D:
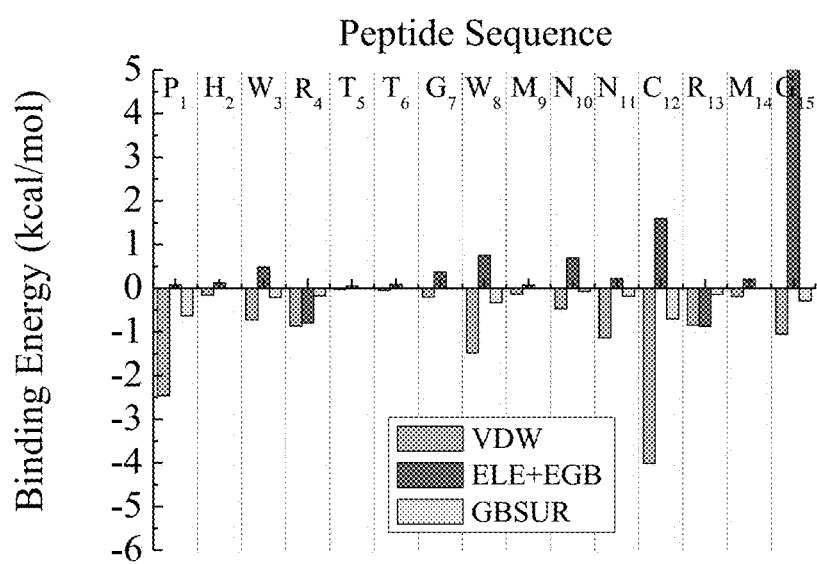
Figure 6A:
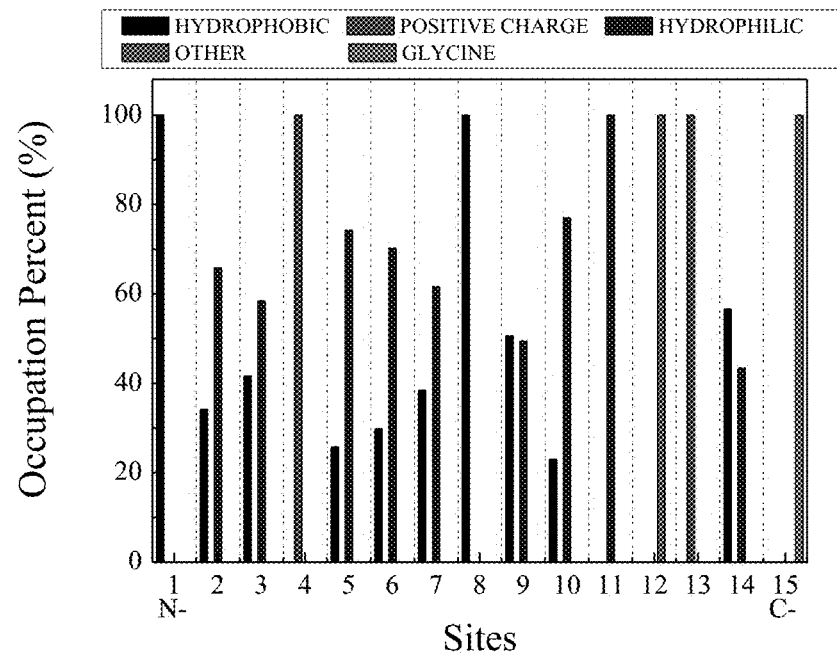
FIGS. 6a-b show the occupation percentage at each site along the peptide chain for the 500 top-ranked sequences of Complex 2 in (a) Case 2; (b) Case 3. The x-axis represents the sites along the peptide chain, the y-axis represents the occupation percentage for residue types: hydrophobic, positive charged, hydrophilic, other residues and glycine.
Figure 6B:
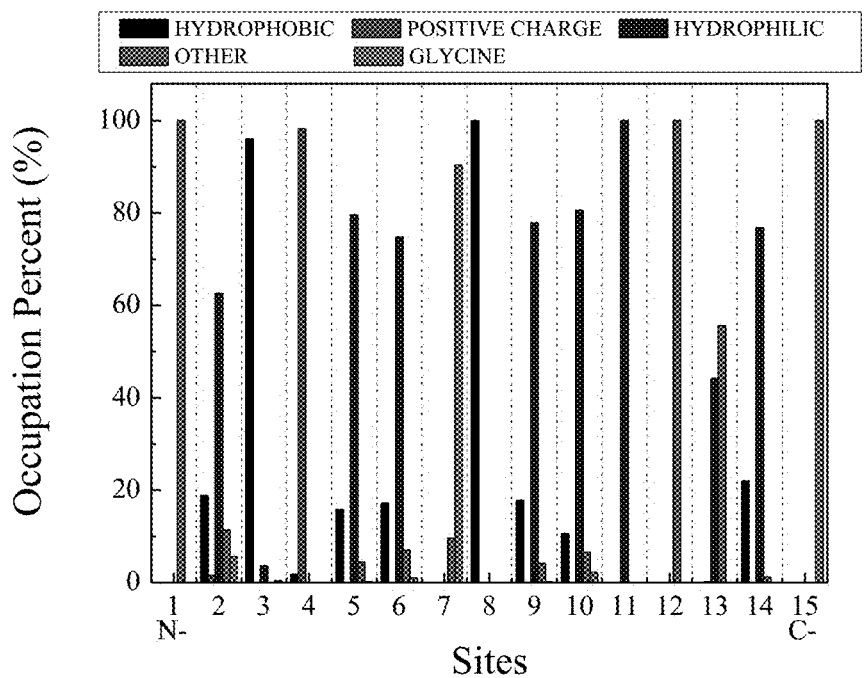

Peptide P27 has the highest affinity coupled with highest specificity for binding of the modified hASL$^{Lys3}{}_{UUU}$. The calculated structure bound to the modified hASL$^{Lys3}{}_{UUU}$ at equilibrium reveals how this affinity and specificity are achieved (FIG. 5A). Amino acids throughout P27 are engaged with the extensive chemistries of the two modifications unique to the tRNA$^{Lys3}{}_{UUU}$. The two arginines, R1 and R12, bracket the threonylcarbamoyl-group of ms2t6A37 (FIG. 5B). At the middle of the peptide, F7 is closely associated with the hydrophobic methyl of the threonyl-side chain. The imidazole ring of W11 lies above the methyl-ester of the 5-methoxycarbonylmethyl-moiety of mcm5s2U34. As evidenced by calculations for each of the 15 amino acids, R1, R12, F7, and W11 contribute to the ΔGBinding (FIG. 5C). The binding energy contributed by each of the nucleosides of the modified hASL$^{Lys3}{}_{UUU}$ have also been calculated. The binding energy is concentrated in the anticodon loop, as opposed to the stem. However, the two modifications, particularly ms2t6A37, provide the most significant binding energies.

In one embodiment of the invention, a hybrid search algorithm that combines Monte Carlo (MC), self-consistent mean field (SCMF) and concerted rotation (CONROT) techniques to evolve peptide sequences in flexible chain conformations with superior binding affinity to ASLLys3 with its natural posttranscriptional modifications was used. The hybrid MC/SCMF/CONROT search algorithm allows us to iterate between sequence mutations and conformation changes, thereby optimizing the peptide simultaneously in sequence space and in conformation space during the evolution. By performing the hybrid search algorithm with various choices of the parameters that determine the type of move to make (a sequence mutation or a change of peptide conformation), we examined three different sets of peptide hydration properties, and identified several potential peptide candidates. A further energetic and structural analysis for the evolved peptides revealed that two hydrophilic amino acids (the asparagine at site 11 and the cysteine at site 12) at the C-terminus of the peptide play important roles in "recognizing" ASLLys3 via the van der Waals interaction, contributing to the binding specificity. The positively charged arginine on the peptides preferentially attracts the negatively-charged sugar ring/phosphate linkage with the charge-charge interaction, contributing to the binding affinity.

Figure 13:
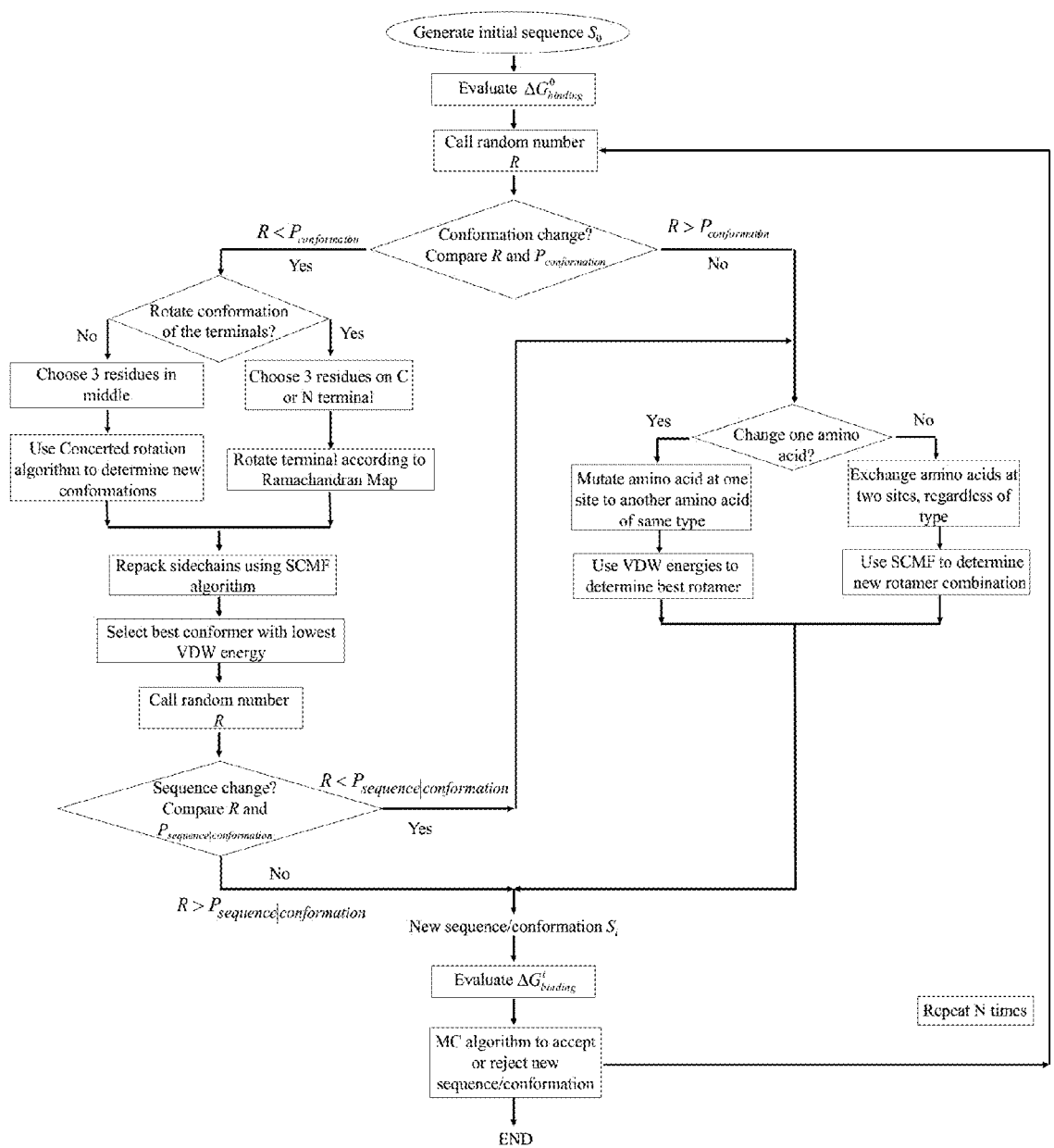
FIG. 13 shows the flow sheet for the MC/SCMF/CONROT hybrid search algorithm.
Figure 14:
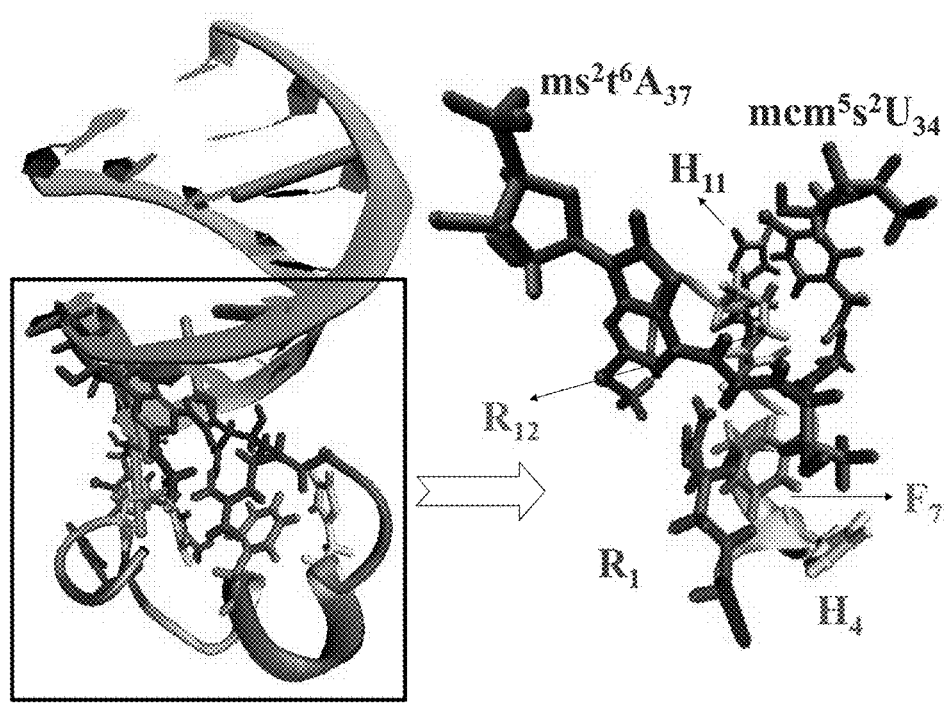
FIG. 14 shows snapshots of the initial binding conformation for the complex in the hybrid search algorithm. The ASLLys3 is represented by the green ribbon; the P6 peptide sequence—RVTHHAFLGAHRTVG (SEQ ID NO:2) is represented by the multicolored ribbon. Several important amino acids and nucleotides are shown in distinct colors. The configuration of the complex is extracted from a 60 ns atomistic simulation, and is presumed to be at a global minimum in the binding free energy.

The hybrid algorithm is an extension of the algorithm discussed above to include not only a search through sequence space to find the best binder [55], but a search through conformation space to take the backbone conformational flexibility into account. The procedure for the resulting hybrid search algorithm is shown in FIG. 13. There are two main functional modules: one is for conformation changes and the other is for sequence mutations. Two probability parameters: $P_{conformation}$ and $P_{sequence|conformation}$ are used to control the process of evolution so that the peptide has either a conformation change, a sequence change or both simultaneously. In order to design peptides that are drug candidates, we also introduce some constraints on the allowed hydration properties of the evolved peptides. Details of the hydration property constraints are described later. The outline of the strategy is:

(1) Generate an initial peptide sequence S0 that meets the hydration property constraint.

(2) Calculate the binding free energy (without GBSUR, the nonpolar solvation energy) for the complex composed of the ASL$^{Lys3}$ and the initial peptide chain S0.

(3) Compare the conformation probability ($P_{conformation}$) with a random number (R) in order to determine which module to call: the conformation change module or the sequence mutation module.

(4) If, the sequence of the peptide is mutated. There are two ways to do this: either mutate one amino acid or exchange two amino acids. When one amino acid is mutated, another amino acid of the same residue type (see below) is randomly chosen to substitute for the old one, resulting in the generation of a new attempted sequence. In contrast, when two amino acids are exchanged, they are randomly chosen regardless of the residue types of the amino acids, again resulting in the generation of a new attempted sequence. Skip to Step (7) to evaluate the binding capability of the new sequence.

(5) If, the conformation of the peptide backbone is changed. There are two ways to do this. The first way is to use the concerted rotation (CONROT) method to displace three consecutive residues (viz. nine consecutive skeletal atoms) in the middle of the peptide chain. The second way is to move one of the two ends (N- and C-terminus). Any attempts to twist the skeletal bonds on the three consecutive residues at the end of the peptide chain are permissible as long as the torsion angles ($\phi$ and $\psi$) satisfy the Ramachandran plot [56~58]. After either type of move, there will be many possible conformations for the side chains. Self-consistent mean field (SCMF) theory is employed to repack the side chains. Through calculating the VDW energy of the repacked conformer, the best attempted conformer is selected, and is then subject to further evaluation.

(6) After Step (5), the functional module to mutate the sequences is conditionally launched by comparing the conditional probability that the sequence is changed after a conformation change move ($P_{sequence|conformation}$) and another random number (R). If, we execute the sequence mutation and go to Step (4) again. If not, this new attempted conformer will get a final evaluation for its binding capability at Step (7).

(7) The new attempted sequence/conformation Si is evaluated, this time by calculating the binding free energy (without GBSUR). The Metropolis algorithm is used to accept or reject this attempted sequence/conformation Si. These seven steps are repeated for hundreds of thousands of times to evolve good sequence candidates.

Here, we briefly introduce other aspects of the hybrid search algorithm. Prior to the evolution, we generate a random starting sequence that satisfies the hydration properties required for each case. The starting conformation is the same as that for P6. If the case has the same hydration properties as the P6 peptide, we randomly mutate the amino acids on P6 to other amino acids of the same residue type, or randomly exchange the locations of some amino acids regardless of their residue types. No energy evaluation is involved into the mutation and the exchange of the amino acids here. If the case doesn't has the same hydration properties as the P6 peptide, we randomly mutate some of the residues on P6 to achieve a peptide that has the requisite hydration properties. Subsequently, we follow the above strategy to randomly mutate and exchange the amino acids on the chain to generate a random starting sequence suitable to this case. In the search algorithm, the SCMF technique is employed to search for appropriate rotamers during the single mutation moves and during the residue exchange moves. The side-chain conformations are chosen from the rotamer library of Lovell et al.

As with the original algorithm, the binding free energy is defined to be the difference between the free energy of the complex, and the free energies of the ligand (here, the peptide chain) and of the receptor (here, the ASLLys3) prior to binding. It can be complex ligand receptor calculated according to:

$$\Delta G_{binding} = G_{TOT}^{complex} - G_{TOT}^{ligand} - G_{TOT}^{receptor} \qquad (1).$$

The free energy in each term of equation (1) has the following contributions:

$$G_{TOT} = U_{INT} + U_{VDW} + U_{ELE} + G_{SOL} \qquad (2),$$

where UINT, UVDW, UELE, GSOL are the internal energy (INT), van der Waals energy (VDW), electrostatic energy (ELE) and solvation energy (SOL); the latter contains the polar solvation energy (EGB) and the non-polar solvation energy (GBSUR).

At each step of the hybrid search algorithm, we calculate the binding free energy (without GBSUR) to evaluate the binding capability of the new trial sequence, then employ the Metropolis algorithm to accept this new attempt or not. The GBSUR contribution is neglected. It is very small, does not change very much during the entire evolution process and results in little to no significant affect. Additionally, the calculation of GBSUR is time-consuming. Details can be found in our previous work.

Figure 15A:
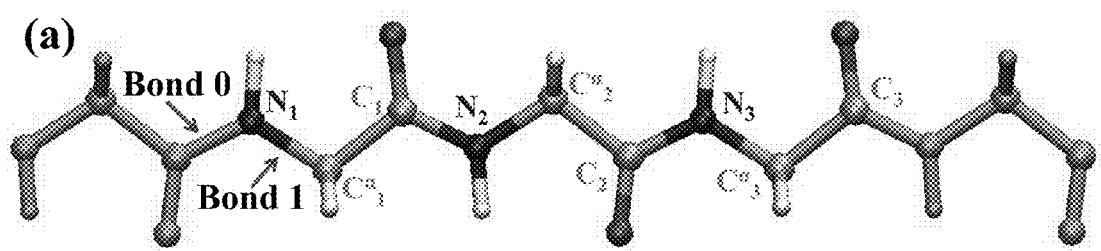
FIG. 15 is a schematic showing three consecutive residues (multicolored beads) in the middle of the peptide chain are subjected to the CONROT move, and two other residues at the ends (green beads) are kept fixed. The side chains on the peptide are not shown for clarity. The hydrogen atoms (white), nitrogen atoms (blue), carbon atom (cyan) and oxygen atom (red) are shown. (a) Nine skeletal atoms are labeled for identification. The first bond (N1-Cα1) is designated as Bond 1, the bond preceding Bond 1 is designated as Bond 0. (b) The dihedral angles ($\phi$, $\psi$, $\omega$) and the bond angles ($\theta w$, $\theta \phi$, $\theta \psi$) are marked.
Figure 15B:
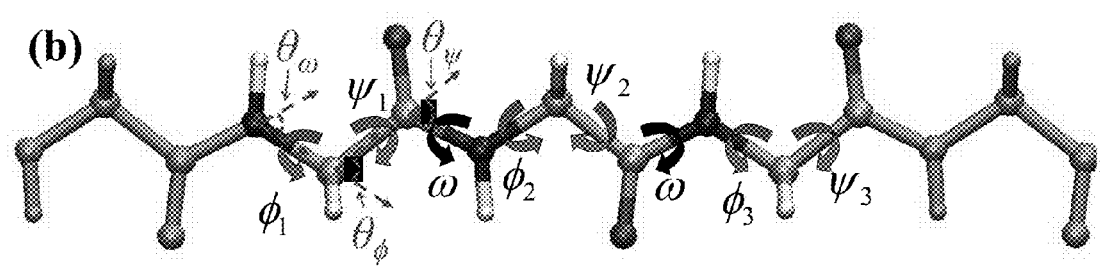

The CONROT technique is employed to displace the backbone conformation of any three consecutive non-terminal residues, i.e. residues in the middle of the peptide chain. The skeletal dihedral angles which describe the individual rotations of the bonds (N—C$\alpha$), (C$\alpha$-C) and (C—N) in the backbone scaffold are denoted by ($\phi$, $\psi$, $\omega$), respectively, and the skeletal bond angles with an apex at (N, C$\alpha$ and C) are specified by ($\theta\omega$, $\theta\phi$ and $\theta\psi$), respectively. Through measuring the torsion angles ($\phi$, $\psi$, $\omega$), we can determine the backbone conformation of the peptide. FIG. 15(a) gives a representation of a short fragment containing three consecutive non-terminal residues (viz. nine consecutive skeletal atoms) that are subject to a CONROT move. For convenience, we have labeled the nine consecutive skeletal atoms in order to identify them. The different torsion angles {$\phi$1, $\psi$1, $\omega$, $\phi$2, $\psi$2, $\omega$, $\phi$3} along the backbone are indicated in FIG. 15(b).

In the CONROT move, we change the torsion angles {$\phi$1, $\psi$1, $\omega$, $\phi$2, $\psi$2, $\omega$} of the three consecutive residues, and leave the positions of the remaining residues on the backbone unchanged, as shown in FIG. 15. Since the backbone atoms (C$\alpha$-C—N—C$\alpha$) adopt the trans conformation, the skeletal dihedral angle $\omega$ is always equal to $\pi$. Given a change in $\phi$1—the "driver angle", the other three torsion angle {$\psi$1, $\phi$2, $\psi$2} can be expressed as functions of $\phi$1 using the CONROT technique. For any given $\phi$1, solution sets for {$\psi$1, $\phi$2, $\psi$2} may exist, but sometimes may not exist. If the solution sets for ($\phi$1, $\psi$1, $\phi$2, $\psi$2) exist, and each pair of ($\phi$, $\psi$) does not violate the Ramachandran plot for the general case, we rotate these skeletal bonds according to the solution set, resulting in the change of backbone conformation. More details on how to obtain the solution set ($\phi$1, $\psi$1, $\phi$2, $\psi$2, $\phi$3, $\psi$3) and conduct the CONROT move are given in supplemental material.

(a) Sequence Evolution

The sequence of moves in the hybrid Monte Carlo (MC)/self-consistent mean field (SCMF)/concerted rotation move (CONROT) search algorithm is controlled by two probability parameters: $P_{conformation}$ and $P_{sequence|conformation}$, which determine the probability of making a conformation change move and the probability of making a sequence change move after making a successful conformation change, respectively. Based on the value of P conformation, we can either make a sequence change move alone (right side of flow diagram in FIG. 13) or we can make a conformation change move that may or may not be followed by a sequence change move (left side of flow diagram in FIG. 13). The conditional probability $P_{sequence|conformation}$ determines whether a sequence change move will occur after the conformation change move. For example, setting $P_{conformation}=0.00$ allows for a sequence change move alone with no further attempts to change the backbone conformation. Setting ($P_{conformation}$, $P_{sequence|conformation}$)=(0.60, 0.20) means that there is a 60% probability to change the peptide's conformation and a 40% probability to change the peptide's sequence alone; once a successful conformation change move has been made, there still remains a 20% probability to change the old sequence to a new sequence. A series of searches at different values of $P_{conformation}$ and $P_{sequence|conformation}$ were performed to examine the binding capability of the resulting peptide chains. There are 10,000 steps in each search wherein each step contains at least 15 attempts to mutate the amino acids or to change the backbone conformation. Overall, more than 150,000 attempts were made for each search. The first 2,000 steps in the search procedure are limited to sequence-mutation moves (the conformation is set to the fixed initial configuration), while the later 8,000 steps involve execution of both types of moves based on the values of $P_{conformation}$ and $P_{sequence|conformation}$.

Figure 16A:
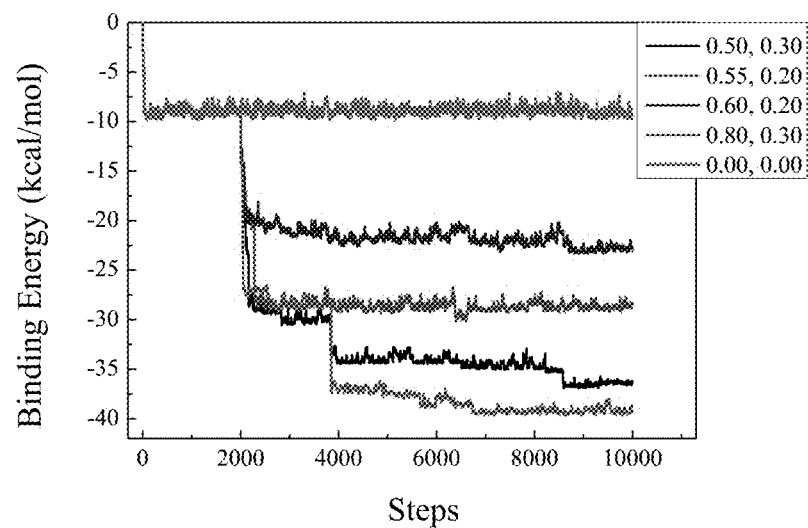
FIG. 16a-c shows binding energy profiles at various values of ($P_{conformation}$, $P_{sequence|conformation}$). (a) Case One, (b) Case Two, and (c) Case Three.
Figure 16B:
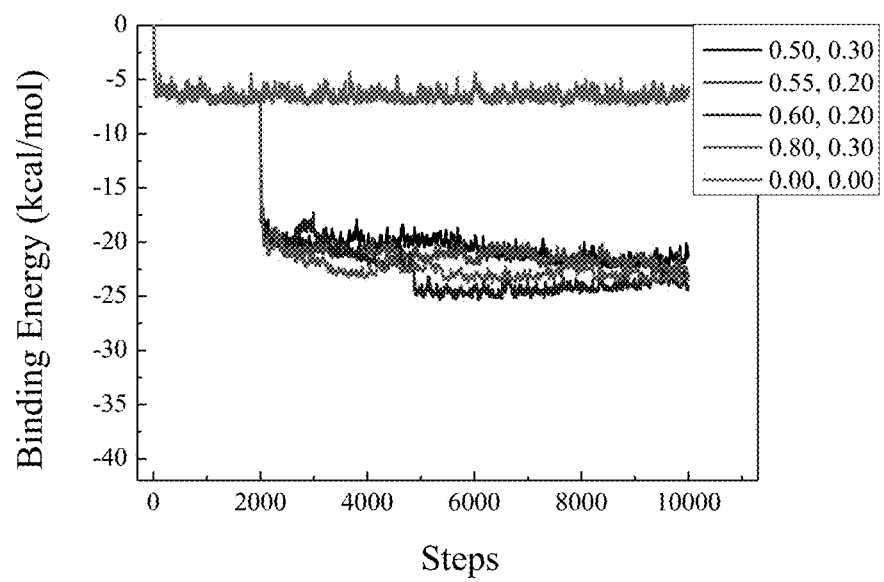
Figure 16C:
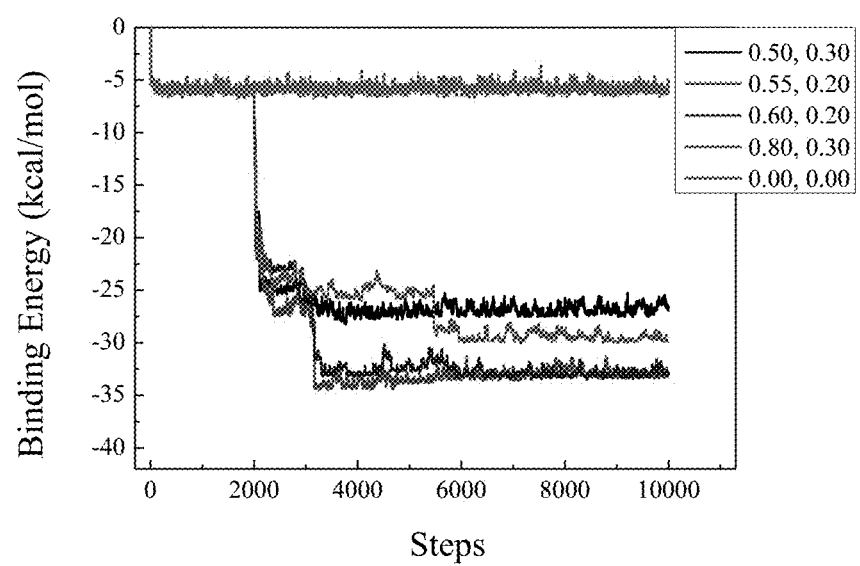

The binding energy profiles have been analyzed (FIG. 16) in regard to the number of search steps at different values of $P_{conformation}$ and $P_{sequence|conformation}$ for different sets of hydration properties: Cases One, Two and Three as listed in Table 2. The values of the energies at ($P_{conformation}$, $P_{sequence|conformation}$)≠(0.00, 0.00) are much lower than the energies at ($P_{conformation}$, $P_{sequence|conformation}$)=(0.00, 0.00) (FIG. 4). This indicates that the evolved sequences with conformational changes are much better than those with only sequence mutations. The sequences with the lowest energies for each ($P_{conformation}$, $P_{sequence|conformation}$) and each hydration property, and their corresponding binding energies are listed in Table 3. It is clear that the evolved peptide sequences at ($P_{conformation}$, $P_{sequence|conformation}$) (0.00, 0.00) are greatly improved relative to those at ($P_{conformation}$, $P_{sequence|conformation}$)=(0.00, 0.00). The global minimum in each column is highlighted in bold, exhibiting the best peptide sequence for each hydration property case. For example, the lowest binding energy in Case Two is −25.35 kcal/mol at ($P_{conformation}$, $P_{sequence|conformation}$)= (0.60, 0.20), while that in Case Three is −34.47 kcal/mol at ($P_{conformation}$, $P_{sequence|conformation}$)=(0.55, 0.20).

The lowest binding energy (kcal/mol) for each ($P_{conformation}$, $P_{sequence|conformation}$) is shown for the three cases in Table 11. The best search result in each case is highlighted in bold.

TABLE 11

| $P_{conformation}$, $P_{sequence|conformaiton}$ | Case One | Case Two | Case Three |
|---|---|---|---|
| 0.50, 0.20 | −35.32 | −25.01 | −29.73 |
| 0.50, 0.30 | −36.92 | −22.44 | −28.27 |
| 0.55, 0.20 | −30.18 | −23.42 | −34.47 |
| 0.55, 0.30 | −36.73 | −24.74 | −30.63 |
| 0.60, 0.20 | −23.32 | −25.35 | −33.51 |
| 0.60, 0.30 | −34.44 | −21.93 | −30.61 |
| 0.80, 0.20 | −35.98 | −23.40 | −31.01 |
| 0.80, 0.30 | −39.71 | −23.79 | −30.07 |
| 0.00, 0.00 | −9.83 | −7.48 | −6.79 |

Figure 17A:
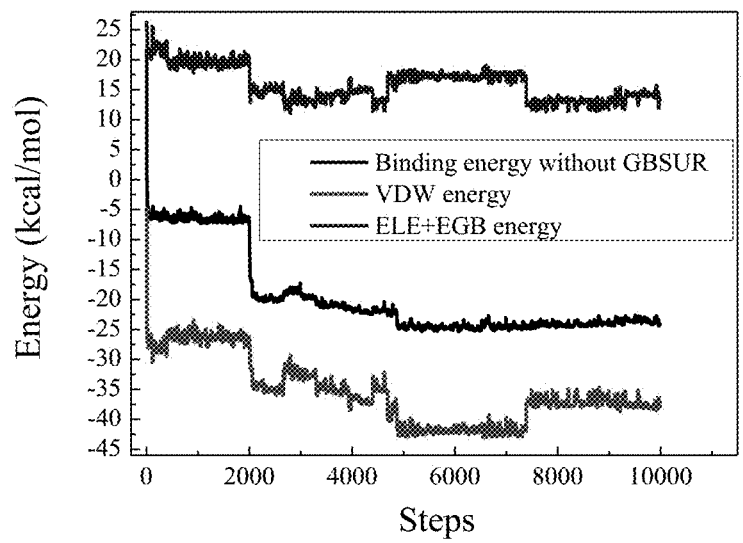
FIG. 17a-b shows the results of analysis of energy contributions in Case Two at ($P_{conformation}$, $P_{sequence|conformation}$)=(0.60, 0.20): (a) binding energy without GBSUR, the VDW energy and the (ELE+EGB) energy vs. evolution steps, (b) binding energy without GBSUR and RMSD vs. evolution steps.
Figure 17B:
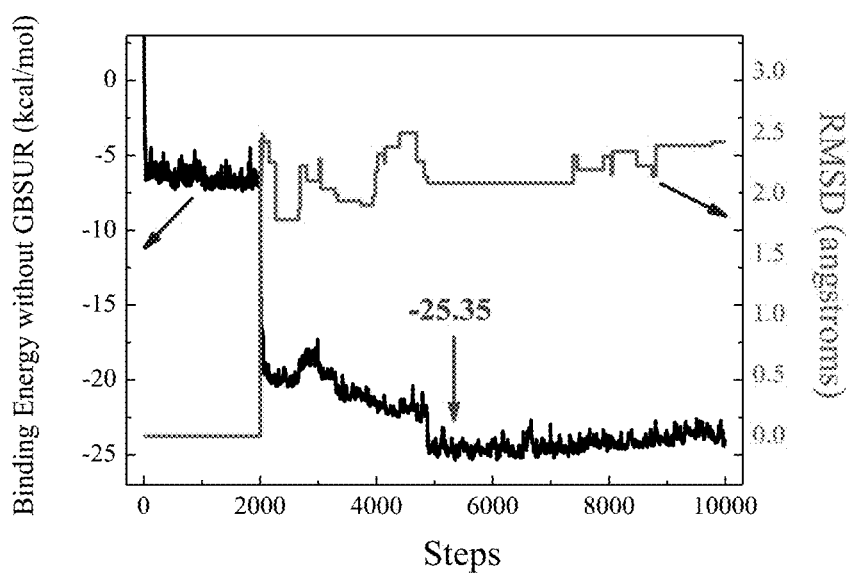

Structural and energetic analysis of the complex formed by the peptide chain and ASLLys3 can help us better understand the mechanism of binding. For example consider Case Two at ($P_{conformation}$, $P_{sequence|conformation}$)=(0.60, 0.20), the best binder for that case, FIG. 17(a) shows the binding energy without GBSUR, the VDW energy, and the sum of the ELE (electrostatic energy) and EGB (polar solvation energy) contributions to the binding free energy. The RMSD (root-mean-square deviation) has been evaluated relative to the number of steps in the search, along with the binding energy without GBSUR (FIG. 17(b)). It is apparent that the sharp drop in the binding energy as the sequence evolves is due mainly to the decline in VDW energy, while the sum of (ELE+EGB) energy shows little change (FIG. 17(a)). The binding energy without GBSUR changes in lockstep with the changes in the RMSD (FIG. 17(b)). Interestingly, the first time the binding energy has a major drop is also the time when the peptide's conformation undergoes its first major fluctuation. This means that the conformation changes make the peptide more accessible to the ASLLys3; thereby resulting in a notable improvement of binding capability. Furthermore, such improvement is a result of the decrease of VDW energy (FIG. 17 (a)) and enhances molecular recognition greatly.

We have ranked the five top-rated sequences for all three cases resulting from the search and their corresponding binding energies (Table 12). For instance, since Case One's lowest binding energy (see Table 12) is −39.71 kcal/mol at ($P_{conformation}$, $P_{sequence|conformation}$)=(0.80, 0.30), Table 11 lists this, the next four top-ranked peptide sequences at (0.80, 0.30). Also shown as the bottom line in each section of the table is the starting sequence and its binding energy without GBSUR. Examination of these top-ranked peptide sequences yields commonalities in all three cases. Some similar, even-identical amino acids occupy the same sites in the three cases, especially at sites 7, 8, 11, 12 and 13. A positively charged Arginine (R) with its long side chain is at site 7, a hydrophobic Tryptophan (W) is at site 8, and three hydrophilic amino acids, i.e. Asparagine (N), Cysteine (C) and Glutamine (Q) are at sites 11, 12 and 13, respectively. Since these sites always point towards their proximate nucleotides on ASLLys3, the amino acid side chains located at these sites have a good spatial opportunity to contact with ASLLys3. Detailed discussion of this point is given in a later section on the energy analysis.

TABLE 12

Sequences for Case One
SEQ ID NOs: 26, 27, 28, 29, 31, and 47, respectively
($P_{conformation}$ = 0.80 & $P_{sequence|conformation}$ = 0.30)

| Rank | sites | 1 | 2 | 3 | 4 | 5 | 6 | 7 | 8 | 9 | 10 | 11 | 12 | 13 | 14 | 15 | Binding Energy without GBSUR (Kcal/mol) |
|---|---|---|---|---|---|---|---|---|---|---|---|---|---|---|---|---|---|
| 1 | | P | G | M | M | T | N | R | W | T | W | N | C | Q | G | R | −39.71 |
| 2 | | P | G | M | M | S | S | R | W | H | W | N | C | Q | G | R | −39.69 |
| 3 | | P | G | N | M | S | L | R | W | S | W | N | C | Q | G | R | −39.69 |
| 4 | | P | G | M | M | T | T | R | W | T | W | N | C | Q | G | R | −39.68 |

TABLE 12-continued

| Rank | | | | | | | | | | | | | | | | Binding Energy without GBSUR (Kcal/mol) |
|---|---|---|---|---|---|---|---|---|---|---|---|---|---|---|---|---|
| 5 | P | I | G | M | S | H | R | W | T | W | N | C | Q | G | R | −39.67 |
| Initial sequence | T | W | A | K | Q | K | G | Y | V | S | C | N | N | V | G | 2.30 |

Sequences for Case Two
SEQ ID NOs: 48, 49, 50, 51, 52, and 53, respectively
($P_{conformation}$ = 0.60 & $P_{sequence|conformation}$ = 0.20)

| | sites | 1 | 2 | 3 | 4 | 5 | 6 | 7 | 8 | 9 | 10 | 11 | 12 | 13 | 14 | 15 | |
|---|---|---|---|---|---|---|---|---|---|---|---|---|---|---|---|---|---|
| 1 | | R | G | S | I | S | M | R | W | T | S | N | C | Q | I | Y | −25.35 |
| 2 | | R | G | S | V | N | M | R | W | T | N | N | C | Q | I | Y | −25.35 |
| 3 | | R | G | S | M | S | F | R | W | H | T | N | C | Q | I | Y | −25.35 |
| 4 | | R | G | S | I | S | M | R | W | T | N | N | C | Q | I | Y | −25.35 |
| 5 | | R | G | S | S | S | N | R | W | I | M | N | C | Q | I | Y | −25.34 |
| Initial sequence | | S | S | A | R | Y | T | F | V | R | S | H | T | M | F | G | 21.80 |

Sequences for Case Three
SEQ ID NOs: 54, 55, 56, 57, 58, and 59, respectively
($P_{conformation}$ = 0.55 & $P_{sequence|conformation}$ = 0.20)

| | sites | 1 | 2 | 3 | 4 | 5 | 6 | 7 | 8 | 9 | 10 | 11 | 12 | 13 | 14 | 15 | |
|---|---|---|---|---|---|---|---|---|---|---|---|---|---|---|---|---|---|
| 1 | | P | G | G | M | S | S | R | W | H | H | N | C | Q | W | P | −34.47 |
| 2 | | P | G | G | M | T | Q | R | W | S | H | N | C | Q | W | P | −34.45 |
| 3 | | P | G | T | M | T | T | R | W | T | H | N | C | P | W | G | −34.44 |
| 4 | | P | G | Q | M | S | T | R | W | G | P | N | C | Q | W | N | −34.44 |
| 5 | | P | G | T | M | G | Q | R | W | S | H | N | C | Q | W | P | −34.44 |
| Initial sequence | | P | P | T | T | F | S | G | K | Q | S | A | T | M | Y | G | 23.14 |

(b) Energy Analysis

The binding energy, the binding energy without GBSUR, the VDW energy, the sum of (ELE+EGB) energies and the GBSUR energy for the three best peptide sequences in the three cases have been compared (Table 13). Examination of the energies in Table 5 shows that the peptide sequences in the three cases exhibit notable differences in the VDW energy and the ELE+EGB energy. The different peptide's hydration properties strongly affect the charge-charge (ELE+EGB) interaction as a result of the different number of the hydrophilic or positively charged amino acids on the peptide chain. A strong VDW interaction (a relatively short-range force) means that the structures are bound together tightly. However, an excessively tight binding structure easily leads to a repulsive (positive) charge-charge (ELE+EGB) energy, thereby hindering the binding.

TABLE 13

| Cases | Binding Energy | Binding Energy without GBSUR | VDW | ELE + EGB | GBSUR |
|---|---|---|---|---|---|
| One[a] | −46.47 | −39.71 | −34.33 | −5.38 | −6.76 |
| Two[b] | −32.19 | −25.35 | −42.15 | 16.80 | −6.84 |
| Three[c] | −40.92 | −34.47 | −33.75 | −0.72 | −6.45 |

Figure 18A:
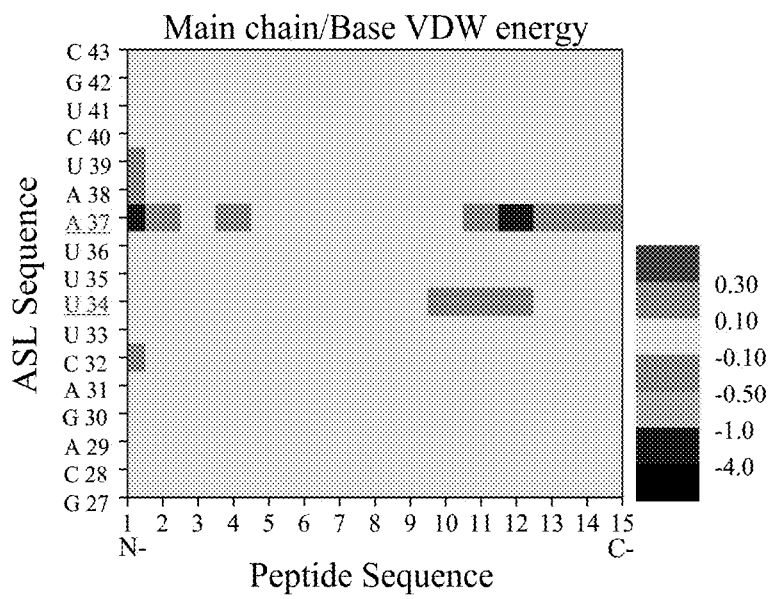
FIGS. 18a, 18b, 18c, and 18d shows maps of the VDW and ELE+EGB interactions between the main chain (backbone) of the peptide and the bases on ASLLys3 in Case One when there is no conformational change, panels (a, c), and when there is a conformational change, panels (b, d).
Figure 18B:
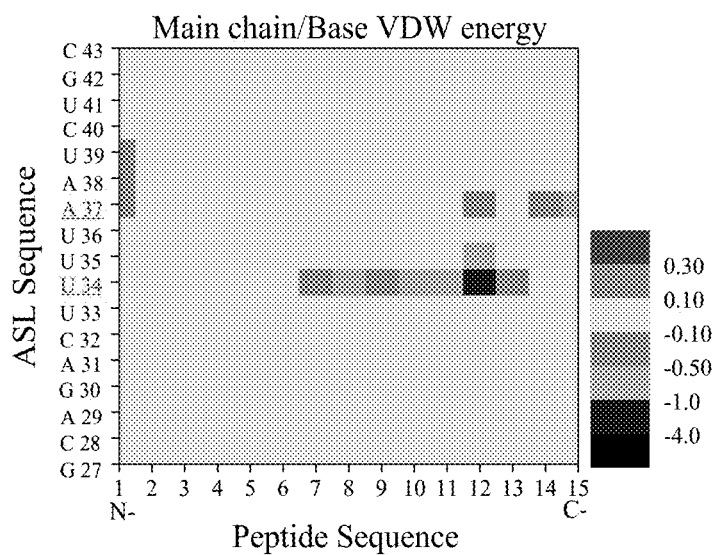
Figure 18C:
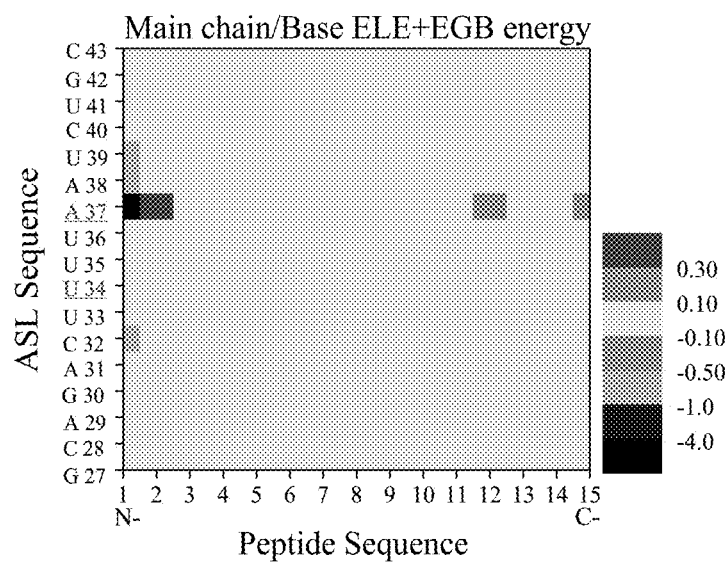
Figure 18D:
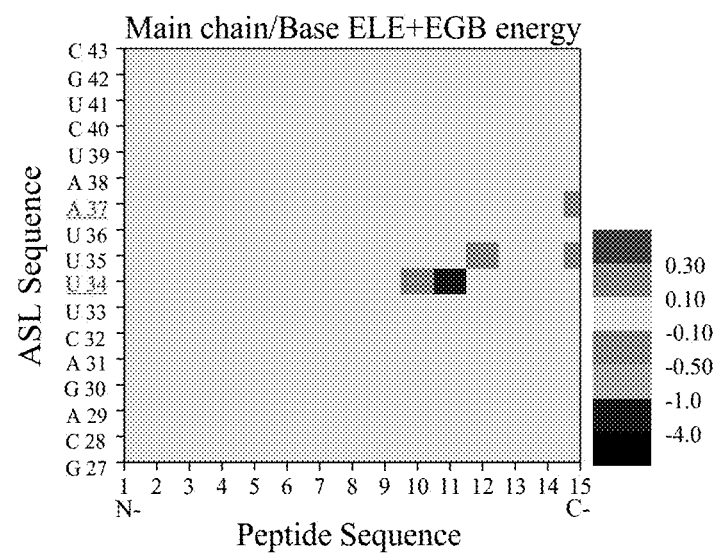
Figure 19A:
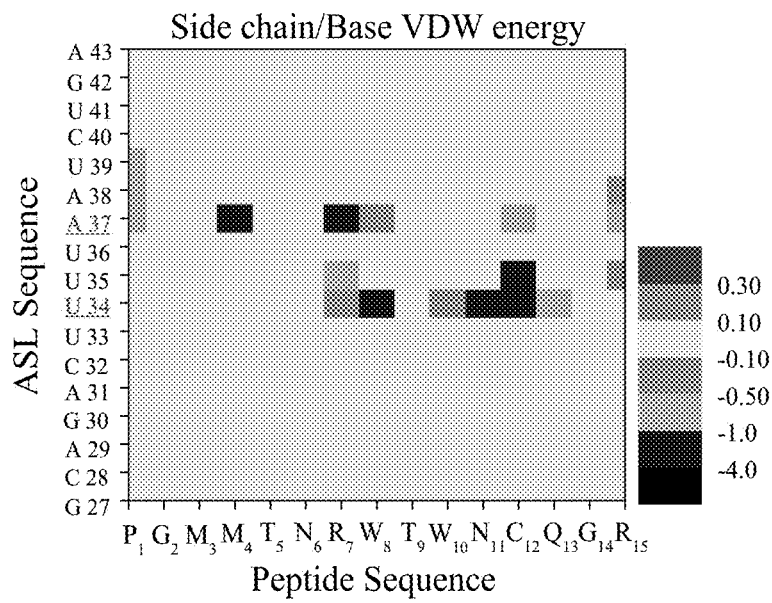
FIGS. 19a, 19b, 19c, 19d, 19e, 19f, 19g, and 19h show energy maps of interactions between side chains and ASLLys3.
Figure 19B:
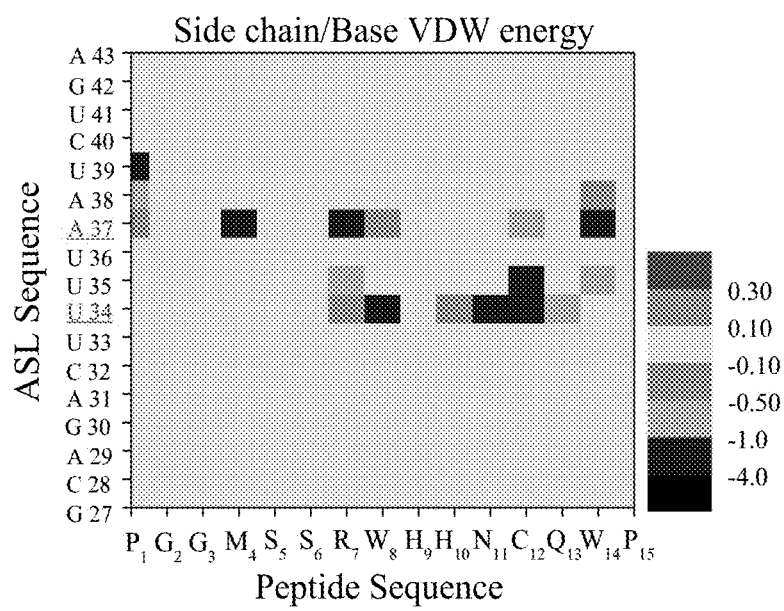
Figure 19C:
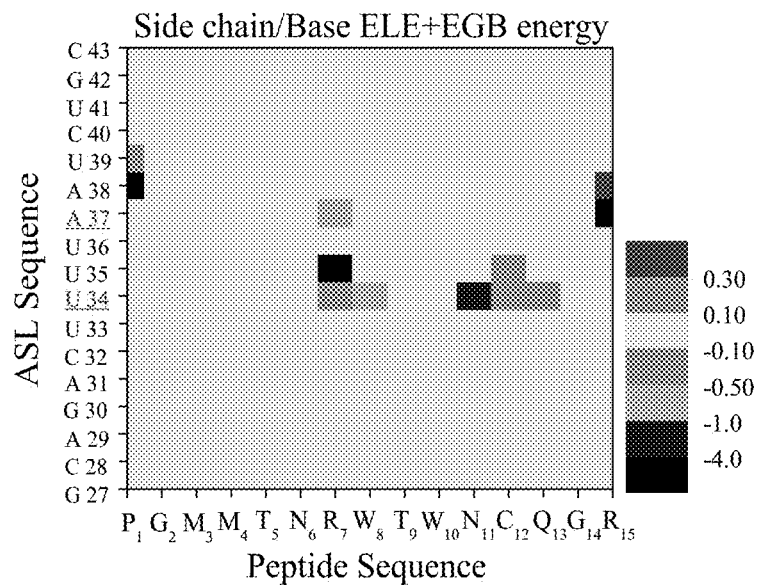
Figure 19D:
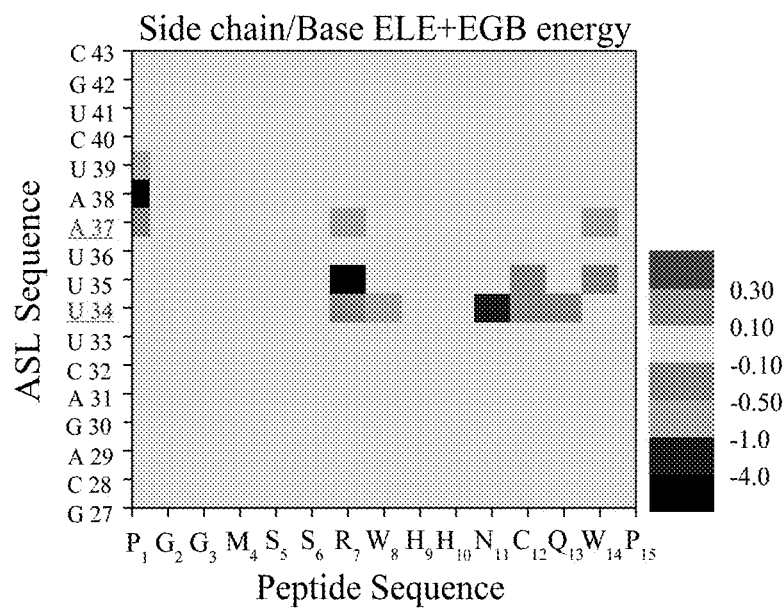
Figure 19E:
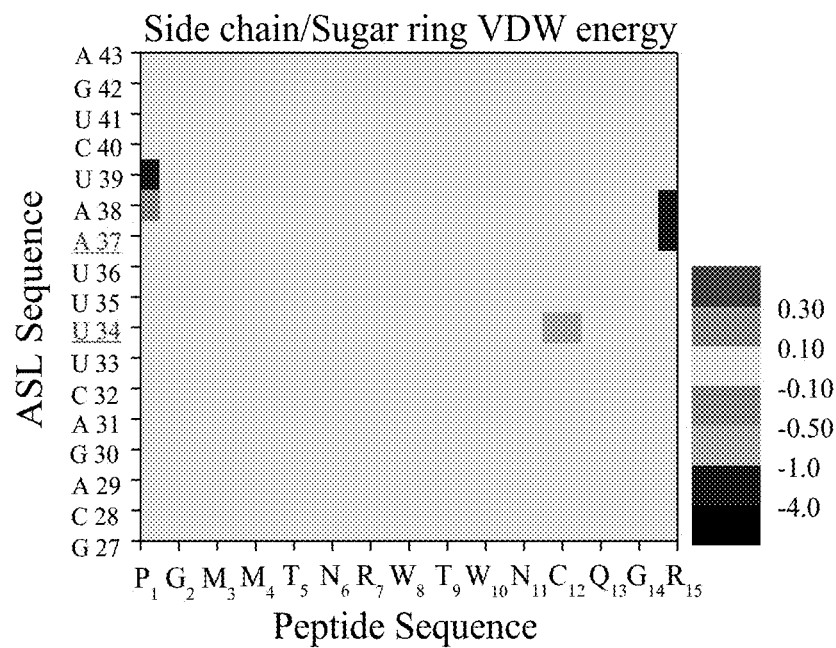
Figure 19F:
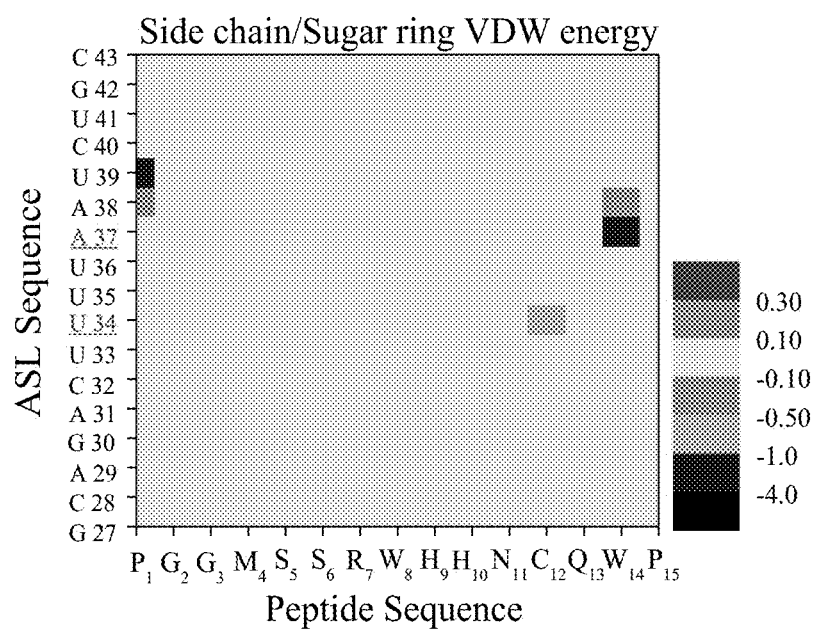
Figure 19G:
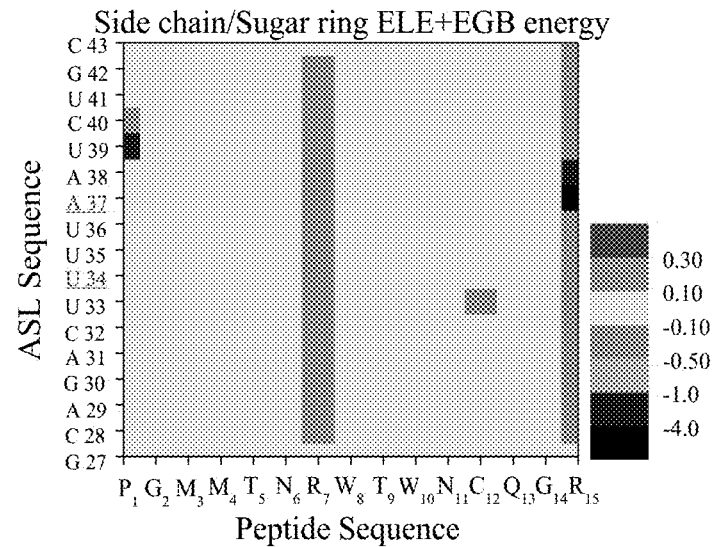
Figure 19H:
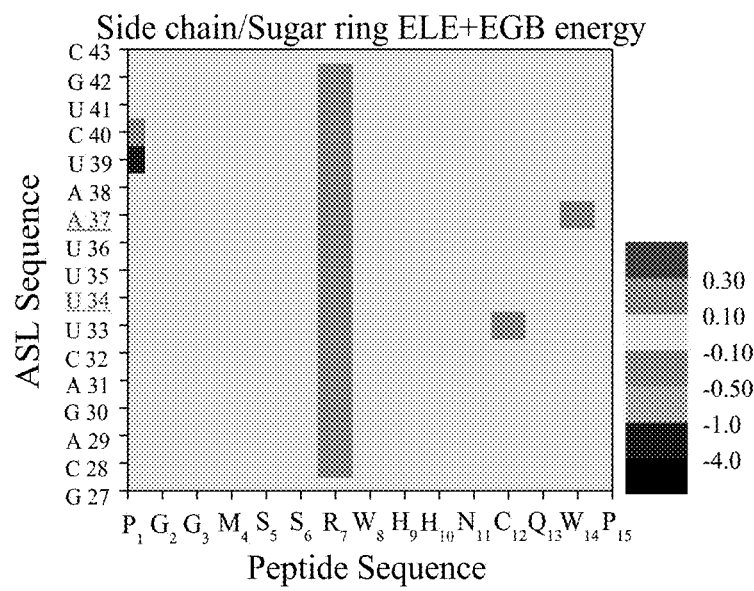

As the hybrid algorithm's ability to optimize the conformation appears to boost the binding capability of the peptide chain, a question arises: is it the conformation of the main chain (N—Cα-C) on the peptide that advances the binding capability, or is it the conformation of the side chains? To answer this question, FIG. 18 shows maps of the VDW and ELE+EGB interactions between the main chain (backbone) of the peptide and the bases on ASLLys3 in Case One when there is no conformational change, panels (a, c), and when there is a conformational change, panels (b, d). In comparing the VDW (FIG. 18 (a)) and the ELE+EGB (FIG. 18 (c)) energies of the old and new (FIG. 18 (b) and FIG. 18 (d)) peptide conformations, we observe that there is a small decrease in the VDW (FIG. 18 (b)) and the ELE+EGB (FIG. 18(d)) energies at sites (10, 11, 12, 13 and 15). This means that the interactions between the main chain near the C-terminus of the peptide and the bases of the ASLLys3 are strengthened when conformation changes are allowed. A decrease in energy implies an improvement of the binding capability of the peptide. Although the new conformation leads to a decrease in the VDW and the ELE+EGB energies between the peptide backbone and the modified ASLLys3 loop, this improvement is not sufficient to account for the improvement of the binding capability of the entire peptide chain. For example in Case One of Table 11, the binding free energy decreases from −9.83 kcal/mol when there is no conformation change to −39.71 kcal/mol when conformation changes are allowed. However, the decrease in the VDW and the ELE+EGB energies at the C-terminus for this case (approximately −5.00 kcal/mol in total) is not enough to account for the decrease in the total free energy. We conclude from this example that, although the change of the backbone conformation in the hybrid search algorithm advances the binding capability of the main chain of the peptide, the major improvement must come from the side chains because it does not come from the main chain.

To better understand the interactions between the side chains and the ASLLys3, we have compared a set of energy maps for Case One (FIG. 19 left-side panels (a, c, e and g)) with that of Case Three (FIG. 19 right-side panels (b, d, f and h)), referring to the VDW energy and the sum of the ELE+EGB energies. We first focus on the interactions (FIG. 19(a, b, c, d)) between the side chains and the bases of ASLLys3. As can be seen from the energy maps in FIG. 19(a, b), the hydrophilic amino acids at the C-terminus of the peptide interact strongly with the modified anticodon loop domain, especially with the two modified nucleotides via VDW interactions. For example, the asparagine at site 11 and the cysteine at site 12 have an intense preference for the special anticodon loop, mcm5s2U34-U35-U36-ms2t6A37. As is well known, the unique order of the bases and the unique chemistries of these two natural modifications within the anticodon loop of tRNALys3 play important roles in the virus' recruitment of the tRNA and the tRNA's annealing to the virus' primer binding site. The observation that the asparagine at site 11 and the cysteine at site 12 interact strongly with the anticodon loop implies that the two hydrophilic amino acids "recognize" ASLLys3, thereby impacting binding specificity. Next we focus on the energy interactions (FIG. 19(e, f, g, h)) between the side chains and the sugar ring/phosphate linkage of the ASLLys3. The positively charged amino acids preferentially attract the sugar ring/phosphate linkage as indicated by the charge-charge (ELE+EGB) interaction, enhancing binding affinity. For example, arginine with its positive charge attracts the phosphate linkages in ASLLys3, as shown in FIG. 19(g, h), providing a general binding capability. Other amino acids such as proline at site 1, methionine at site 4 and tryptophan at sites 8 and 14 in the peptide sequence also contribute to the binding to some extent, as shown in FIG. 19 (c, d, e, f). It is noted that to have good binding the sequence not only needs the key amino acids, but also needs a good folded conformation, which can effectively promote and enhance the binding specificity and affinity for the key amino acids.

(c) Conformation Analysis

Figure 20:
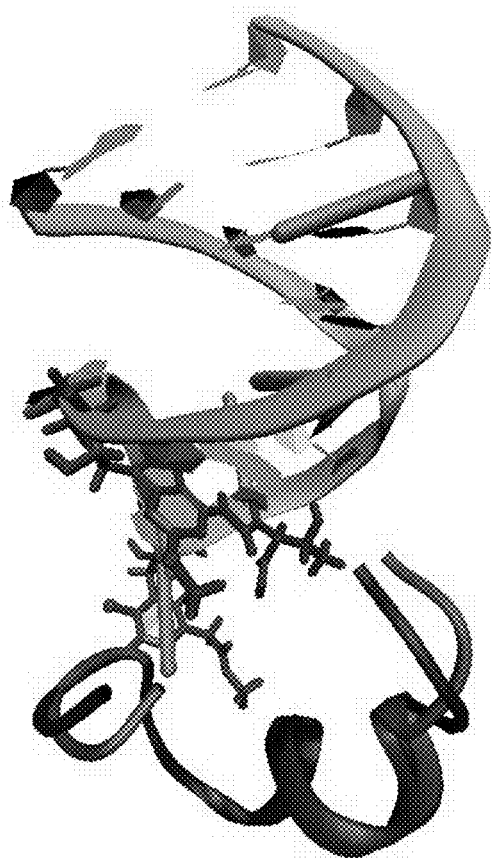
FIG. 20 shows complexes formed by ASLLys3 and the peptide chain obtained in the hybrid search algorithm with and without the conformation changes.

The complexes formed by ASLLys3 and the peptide chain obtained in the hybrid search algorithm with and without the conformation changes are shown in FIG. 20. The red ribbon is the initial conformation and the blue ribbon represents a new folded conformation of the peptide chain. It can be seen that the helix in the middle of the peptide remains at its original position, but both ends move freely in a β-strand configuration. The helix region stacks on the C32, U33, ms2t6A37 and A38 of the ASLLys3, serving as a strong "anchor" to provide binding affinity. In contrast, the strand regions prefer interacting with the mcm5s2U34-U35-U36-ms2t6A37 region of the anticodon loop domain, serving as a strong "recognizer" to provide binding specificity. When performing the hybrid search algorithm to evolve the sequences, we found that the helix region is usually stable and retains its folded structure but the strand region is always flexible and easily adjusts its conformation. This is consistent with the experimental observations by Xia et al. who used a combination of fluorescence up-conversion and transient absorption and found that the complex formed by the antiterminator N protein and the stem-loop RNA hairpin exists in a dynamic equilibrium. Experimentally, the N-terminal helical domain of the bound peptide always stacks with the RNA, but the C-terminal helical domain undergoes a change of conformation between stacked and unstacked states. Zhang and the coworkers utilized site-directed spin labeling to examine the conformation distributions at the interface between a peptide and a stem-loop RNA element. They observed that the C-terminal fragment of the bound peptide tends to adopt multiple discrete conformations in the complex.

To obtain a better understanding of the differences the two search algorithms we compared properties for two sequences from Case One, viz. PGMMTNRWTWNCQGR (SEQ ID NO:26) and PHWRTTGWMNNCRMG (SEQ ID NO:17) which are obtained from each of the search algorithms. Their conformational properties, including <Rg2> (mean square radius of gyration), the SASA (solvent accessible surface area), the GBSUR energy (non-polar solvation energy), the VDW energy, the ELE+EGB energy and the binding energy without GBSUR have been compared (Table 14). Allowing conformational changes results in an increase of the <Rg2> of the peptide's main chain from 44.25 to 48.88, and an increase in the corresponding SASA from 1989.02 A2 to 2158.44 A2. This indicates that the folded chain has elongated its structure and exposed more previously-hidden surface area to ASLLys3. This, of course, causes an increase in the molecular interaction between peptide chain and the ASLLys3, as is verified by the fact that the GBSUR energy becomes a little lower when the conformation is changed. The lower GBSUR energy as a result of the increased molecular interaction between the peptide chain and ASLLys3 indicates that the binding conformation of the complex obtained in the new search algorithm is tighter. The notable decrease in the VDW energy from −27.59 kcal/mol (old binding conformation) to −34.33 kcal/mol (new binding conformation) indicates improved recognition of the peptide for the ASLLys3. The sizeable decrease in the ELE+EGB energy from 17.75 kcal/mol (old binding conformation) to −5.38 kcal/mol (new binding conformation) also results in a significant improvement in the binding capability of the peptide to the ASLLys3, as shown in the binding energy without GBSUR (Table 14). We conclude that the new hybrid search algorithm is able to sample effectively the conformational space and to find better conformations and sequences than the old search algorithm.

A comparison of the conformational properties of the best sequence with conformational changes (PGMMT-NRWTWNCQGR, SEQ ID NO:26) and without conformational changes (PHWRTTGWMNNCRMG, SEQ ID NO:17) in Case One is shown in Table 14.

TABLE 14

|  | Best sequence without conformation changes | Best sequence with conformation changes |
|---|---|---|
| $<Rg^2>$ | 44.25 | 48.88 |
| SASA ($Å^2$) | 1989.02 | 2158.44 |
| GBSUR (kcal/mol) | −5.63 | −6.76 |
| VDW (kcal/mol) | −27.59 | −34.33 |
| ELE + EGB (kcal/mol) | 17.75 | −5.38 |
| Binding Energy without GBSUR (kcal/mol) | −9.83 | −39.71 |

Materials and Reagents

All materials, buffers, and reagents were of RNA grade quality and RNase free. The modified and unmodified hASL$^{Lys3}_{UUU}$ were chemically synthesized by Thermo Scientific. The modified hASL$^{Lys3}_{UUU}$ was synthesized with the nucleoside phosphoramidites that were 2'-protected with tert-butyldimethylsilyl-ether (9). The unmodified hASL$^{Lys3}_{UUU}$ was synthesized with "ACE" chemistry (37). All fluorescein labeled peptides were obtained from Sigma-Aldrich (PEPscreen).

In Silico Evolution of Peptide Sequences

A random initial sequence that satisfies the constraints on hydration properties is generated (FIG. 2). For the search described here, we started with the 15-amino-acid sequence of peptide P6, RVTHHAFLGAHRTVG (SEQ ID NO:2), found experimentally to bind selectively to the modified hASLLys3UUU. The peptide backbone conformation is determined via atomistic simulation of the peptide-hASLLys3UUU complex and then held fixed with respect to the hASLLys3UUU conformation throughout the search. The binding free energy for the complex is then evaluated. Subsequently, a random number is generated to determine whether to mutate one amino acid or to exchange two amino acids. If one amino acid is to be mutated, one site along the peptide sequence is chosen randomly. The amino acid at that site is then mutated to another amino acid of the same residue type. The best rotamer for the new amino acid is chosen to substitute for the old amino acid in this mutation step. If an exchange step is chosen, two random sites along the chain and their corresponding amino acids are chosen for a mutual exchange attempt. In this exchange step, we calculate the effective potential of all the possible rotamers and perform the Self-Consistent Mean Field (SCMF) procedure described below to obtain the best rotamer combination for the exchanged amino acids. Regardless of whether one amino acid was mutated or two amino acids were exchanged, the new generated peptide sequence is evaluated further by calculating the new binding free energy and accepted or rejected according to the Metropolis criterion. After a total of 10,000 evolution steps, the best peptide sequences with the lowest binding free energy are identified.

In our use of the SCMF, a trial exchange between two amino acids at randomly-chosen sites is implemented (FIG. 3). The conformational probability matrix P=P0 is set initially for the two amino acids so that all possible rotamers have equal conformational probability. The initial conformational matrix P0 is then used to calculate the effective potential of each amino acid in each rotamer state. Once the effective potentials for all the rotamer states are known, new conformational probabilities of the rotamers are obtained according to the Boltzmann law so as to constitute a new conformational matrix P1. Next, the absolute error between P1 and P0 is calculated. If the absolute error is less than 10-3, the best rotamers with the highest conformational probability for the two amino acids are selected from P1 to repack the side chains. Otherwise, the conformational matrix P is updated by employing a self-consistent iteration. The updated conformation matrix P is stored as the old conformational matrix P0 for the next round evaluation. The conformational matrix is iterated until the absolute error between P1 and P0 is less than 10-3. Eventually, the best combination of rotamers is found, thereby repacking the backbone.

Fluorescein-Labeled Peptides

Fifteen-amino acid peptides were selected from the sequences predicted in silico and were chemically synthesized, each with fluorescein (Flc) at the N-terminus. This set of peptides included the original P1 and P6 sequences to be used as an internal control. The lyophilized peptide set was reconstituted via standard suggestions from the manufacturer (80% DMSO:20% H2O, v/v). Concentrated peptide stocks were stored in 25 µl aliquots at −8° C. for later use. Working concentrations were diluted for each experiment and kept on ice or stored at −20° C.

Fluorescent Assays

Fluorescent assays were conducted in phosphate buffer (10 mM Na2HPO4 and 10 mM KH2PO4, pH 6.8) in low volume 384 well plates. All buffers, peptides, and RNA were pipetted into wells via a liquid handling robot (Janus, PerkinElmer). All plates were read using a plate reader fitted with fluorescein specific filters (PerkinElmer EnVision) which was optimized for each plate and peptide before each experiment. Initial validation screens were conducted by obtaining fluorescent signals for each peptide (0.50 µM) alone (FS0) and in the presence of a 2-fold excess of modified or unmodified hASLLys3UUU (FS1). Percent change in fluorescent signal was calculated (% Change=100*(FS1/FS0)). A decrease (quench) in fluorescent signal in the presence of RNA indicated a binding event between the peptide and ASL. In control wells H2O, phosphate buffer, and ASLs were individually tested for any inherent fluorescent signal. Water and buffer signals served as blank background signals. The hASLLys3UUU had a negligible inherent signal which was taken into account when calculating the overall signal quench. All controls and experimental sets were repeated in triplicate within a single plate and signals are an average of each triplicate. For the subset of peptides which were further studied to obtained binding constants, the fluorescent binding assay was completed as above. The peptide fluorescent signal was monitored throughout an increasing ASL concentration (0-3 µM). The percent quench in signal was plotted against the hASL concentration. Binding constants (Kd) were calculated using the single linear regression function within SigmaPlot. Experiments were performed in triplicate within a single plate and fluorescent signals are an average of each triplicate.

In summary, the present invention relates to search algorithms designed to identify peptide sequences (potential drug candidates) that are expected to have good binding capability to the anticodon stem and loop of tRNA$^{Lys3}$ and are ultimately used for breaking the replication cycle of HIV-1 virus. Two initial binding conformations, Complexes 1 and 2, obtained from atomistic simulations of the initial sequence, RVTHHAFLGAHRTVG, (selected from phage display peptide libraries) and ASL$^{Lys3}$ were considered. By comparing the binding sequences that resulted after Complexes 1 and 2 were subjected to the search algorithm it was discovered that the peptide sequence evolved from Complex 1 binds to the $ASL^{Lys3}$ better than the peptide sequence evolved from Complex 2. Without wishing to be bound by theory, this is likely due to the fact that Complex 1 has a looser binding configuration than Complex 2 Sequences evolved from a relatively loose binding configuration seem to have more freedom to explore the chemical and physical space between the peptide's backbone scaffold and $ASL^{Lys3}$, allowing accommodation of the best rotamers or rotamer combination, and making it easier to evolve to a good peptide sequence.

The mechanisms underlying the binding behavior between the evolved peptide and $ASL^{Lys3}$ were explored and the impact of the peptide's hydration properties on the binding was considered. The latter was accomplished by constraining the number of amino acids of different residue types; three cases were considered. After analyzing the binding energy of the peptide evolved from the search algorithm, several key amino acids were found to favor binding. Their roles, however, are completely different; some are necessary for binding affinity and others are necessary for binding specificity to the $ASL^{Lys3}$. By plotting maps of the contributions to the binding energy for the various interactions between the nucleotides on $ASL^{Lys3}$ and the side chains on the peptide, it was deduced that 1) asparagine (ASN) at site 11 and cysteine (CYS) at site 12 "recognize" the $ASL^{Lys3}$ due to the VDW energy, contributing to the binding specificity; and that 2) two positively charged arginines at sites 4 and 13 preferentially attract the sugar rings and the phosphate linkages (which are themselves negatively charged) due to the charge-charge interaction, implying that they are responsible for the binding affinity.

The approach described here is a feasible strategy for selecting amino acid sequences with enhanced specificity and affinity as RNA binding peptides.

REFERENCES

[1] P. J. Norris and E. S. Rosenberg. Cellular immune response to human immunodeficiency virus. *AIDS*, 2001, 15, S16-S21.

[2] World Health Organization. Antiretroviral Therapy for HIV Infection in Adults and Adolescents Recommendations for a public health approach. 2010: 1-145. ISBN: 9289241599764.

[3] D. Werb, E. J. Mills, J. S. G Montaner, E. Wood. Risk of resistance to highly active antiretroviral therapy among HIV-positive injecting drug users: a meta-analysis. *The Lancet Infectious Diseases*, 2010, 10(7): 464-469.

[4] L. Kleiman, S. Caudry, F. Boulerice, M. A. Wainberg, M. A. Parniak. Incorporation of tRNA into normal and mutant HIV-1. *Biochem. Bioph. Res. Co.*, 1991, 174(3): 1272-1280.

[5] R. Marquet, C. Isel, C. Ehresmann, B. Ehresmann. tRNA as primer of reverse transcriptases. *Biochimie*, 1995, 77(1-2): 113-124.

[6] C. Tisné, B. P. Rogues, F. Dardel. Specific recognition of primer $tRNA^{Lys}{}_3$ by HIV-1 nucleocapsid protein: involvement of the zinc fingers and the N-terminal basic extension. *Biochimie*, 2003, 85(5): 557-561.

[7] P. Barraud, C. Gaudin, F. Dardel, C. Tisne. New insights into the formation of HIV-1 reverse transcription initiation complex. *Biochimie*, 2007, 89(10): 1204-1210.

[8] E. V. Puglisi, J. D. Puglisi. Secondary Structure of the HIV Reverse Transcription Initiation Complex by NMR. *J. Mol. Biol.*, 2011, 410(5): 863-874.

[9] C. Tisné. Structural Bases of the Annealing of Primer $tRNA^{Lys3}$ to the HIV-1 Viral RNA. *Curr. HIV Res.*, 2005, 3(2): 147-156.

[10] J. M. Watts, K. K. Dang, R. J. Gorelick, C. W. Leonard, J. W. Bess Jr, R. Swanstrom, C. L. Burch and K. M. Weeks. Architecture and secondary structure of an entire HIV-1 RNA genome. *Nature*, 2009, 460: 711-716.

[11] C. Isel, C. Ehresmann and R. Marquet. Initiation of HIV Reverse Transcription. *Viruses*, 2010, 2: 213-243.

[12] M. Guo, R. Shapiro, G M. Morris, X. Yang, and P. Schimmel. Packaging HIV Virion Components through Dynamic Equilibria of a Human tRNA Synthetase. *J. Phys. Chem. B*, 2010, 114(49): 16273-16279.

[13] M. Eshete, M. T. Marchbank, S. L. Deutscher, B. Sproat, G Leszcynska, A. Malkiewicz and P. F. Agris. Specificity of Phage Display Selected Peptides for Modified Anticodon Stem and Loop Domains of tRNA. *The Protein J.*, 2007, 26(1): 61-73.

[14] W. D. Graham, L. Barley-Maloney, C. J. Stark, A. Kaur, K. Stolyarchuk, B. Sproat, G Leszczynska, A. Malkiewicz, N. Safwat, P. Mucha, R. Guenther and P. F. Agris. Functional recognition of the modified human $tRNA^{Lys3}{}_{UUU}$ anticodon domain by HIV's nucleocapsid protein and a peptide mimic. *J. Mol. Biol.*, 2011, 410(4): 698-715.

[15] I. Halperin, B. Ma, H. Wolfson, and R. Nussinov. Principles of Docking: An Overview of Search Algorithms and a Guide to Scoring Functions. *Proteins*, 2002, 47(4): 409-443.

[16] S. M. Lippow, B. Tidor. Progress in computational protein design. *Curr. Opin. Biotech.*, 2007, 18(4): 305-311.

[17] I. Samish, C. M. MacDermaid, J. M. Perez-Aguilar, and J. G Saven. Theoretical and Computational Protein Design. *Annu. Rev. Phys. Chem.*, 2011, 62: 129-149.

[18] L. Jiang, E. A. Althoff, F. R. Clemente, L. Doyle, D. Rothlisberger, A. Zanghellini, J. L. Gallaher, J. L. Betker, F. Tanaka, C. F. Barbas III, D. Hilvert, K. N. Houk, B. L. Stoddard and D. Baker. De Novo Computational Design of Retro-Aldol Enzymes. *Science*, 2008, 319: 1387-1391.

[19] J. Ashworth, J. J. Havranek, C. M. Duarte, D. Sussman, R. J. Monnat Jr, B. L. Stoddard, and D. Baker. Computational redesign of endonuclease DNA binding and cleavage specificity. *Nature*, 2006, 441: 656-659.

[20] G Ofek, F. J. Guenaga, W. R. Schief, J. Skinner, D. Baker, R. Wyatt, and P. D. Kwong. Elicitation of structure-specific antibodies by epitope scaffolds. *PNAS*, 2010, 107: 17880-17887.

[21] B. I. Dahiyat and S. L. Mayo. De Novo Protein Design: Fully Automated Sequence Selection. *Science*, 1997, 278: 82-87.

[22] C. A. Voigt, D. B. Gordon and S. L. Mayo. Trading Accuracy for Speed: A Quantitative Comparison of Search Algorithms in Protein Sequence Design. *J. Mol. Biol.*, 2000, 299: 789-803.

[23] K. T. Simons, R. Bonneau, I. Ruczinski, D. Baker. Ab initio protein structure prediction of CASP III targets using ROSETTA. *Proteins*, 1999, 37: 171-176.

[24] K. T. Simons, I. Ruczinski, C. Kooperberg, B. A. Fox, C. Bystroff, and D. Baker. Improved Recognition of Native-Like Protein Structures Using a Combination of Sequence-Dependent and Sequence-Independent Features of Proteins. *Proteins*, 1999, 34: 82-95.

[25] J. Zhou and J. G Saven. Statistical Theory of Combinatorial Libaries of Folding Proteins: Energetic Discrimination of a Target Structure. *J. Mol. Biol.,* 2000, 296: 281-294.

[26] J. Tang, S. Kang, J. G Saven and F. Gai. Characterization of the Cofactor-Induced Folding Mechanism of a Znic-Binding Peptide Using Computationally Designed Mutants. *J. Mol. Biol.,* 2009, 389: 90-102.

[27] F. V. Cochran, S. P. Wu, W. Wang, V. Nanda, J. G Saven, M. J. Therien, and W. F. DeGrado. Computational De Novo Design and Characterization of a Four-Helix Bundle Protein that Selectively Binds a Nonbiological Cofactor. *J. Am. Chem. Soc.,* 2005, 127(5): 1346-1347.

[28] J. Desmet, M. D. Maeyer, B. Hazes and I. Lasters. The dead-end elimination theorem and its use in protein side-chain positioning. *Nature,* 1992, 356: 539-542.

[29] D. T. Jones. De novo protein design using pairwise potentials and a genetic algorithm. *Protein Sci.,* 1994, 3: 567-574.

[30] C. Wang, P. Bradley and D. Baker. Protein-Protein Docking with Backbone Flexibility. *J. Mol. Biol.,* 2007, 373: 503-519.

[31] S. Chaudhury and J. J. Gary. Conformer Selection and Induced Fit in Flexible Backbone Protein-Protein Docking Using Computational and NMR Ensembles. *J. Mol. Biol.,* 2008, 381: 1068-1087.

[32] I. Georgiev, D. Keedy, J. S. Richardson, D. C. Richardson and B. R. Donald. Algorithm for backrub motions in protein design. *Bioinformatics,* 2008, 24: i196-i204.

[33] D. J. Mandell and T. Kortemme. Backbone flexibility in computational protein design. *Curr. Opin. Chem. Biol.,* 2009, 20: 420-428.

[34] M. A. Hallen, D. A. Keedy, and B. R. Donald. Dead-end elimination with perturbations (DEEPer): A provable protein design algorithm with continuous sidechain and backbone flexibility. *Proteins,* 2013, 81: 18-39.

[35] B. E. Correia, Y. A. Ban, D. J. Friend, K. Ellingson, H. Xu, E. Boni, T. Bradley-Hewitt, J. F. Bruhn-Johannsen, L. Stamatatos, R. K. Strong, and W. R. Schief. Computational Protein Design Using Flexible Backbone Remodeling and Resurfacing: Case Studies in Structure-Based Antigen Design. *J. Mol. Biol.,* 2011, 405: 284-297.

[36] J. Karanicolas, J. E. Corn, I. Chen, L. A. Joachimiak, O. Dym, S. H. Peck, S. Albeck, T. Unger, W. Hu, G Liu, S. Delbecq, G T. Montelione, C. P. Spiegel, D. R. Liu and D. Baker. A De Novo Protein Binding Pair by Computational Design and Directed Evolution. *Mol. Cell,* 2011, 42: 1-11.

[37] I. W. Davis, W. B. Arendall, D. C. Richardson, J. S. Richardson. The backrub motion: how protein backbone shrugs when a sidechain dances. *Structure,* 2006, 14(2): 265-274.

[38] C. A. Smith and T. Kortemme. Backrub-Like Backbone Simulation Recapitulates Natural Protein Conformational Variability and Improves Mutant Side-Chain Prediction. *J. Mol. Biol.,* 2008, 380: 742-756.

[39] C. A. Rohl, C. E. M. Strauss, D. Chivian and D. Baker. Modeling Structurally Variable Regions in Homologous Proteins with Rosetta. *Proteins,* 2004, 55: 656-677.

[40] B. S. Chevalier, T. Kortemme, M. S. Chadsey, D. Baker, R. J. Monnat Jr, B. L. Stoddard. Design, Activity, and Structure of a Highly Specific Artificial Endonuclease. *Mol. Cell,* 2002, 10(4): 895-905.

[41] P. S. Huang, J. J. Love, S. L. Mayo. A de novo designed protein-protein interface. *Protein Sci.,* 2007, 16(12): 2770-2774.

[42] L. Wang, E. A. Althoff, J. Bolduc, L. Jiang, J. Moody, J. K. Lassila, L. Giger, D. Hilvert, B. Stoddard and D. Baker. Structural Analyses of Covalent Enzyme-Substrate Analog Complexes Reveal Strengths and Limitations of De Novo Enzyme Design. *J. Mol. Biol.,* 2012, 415: 615-625.

[43] J. N. Haidar, B. Pierce, Y. Yu, W. Tong, M. Li and Z. Weng. Structure-based design of a T-cell receptor leads to nearly 100-fold improvement in binding affinity for pepMHC. *Proteins,* 2009, 74: 948-960.

[44] G Stracquadanio, G Nicosia. Computational energy-based redesign of robust proteins. *Comput. Chem. Eng.,* 2011, 35(3): 464-473.

[45] S. M. Lewis, B. A. Kuhlman. Anchored Design of Protein-Protein Interfaces. *PLos ONE,* 2011, 6(6): e20872-14.

[46] T. Hou and X. Xu. A new molecular simulation software package—Peking University Drug Design System (PKUDDS) for structure-based drug design. *J. Mol. Graph. Model.,* 2001, 19: 455-465.

[47] D. J. Mandell, T. Kortemme. Computer-aided design of functional protein interactions. *Nat. Chem. Biol.,* 2009, 5(11): 797-807.

[48] J. J. Gray, S. Moughon, C. Wang, O. Schueler-Furman, B. Kuhlman, C. A. Rohl and D. Baker. Protein-Protein Docking with Simultaneous Optimization of Rigid-body Displacement and Side-chain Conformations. *J. Mol. Biol.,* 2003, 331: 281-299.

[49] C. Wang, R. Vernon, O. Lange, M. Tyka and D. Baker. Prediction of structures of zinc-binding proteins through explicit modeling of metal coordination geometry. *Protein Sci.,* 2010, 19: 494-506.

[50] C. Schmitz, R. Vernon, G Otting, D. Baker and T. Huber. Protein Structure Determination from Pseudocontact Shift Using ROSETTA. *J. Mol. Biol.,* 2012, 416: 668-677.

[51] D. W. Sammond, D. E. Bosch, G L. Butterfoss, C. Purbeck, M. Machius, D. P. Siderovski, and B. Kuhlman. Computational Design of the Sequence and Structure of a Protein-Binding Peptide. *J. Am. Chem. Soc.,* 2011, 133: 4190-4192.

[52] R. K. Jha, A. Leaver-Fay, S. Yin, Y. Wu, G L. Butterfoss, T. Szyperski, N. V. Dokholyan, and B. Kuhlman. Computational Design of a PAK1 Binding Protein. *J. Mol. Biol.,* 2010, 400: 257-270.

[53] G Guntas, C. Purbeck, and B. Kuhlman. Engineering a protein-protein interface using a computationally designed library. *PNAS,* 2010, 107(45): 19196-19301.

[54] G S. Murphy, J. L. Mills, M. J. Miley, M. Machius, T. Szyperski, and B. Kuhlman. Increasing Sequence Diverstiy with Flexible Backbone Protein Design: The Complete Redesign of a Protein Hydrophobic Core. *Structure,* 2012, 20: 1086-1096.

[55] X. Xiao, C. K. Hall and P. F. Agris. The design of a peptide sequence to inhibit HIV replication: a search algorithm combining Monte Carlo and self-consistent mean field techniques. *J. Biomol. Struct. Dyn.,* DOI: 10.1080/07391102.2013.825757.

[56] G N. Ramachandran, C. Ramakrishnan, V. Sasisekharan. Stereochemistry of polypeptide chain configurations. *J. Mol. Biol.,* 1963, 7(1), 95-99.

[57] G N. Ramachandran, V. Sasisekharan. Conformation of polypeptides and proteins. *Adv. Protein Chem.,* 1968, 23, 284-438.

[58] S. C. Lovell, I. W. Davis, W. B. Arendall III, P. I. W. de Bakker, J. M. Word, M. G Prisant, J. S. Richardson and D. C. Richardson. Structure Validation by Cα Geometry: φ, ψ and Cβ Deviation. *Proteins,* 2003, 50, 437-450.

[59] M. Cheon, I. Chang, and C. K. Hall. Extending the PRIME model for protein aggregation to all 20 amino acids. *Proteins,* 2010, 78: 2950-2960.

[60] X. Xiao, P. F. Agris and C. K. Hall, Molecular Recognition Mechanism of Peptide Chain Bound to the

[60] tRNA$^{Lys3}$ Anticodon Loop in silico. *J. Biomol. Struct. Dyn.*, DOI: 10.1080/07391102.2013.869660.

[61] P. Koehl, and M. Delarue. Application of a Self-consistent Mean Field Theory to Predict Protein Sidechains Conformation and Estimate Their Conformational Entropy. *J. Mol. Biol.*, 1994, 239: 249-275.

[62] P. Koehl, and M. Levitt. De Novo Protein Design. I. In Search of Stability and Specificity. *J. Mol. Biol.*, 1999, 293: 1161-1181.

[63] S. C. Lovell, J. M. Word, J. S. Richardson and D. C. Richardson. The Penultimate Rotamer Library. *Proteins*, 2000, 40: 389-408.

[64] G D. Hawkins, C. J. Cramer, and D. G Truhlar. Parametrized Models of Aqueous Free Energies of Solvation Based on Pairwise Descreening of Solute Atomic Charges from a Dielectric Medium. *J. Phys. Chem.*, 1996, 100: 19824-19839.

[65] B. Jayaram, Y. Liu and D. L. Beveridge. A modification of the generalized Born theory for improved estimates of solvation energy and pK shifts. *J. Chem. Phys.*, 1998, 109(4): 1465-1471.

[66] B. Jayaram, D. Sprous and D. L. Beveridge. Solvation Free Energy of Biomacromolecules: Parameters for a Modified Generalized Born Model Consistent with the AMBER Force Field. *J. Phys. Chem. B*, 1998, 102(47): 9571-9576.

[67] A. Onufriev, D. Bashford, and D. A. Case. Modification of the Generalized Born Model Suitable for Macromolecules. *J. Phys. Chem. B*, 2000, 104(15): 3712-3720.

[68] H. Gohlke, C. Kiel and D. A. Case. Insights into Protein-Protein Binding by Binding Free Energy Calculation and Free Energy Decomposition for the Ras-Raf and Ras-RalGDS Complexes. *J. Mol. Biol.*, 2003, 330: 891-913.

[69] L. R. Dodd, T. D. Boone and D. N. Theodorou. A concerted rotation algorithm for atomistic Monte Carlo simulation of polymer melts and glasses. *Mol. Phys.*, 1993, 78(4): 961-996.

[70] J. P. Ulmschneider and W. L. Jorgensen. Polypeptide Folding Using Monte Carlo Sampling, Concerted Rotation, and Continuum Solvation. *J. Am. Chem. Soc.*, 2004, 126: 1849-1857.

[71] T. Xia, C. Wan, R. W. Roberts and A. H. Zewail. RNA-protein recognition: Single-residue ultrafast dynamical control of structural specificity and function. *PNAS*, 2005, 102(37): 13013-13018.

[72] X. Zhang, S. W. Lee, L. Zhao, T. Xia and P. Z. Qin. Conformational distributions at the N-peptide/boxB RNA interface studied using site-directed spin labeling. *RNA*, 2010, 16: 2474-2483.

[73] J. L. Spears, X. Xiao, C. K. Hall, and P. F. Agris. Amino acid signature enables proteins to recognize modified tRNA. *Biochemistry*, 2014, 53: 1125-1133.

[74] Joint United Nations Programme on HIV/AIDS. Overview of the global AIDS epidemic. 2006 *Report on the global AIDS epidemic*, 2006, 8-50.

[75] A statistic report on the top ten deadliest diseases in the world. *World Health Organization*, 2008.

[76] F. A. P. Vendeix, A. Dziergowska, E. M. Gustilo, W. D. Graham, B. Sproat, A. Malkiewicz, and P. F. Agris. Anticodon Domain Modifications Contribute Order to tRNA for Ribosome-Mediated Codon Binding. *Biochemistry*, 2008, 47(23): 6117-6129.

[77] Y. Hou, X. Zhang, J. A. Holland and D. R. Davis. An important 2'—OH group for an RNA-protein interaction. *Nucleic Acids Res.*, 2001, 29(4): 976-985.

[78] T. M. Schmeing, P. B. Moore, and T. A. Steitz. Structures of deacylated tRNA mimics bound to the E site of the large ribosomal subunit. *RNA*, 2003, 9: 1345-1352.

[79] P. C. Whitford, P. Geggier, R. B. Altman, S. C. Blanchard, J. N. Onuchic and K. Y. Sanbonmatsu. Accommodation of aminoacyl-tRNA into the ribosome involves reversible excursions along multiple pathways. *RNA*, 2010, 16: 1196-1204.

[80] J. M. Deutsch and T. Kurosky. New Algorithm for Protein Design. *Phys. Rev. Lett.*, 1996, 76(2): 323-326.

[81] T. P. Lybrand. Ligand-protein docking and rational drug design. *Curr. Opin. Struc. Biol.*, 1995, 5: 224-228.

[82] W. P. Russ, D. M. Lowery, P. Mishra, M. B. Yaffe and R. Ranganathan. Natural-like function in artificial WW domains. *Nature*, 2005, 437: 579-583.

[83] P. Koehl and M. Delarue. Mean-field minimization methods for biological macromolecules. *Curr. Opin. Struc. Biol.*, 1996, 6: 222-226.

[84] A. Irbäck, C. Peterson, F. Potthast, and E. Sandelin. Monte Carlo procedure for protein design. *Phys. Rev. E*, 1998, 58: 5249-5252.

[85] X. I. Ambroggio and B. Kuhlman. Computational Design of a Single Amino Acid Sequence that Can Switch between Two Distinct Protein Folds. *J. Am. Chem. Soc.*, 2006, 128(4): 1154-1161.

[86] B. Kuhlman and D. Baker. Native protein sequences are close to optimal for their structures. *PNAS*, 2000, 97(19): 10383-10388.

[87] S. Chaudhury and J. J. Gary. Conformer Selection and Induced Fit in Flexible Backbone Protein-Protein Docking Using Computational and NMR Ensembles. *J. Mol. Biol.*, 2008, 381: 1068-1087.

[88] Y. Liu and B. Kuhlman. RosettaDesign server for protein design. *Nucleic Acids Res.*, 2006, 34: W235-W238.

[89] J. Spears, X. Xiao, C. Hall and P. F. Agris, personal communication.

What is claimed is:

1. A peptide comprising the amino acid sequence:
R-W-Q/N-H/M-Xaa-Xaa-F-Pho/H-Xaa-G/A/L-W-R-Xaa-Xaa-G
wherein Xaa is any amino acid; and
Pho is a hydrophobic amino acid.

2. The peptide of claim 1 selected from the group consisting of:

```
                                          (SEQ ID NO: 4)
R-W-Q-M-T-A-F-A-H-G-W-R-H-S-G;

(SEQ ID NO: 7)
R-W-N-H-Q-S-F-W-H-G-W-R-A-C-G;

(SEQ ID NO: 9)
R-W-Q-H-H-S-F-H-P-L-W-R-M-S-G;
and (SEQ ID NO: 42)
R-W-N-H-C-Q-F-W-S-G-W-R-A-N-G.
```

3. The peptide of claim 1, wherein the peptide binds to the anticodon stem and loop (ASL) of human lysine tRNA (tRNA$^{Lys3}$).

4. The peptide of claim 1, wherein the peptide inhibits reverse transcription of human immunodeficiency virus (HIV).

5. The peptide of claim 3, wherein said ASL of human lysine tRNA is hASL$^{Lys3}_{UUU}$.

6. The peptide of claim 3, wherein said ASL of human lysine tRNA is modified hASL$^{Lys3}_{UUU}$.

7. The peptide of claim 3, wherein said peptide binds with an affinity ($K_d$) of about 0.01 to 2.0 μM.

8. The peptide of claim 3, wherein said peptide has a $K_d$ of 0.05 to 1.0 μM.

9. The peptide of claim 2, wherein the peptide binds to the anticodon stem and loop (ASL) of human lysine tRNA (tRNA$^{Lys3}$).

10. The peptide of claim 2, wherein the peptide inhibits reverse transcription of human immunodeficiency virus (HIV).

11. The peptide of claim 2, wherein said peptide binds with an affinity ($K_d$) of about 0.01 to 2.0 μM.

12. The peptide of claim 2, wherein said peptide binds with an affinity ($K_d$) of about 0.01 to 2.0 μM.

* * * * *